(12) United States Patent  
Granevitze et al.

(10) Patent No.: US 10,899,504 B2  
(45) Date of Patent: Jan. 26, 2021

(54) DEVICES FOR MONITORING FOOD FRESHNESS AND METHODS OF USING SAME

(71) Applicant: Zur Granevitze, Mazkeret Batya (IL)

(72) Inventors: Zur Granevitze, Mazkeret Batya (IL); Ben-Zion Magnes, Meitar (IL)

(73) Assignee: Zur Granevitze, Mazkeret Batya (IL)

( * ) Notice: Subject to any disclaimer, the term of this patent is extended or adjusted under 35 U.S.C. 154(b) by 0 days.

(21) Appl. No.: 16/466,257

(22) PCT Filed: Dec. 17, 2017

(86) PCT No.: PCT/IL2017/051355  
§ 371 (c)(1),  
(2) Date: Jun. 3, 2019

(87) PCT Pub. No.: WO2018/116294  
PCT Pub. Date: Jun. 28, 2018

(65) Prior Publication Data  
US 2020/0062456 A1  Feb. 27, 2020

Related U.S. Application Data

(60) Provisional application No. 62/435,864, filed on Dec. 19, 2016.

(51) Int. Cl.  
*B65D 25/54* (2006.01)  
*B65D 85/80* (2006.01)  
*G01N 21/80* (2006.01)  
*G01N 33/04* (2006.01)  
*G01N 33/12* (2006.01)

(52) U.S. Cl.  
CPC ............. *B65D 25/54* (2013.01); *B65D 85/80* (2013.01); *G01N 21/80* (2013.01); *G01N 33/04* (2013.01); *B65D 2203/12* (2013.01); *G01N 33/12* (2013.01)

(58) Field of Classification Search  
CPC ........ B65D 25/54; B65D 85/80; B65D 79/02; B65D 2203/12; G01N 33/12; G01N 21/78; G01N 21/80; G01N 33/04; G01N 31/221; C12Q 1/04  
See application file for complete search history.

(56) References Cited

U.S. PATENT DOCUMENTS 3,102,418 A  9/1963  Schalm et al.  
3,494,770 A  2/1970  Smerak et al.  
(Continued)

FOREIGN PATENT DOCUMENTS

CN  201555823 U  8/2010  
CN  201683694 U  12/2010  
(Continued)

OTHER PUBLICATIONS

Cavallo et al., (2014) Preparation of a milk spoilage indicator adsorbed to a modified polypropylene film as an attempt to build a smart packaging. Journal of Food Engineering, vol. 136: 48-55.  
(Continued)

*Primary Examiner* — Dennis White  
(74) *Attorney, Agent, or Firm* — The Roy Gross Law Firm, LLC; Roy Gross

(57) ABSTRACT

The present invention provides devices for real-time, continuous, detection of spoilage and freshness of food products.

20 Claims, 27 Drawing Sheets

(56) References Cited

U.S. PATENT DOCUMENTS

| | | | |
|---|---|---|---|
| 3,806,416 | A | 4/1974 | Mollering et al. |
| 4,003,709 | A | 1/1977 | Eaton et al. |
| 4,280,011 | A | 7/1981 | Desimone |
| 5,094,761 | A | 3/1992 | Trinh et al. |
| 5,219,838 | A | 6/1993 | Tomita et al. |
| 5,330,773 | A | 7/1994 | Piliero et al. |
| 6,372,220 | B1 | 4/2002 | Shukla |
| 6,495,368 | B1 | 12/2002 | Wallach |
| 6,723,285 | B2* | 4/2004 | Chen ............... G01N 21/80 422/417 |
| 8,211,715 | B1* | 7/2012 | Royds ............... G01N 33/569 422/403 |
| 2001/0026821 | A1 | 10/2001 | Scoville et al. |
| 2002/0119233 | A1 | 8/2002 | Huang et al. |
| 2002/0151075 | A1 | 10/2002 | Chen et al. |
| 2003/0143112 | A1* | 7/2003 | Suslick ............ G01N 31/22 422/400 |
| 2006/0057022 | A1 | 3/2006 | Williams et al. |
| 2006/0121165 | A1 | 6/2006 | Morris |
| 2008/0176273 | A1* | 7/2008 | Eden ............... C12M 41/36 435/30 |
| 2010/0215878 | A1 | 8/2010 | Hurme et al. |
| 2012/0107191 | A1 | 5/2012 | Strahle et al. |

FOREIGN PATENT DOCUMENTS

| | | |
|---|---|---|
| CN | 102174437 A | 9/2011 |
| CN | 202891414 U | 4/2013 |
| CN | 103529034 A | 1/2014 |
| CN | 104443858 A | 3/2015 |
| CN | 104570828 A | 4/2015 |
| DE | 2251576 A1 | 5/1974 |
| DE | 102004019427 A1 | 11/2005 |
| DK | 459684 A | 9/1984 |
| EP | 0890835 A1 | 1/1999 |
| IE | S20060034 A2 | 7/2007 |
| JP | 2001078697 A | 3/2001 |
| JP | 2002257813 A | 9/2002 |
| JP | 2004359319 A | 12/2004 |
| JP | 2012136471 A | 7/2012 |
| KR | 20030096077 A | 12/2003 |
| KR | 20070107918 A | 11/2007 |
| RU | 2332010 C1 | 8/2008 |
| UA | 74848 C2 | 11/2004 |
| WO | 9919232 A2 | 4/1999 |
| WO | 2005080964 A1 | 9/2005 |
| WO | 2006032025 A1 | 3/2006 |
| WO | 2013045443 A1 | 4/2013 |
| WO | 2014102556 A1 | 7/2014 |
| WO | 2015101992 A2 | 7/2015 |
| WO | 2015112679 A1 | 7/2015 |

OTHER PUBLICATIONS

Cervantes and Dos Santos (2011) Reduction of azo dyes by anaerobic bacteria: microbiological and biochemical aspects. Reviews in Environmental Science and Bio/Technology, 10(2): 125-137.
Chajan et al., (2005) Changes of pigments and color in sardine (*Sardinella gibbosa*) and mackerel (*Rastrelliger kanagurta*) muscle during iced storage. Food Chemistry, 93(4): 607-617; abstract.
Fleischmann et al., (2015) Polymers and Dyes: Developments and Applications. Polymers, 7(4): 717-746.
Fouad and Richards (1953) The use of glucose inorganic salts media in the classification of the coli-aerogenes bacteria. I. The Methyl Red and Voges-Proskauer reactions. Proceedings of the Society for Applied Bacteriology, 16(1): 35-44; abstract.
Fuzeau-Braesch (1972) Pigments and color changes. Annual Review of Entomology, 17: 403-424; p. 403.
Guo et al., (2010) Effects of milk concentration and freshness on microwave dielectric properties. Journal of Food Engineering, 99(3): 344-350.
Kidd et al., (1996) Fetal death after exposure to methylene blue dye during mid-trimester amniocentesis in twin pregnancy. Prenat Diagn 16(1): 39-47.
Ledenbach L.H., Marshall R.T. (2009) Microbiological Spoilage of Dairy Products. In: Sperber W., Doyle M. (eds) Compendium of the Microbiological Spoilage of Foods and Beverages. Food Microbiology and Food Safety. Springer, New York, NY; pp. 41-67.
Lu et al., (2013) Milk Spoilage: Methods and Practices of Detecting Milk Quality. Food and Nutrition Sciences 4: 113-123.
Medvedová and Valik (2012) *Staphylococcus aureus*: Characterisation and Quantitative Growth Description in Milk and Artisanal Raw Milk Cheese Production. Structure and Function of Food Engineering, Ayman Amer Eissa, IntechOpen; 33 pages.
Mrvčić et al., (2012) Interaction of lactic acid bacteria with metal ions: opportunities for improving food safety and quality. World J Microbiol Biotechnol 28(9): 2771-2782.
Orleans, K.A.; "Microbiological and Chemical Changes During Shelf-Life in Regular and Chocolate Milk". Presented in Partial Fulfillment of the Requirements for the Degree Master of Science in the Graduate School of the Ohio State University, the Ohio State University, 2011. 102 pages.
Pérez-Diaz and McFeeters (2009) Modification of azo dyes by lactic acid bacteria. J Appl Microbiol 107(2): 584-589.
Popov-Raljić et al., (2008) Color Changes of UHT Milk During Storage. Sensors 8(9): 5961-5974.
Saadatzadeh et al., (2013) Probiotic Properties of Lyophilized Cell Free Extract of Lactobacillus casei. Jundishapur J Nat Pharm Prod 8(3):131-137.
Samaržija et al., (2012) Psychrotrophic bacteria and milk and dairy products quality. Mljekarstvo 62(2): 77-95.
Soukoulis et al., (2010) Proton transfer reaction time-of-flight mass spectrometry monitoring of the evolution of volatile compounds during lactic acid fermentation of milk. Rapid Commun Mass Spectrom 24(14): 2127-2134; abstract.
Stovall and Nichols (1918) The Methyl Red and Voges-Proskauer Reactions with Special Reference to Routine Water Analysis. The Journal of Infectious Diseases 23(3): 229-239.
Tram et al., (2014) Translating Bacterial Detection by DNAzymes into a Litmus Test. Angewandte Chemie International Edition, 53(47): 12799-12802; abstract.
Valero et al., (2000) Chemical and sensorial changes in milk pasteurised by microwave and conventional systems during cold storage. Food Chemistry, 70(1): 77-81; abstract.
Van Slyke and Bosworth (1916) Chemical changes in the souring of milk. The Journal of Biological Chemistry, 24: 191-202.
Wise et al., (1968) Changes in Milk Products Sham Fed to Calves. III. Effects of Concentration of Fat. Journal of Dairy Science 51(7): 1077-1080.
Wu et al., (2015) 3D-printed microelectronics for integrated circuitry and passive wireless sensors. Microsystems & Nanoengineering 1: 15013; 9 pages.
International Search Report PCT/IL2017/051355 Completed Feb. 8, 2018; dated Feb. 8, 2018 4 pages.
Witten Opinion of the International Searching Authority PCT/IL2017/051355 dated Feb. 8, 2018 3 pages.

* cited by examiner

DEVICES FOR MONITORING FOOD FRESHNESS AND METHODS OF USING SAME

RELATED APPLICATIONS

This application is a National Phase of PCT Patent Application No. PCT/IL2017/051355 having International filing date of Dec. 17, 2017, which claims the benefit of priority of U.S. Provisional Application No. 62/435,864 filed on Dec. 19, 2016. The contents of the above applications are all incorporated by reference as if fully set forth herein in their entirety.

FIELD OF THE INVENTION

The present invention provides devices for real-time, continuous, detection of spoilage and freshness of food products.

BACKGROUND OF THE INVENTION

Food products, especially, those containing substantial amounts of proteins and/or sugars and/or fats, spoil over time due to the growth of microbes, such as lactobacteria, yeasts and fungi. Food storage devices are commonly used to protect food products during storage, under various conditions, in order to maintain food freshness.

Several food quality indicators providing measures of food quality are known in the art, as disclosed for example in U.S. Patent Application No 2012/0107191.

Attempts to include such indicators in food packaging have been made. For example, Cavallo et al. (J. Food Eng., 136:48-55, 2014) disclose a modified polypropylene film containing methylene blue, for use in packaging of food products, such as, milk.

DE 102004019427 discloses an indicator, which includes lactic acid strips and is attached to a food container or an opening area of a food container The lactic acid strips indicate the current condition of the food based on pH value measurement made on the food.

U.S. Pat. No. 6,723,285 discloses a system for retail packaging of a food product indicating to a consumer a status of a quality of the food product. The system comprises: (a) a container having a first compartment containing a first portion of the food product for consumption by the consumer and a second compartment containing a second portion of the food product; and (b) an indicator, said indicator mixed with the portion of the food product in said second compartment. The indicator may be capable of indicating a change in pH.

US Patent Application No. 2006/0057022 also discloses a label that includes food quality indicators and that can be affixed inside a clear food packaging or outside a breathable or gas-permeable food packaging and read by anyone to determine the quality of the packaged food.

WO/2014/102556 discloses a container with an indicating device. The indicating device comprises an indicator fixed to an inner wall of the container. The indicator is arranged so as to provide an intermediate space part between the indicator and the inner wall of the container.

There is an unmet need for a food storage device capable of providing a real time reliable indication of freshness or spoilage of the food contained therein, without exposing the indicator composition to substances that can significantly jeopardize its accuracy.

SUMMARY OF THE INVENTION

The present invention provides a storage device comprising a food product, and at least one chamber comprising a sample of said food product, where the at least one chamber further comprises a composition comprising at least one indicator.

Advantageously, the storage device disclosed herein constantly provides a real-time accurate and visible indication of the freshness (and/or spoilage) of the food contained therein. Thus, a consumer can easily determine, based on the indication, whether the food product is fresh. The indication is afforded by an indicator composition containing a sample of the food product, which is maintained and stored at the exact same conditions (e.g. temperature, storage period) under which the food product (from which said sample is derived) is maintained and stored. Surprisingly, the indication provided by the indicator composition within the device disclosed herein is not obscured by the contents of the food product even when the food sample and the food product are of substantially similar contents.

It is to be understood that 'exact same conditions' with respect to the conditions sensed by the food sample includes environmental conditions, such as, storage temperature, duration of storage, and the like, that are equivalent, essentially similar, substantially similar or highly similar to the storage conditions of the food product. In fact, it has been shown herein below that the rate of spoilage of a small food sample (e.g. a food sample in the at least one chamber) and a large food sample (e.g. the food product within the device from which the food sample has been derived) are similar (FIG. 2).

The term 'substantially similar contents' as used herein refers to the extent of similarity between the food product and the food sample. The term includes, but is not limited to, similarity in dilution and/or other similarities such that the food sample is essentially not modified with respect to the food product.

In some embodiments, there is provided a device comprising a food product; and at least one chamber comprising a sample of said food product and a composition comprising at least one indicator, wherein the food sample within the chamber is diluted compared to the food product within the storage device.

In some embodiments, the terms "device", "storage device" and "food storage device" as used herein are interchangeable.

In some embodiments, the food sample within the at least one chamber is diluted to 1% to 50% compared to the food product within the storage device.

In some embodiments, the at least chamber is an impervious three-dimensional structure.

In some embodiments, the at least one chamber is attached to the device.

In some embodiments, the device further comprises at least one container, wherein said at least one container contains the food product.

In some embodiments, the at least one chamber is attached to the at least one container.

In some embodiments, the at least one chamber comprises a transparent window, such that at least a portion of said chamber is being externally viewable through the transparent window.

In some embodiments, at least one indicator is selected from bacterial indicators, redox indicators and pH indicators.

In some embodiments, the at least one indicator is provided in a concentration such that it changes its color in response to spoilage of the food sample.

In some embodiments, at least one indicator is a pH indicator.

In some embodiments, at least one indicator is a bacterial indicator.

In some embodiments, the indicator changes color upon a change of pH smaller than 0.1 pH unit In some embodiments, the at least one bacterial indicator is devoid of quaternary ammonium salts and quaternary ammonium moieties.

In some embodiments, the at least one bacterial indicator provides a detectable indication in the presence of a bacterial population above a pre-determined threshold.

In some embodiments, the composition comprises a plurality of indicators.

In some embodiments, the at least one indicator is selected from bromothymol blue, cresol red, phenol red, methyl red, bromocresol blue, indigo carmine, carmoisine red, tartrazine, bromocresol green, bromophenol blue and methyl orange.

In some embodiments, the composition further comprises at least one transition metal moiety.

In some embodiments, the transition metal moiety comprises Cr(III).

In some embodiments, the chamber further comprises an aqueous solvent.

In some embodiments, the food product comprises a dairy product.

In some embodiments, there is provided a device comprising a food product, and at least one chamber comprising a sample of said food product; a composition comprising at least one indicator; and a plurality of compartments, separated from one another by a membrane.

In some embodiments, the membrane is a porous membrane.

In some embodiments, the membrane is impermeable to particles having an average size distribution above 10 nm.

In some embodiments, the membrane is impermeable to water insoluble organic colloidal materials.

In some embodiments, the membrane is impermeable to fatty acids and proteins.

In some embodiments, the membrane comprises pores having an average size within the range of 0.01 microns to 1 micron.

In some embodiments, the membrane is having a porosity from 10% to 80%.

In some embodiments, the plurality of compartments comprises first and second compartments, the first compartment comprises the food sample, and the second compartment comprises a filtered portion of the food sample.

In some embodiments, the second compartment comprises a transparent window, such that at least a portion of said compartment is being externally viewable through the transparent window.

In some embodiments, the sample of said food product within the at least one chamber is diluted compared to the food product within the storage device.

In some embodiments, there is provided a device comprising a food product, and at least one chamber, wherein said at least one chamber comprising a sample of said food product and a composition comprising at least one bacterial indicator.

In some embodiments, at least one bacterial indicator provides an indication upon reduction of an internal double bond selected from an N=N bond and a C=C bond.

In some embodiments, the at least one bacterial indicator is not anti-bacterial.

In some embodiments, the at least one bacterial indicator is devoid of quaternary ammonium salts and quaternary ammonium moieties.

In some embodiments, the bacterial indicator provides a detectable indication in the presence of a bacterial population above a pre-determined threshold.

In some embodiments, at least one bacterial indicator is selected from the group consisting of methyl red, methyl orange, indigo carmine, bromophenol blue, carmoisine red, tartrazine, bromocresol green and combinations thereof.

In some embodiments, at least one bacterial indicator comprises an azo dye

In some embodiments, the at least one chamber further comprises at least one transition metal moiety.

In some embodiments, the at least one transition metal moiety comprises Cr(III).

In some embodiments, there is provided a use of a dye selected from indigo carmine, tartrazine, carmoisine red and combinations thereof as a food quality indicator.

In some embodiments, there is provided a method of detecting food spoilage, the method comprising
providing a device comprising a food product; and at least one chamber comprising a sample of said food product and a composition comprising at least one indicator, wherein the food sample within the chamber is diluted to compared to the food product within the storage device; and
detecting a color change in the at least one chamber, thereby detecting spoilage of the food product.

In some embodiments, there is provided a method of detecting food spoilage, the method comprising
providing a device comprising a food product, and at least one chamber comprising a sample of said food product; a composition comprising at least one indicator; and a plurality of compartments, separated from one another by a membrane; and
detecting a color change in the at least one chamber, thereby detecting spoilage of the food product.

In some embodiments, there is provided a method of detecting food spoilage, the method comprising
providing a device comprising a food product, and at least one chamber, wherein said at least one chamber comprising a sample of said food product and a composition comprising at least one bacterial indicator; and
detecting a color change in the at least one chamber, thereby detecting spoilage of the food product.

There is provided a method for determining food quality, the method comprising providing a dye selected from indigo carmine, tartrazine, carmoisine red and combinations thereof; and
adding the dye to a food product, wherein a change in color of the dye is indicative of spoilage of the food product.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

DETAILED DESCRIPTION

Figure 1:
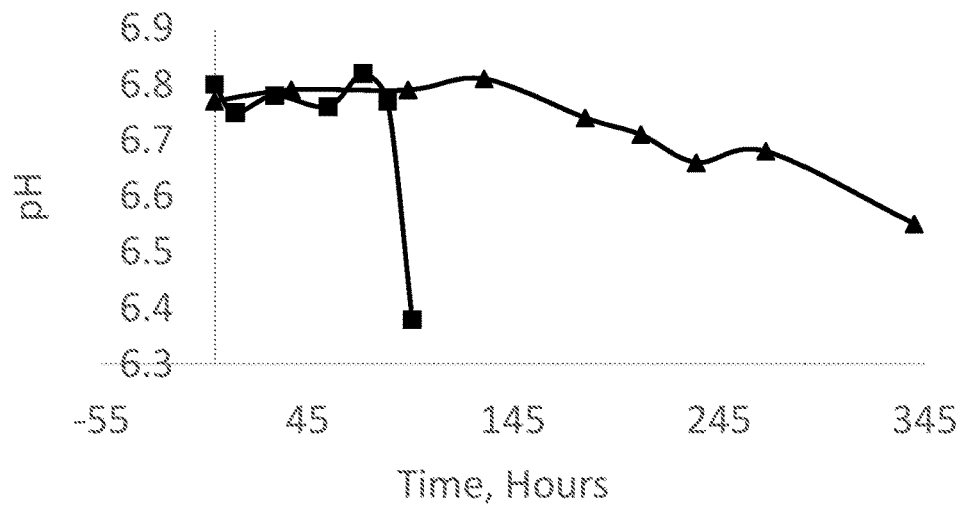
FIG. 1 is a graph showing the pH of milk samples vs. time for milk samples stored at 4° C. (triangles) and at 18° C. (squares).

The present invention provides devices and methods for monitoring the freshness of food products. Generally, the devices contain one or more chambers, each includes a solution comprising one or more indicators and a sample of the food product. The one or more chambers are configured to provide an indication of spoilage of the food sample. The indication may be based on pH and/or on components related to the presence of microbes. Typically, a decrease in pH and an increase in the amount of compounds associated with microbes indicate food spoilage.

The devices of the invention may be implemented in food containers, such as milk cartons, cheese or yogurt containers, cans of food products and the like. The devices may also be used for detecting food spoilage in commercial containers, which contain a batch of food containers, including, for example meat containers and containers of dairy products.

In some embodiments, there is provided a storage device comprising a food product, and at least one chamber comprising a sample of said food product and a composition comprising at least one indicator, wherein the food sample within the at least one chamber is diluted compared to the food product.

The term "diluted" as used herein refers to a difference in contents, such as, concentration, between the food sample and to the food product, such that, the concentration of certain components in the food sample is relatively lower compared to their concentration in the food sample. In some embodiments, diluted refers to dilution within the range of 0.01% to 90%.

As used herein, 0.01% dilution refers to 0.01 w/w or w/v or v/v in the food sample compared to 100 w/w or w/v or v/v in the food product, of a given component. Thus, 0.01% dilution may refer to w/w ratio or v/v ratio among others. The dilution may be obtained by adding a pre-determined amount of diluent (solvent) to the food sample, thereby obtaining the desired dilution. The diluent may refer to a solvent, and may include an aqueous solution. In addition, a food sample diluted by x % compared to the food product refers to a composition (i.e. a food sample) containing x % of the food product. The remaining of the food sample composition (i.e. 100%-x %), also referred to herein as a 'diluent', may include a solvent and/or an indicator composition. In some embodiments, the diluent is essentially the indicator composition. In some embodiments, the diluent comprises water. In some embodiments, the diluent comprises water and is having an essentially neutral pH (pH~7). In some embodiments, the diluent may be slightly basic, for example, the diluent may be water having a pH higher than 7, such as, a pH within the range of 7.1 to 8.5. In some embodiments, the diluent may include a mixture of water and ethanol. In some embodiments, the diluent may include less than 0.05% ethanol in water.

Thus, in some embodiments, the chamber comprises a food sample, an indicator composition and a solvent.

In some embodiments, the solvent is an aqueous solvent.

The term "aqueous solvent" as used herein includes water or a mixture of water and organic solvent, so long that the amount of organic solvent is relatively low, e.g. less than 5%, or less than 1%.

It is to be understood that if an organic solvent, such as, ethanol, is present in the food sample, it is present in non-toxic amounts, which essentially do not affect the viability of microbes.

In some embodiments, the food sample within the chamber is diluted to 0.1% to 75% compared to the food product within the storage device. In some embodiments, the food sample within the chamber is diluted to 1% to 50% compared to the food product within the storage device. In some embodiments, the food sample within the chamber is diluted to 5% to 30% compared to the food product within the storage device.

In some embodiments, the device further comprises at least one container, said at least one container contains the food product.

The term 'container' as used herein is interchangeable with any packaging, specifically, any food packaging, including, but not limited to, paper containers such as those used for packaging milk, paperboard coated with a waterproof plastic, generally polyethylene, containers made of glass, polymers and metal among other materials that may be suitable for food packaging.

In some embodiments, the device comprises a plurality of containers, each container comprises food product.

In some embodiments, the at least one chamber is attached to the device.

In some embodiments, the at least one chamber is attached to the at least one container within the device.

In some embodiments, the device comprises a plurality of containers, wherein at least one chamber is attached to at least one container of said plurality of containers.

In some embodiments, the device comprises a plurality of containers, wherein at least one chamber is attached to each container of said plurality of containers.

In some embodiments, the at least one chamber is an impervious three-dimensional structure comprising a first wall and a second wall, said first wall is facing a wall of the device.

In some embodiments, said first wall and the wall of the device form a mutual wall, which is a single wall mutual to the device and the at least one chamber.

In some embodiments, the contents of the at least one chamber is visible. In some embodiments, a color change of the contents of the at least one chamber is visible.

In some embodiments, the at least one chamber is impervious to gases. In some embodiments, the at least one chamber is impervious to liquids. In some embodiments, the at least one chamber is impervious to light. In some embodiments, the at least one chamber is impervious to air. In some embodiments, the at least one chamber is impervious to aqueous solutions. In some embodiments, the chamber is made of the same material as the device. In some embodiments, the thermal conductivity and permeability of the materials forming the chamber and the device are similar. In some embodiments, the temperature, humidity and/or any other condition associated with storage of the food product, have essentially similar effect(s) on the device and the chamber, such that, the food sample and the food product, from which it is obtained, are maintained and stored at the exact same conditions.

In some embodiments, the at least one chamber is made of materials impermeable to gases. In some embodiments, the at least one chamber is made of materials impermeable to liquids. In some embodiments, the materials are having thermal conductivity such that the food sample within the at least one chamber is sensing the same temperatures as the food product stored in the storage device.

In some embodiments, the at least one chamber is made of a material comprising glass, rubber, polymers, gas impermeable polymers, liquid impermeable polymer, gas and liquid impermeable polymers, metals, paperboard coated with a waterproof polymer, such as, polyethylene, and combinations thereof.

In some embodiments, the first wall, or at least a portion of the first wall which is in contact with, and/or in close vicinity to, the at least one chamber is made of materials impermeable to the food product, gases, the food sample, or any substance contained within the at least one chamber, such that, there is no transition of substances from the device to the food product and vice versa, including transition through flow or diffusion. Thus, in some embodiments, the first wall, or at least the aforementioned portion thereof, is impermeable to gases. In some embodiments, the first wall, or at least the aforementioned portion thereof, is made of materials impermeable to liquids.

In some embodiments, the second wall is made of materials impermeable to gases. In some embodiments, the second wall is made of materials impermeable to liquids.

Without wishing to be bound to any theory or mechanism, some indicators may oxidize in the presence of oxygen from the air. An impervious chamber may enable separation and, optionally, isolation of the indicator composition from the environment outside the chamber, and thus provide more credible indication as to the freshness or spoilage of the food sample. An additional credibility of the indication may result from placing the chamber in substantially similar conditions to the conditions of the food product within the device, such that the food sample in the chamber spoils at the same rate as the food product in the device.

It is to be understood that the at least one chamber may be attached to any part of the device, at any direction, including, but not limited to, any wall of the device, top, bottom and/or sides, it may be attached to an opening of the device (e.g. a cap), inside the device and/or outside the device. Similarly, the at least one chamber may be attached to any part of the at least one container within the device.

In some embodiments, the at least one chamber is attached to a wall of the device.

In some embodiments, the wall of the device is thermally conductive.

The term "attached" as used herein is interchangeable with the terms "bound", "linked" "connected", "stitched" and the like. Attachment may be achieved by any method known in the art, such as, by the use of magnets, threads and adhesives, including, but not limited to, biocompatible adhesives.

In some embodiments, attachment between the at least one chamber and the device may be reversible.

In some embodiments, attachment between the at least one chamber and the device may be irreversible.

In some embodiments, the at least one chamber is attached to a wall of the device at least along the perimeter edges of the first wall of the at least one chamber. In some embodiments, the at least one chamber is glued to a wall of the device by an adhesive. In some embodiments, the adhesive is a non-toxic adhesive. In some embodiments, the at least one chamber is fastened to a wall of the device. In some embodiments, the at least one chamber is clipped to a wall of the device.

In some embodiments, at least one of the first wall and second wall comprises a transparent window, such that at least a portion of the content of said at least one chamber being externally viewable through the transparent window.

In some embodiments, the transparent window is formed from a transparent material. In some embodiments, the transparent material comprises glass or a transparent polymer. In some embodiments, the transparent window is a glass transparent window. In some embodiments, the transparent window is a polymeric transparent window.

In some embodiments, the composition comprising the at least one indicator is printed on the transparent window.

In some embodiments, the at least one chamber may comprise an indicator printed onto a substrate. The substrate may be part of the chamber, e.g. a wall of the chamber. Thus, the indicator composition may be printed on one or more walls of the chamber. In some alternative embodiments, the indicator composition may be printed on one or more walls of the device and/or on one or more walls of the at least one container within the device and/or on the food product. In some embodiments, the chamber may be a substrate comprising a print of the food sample and a print of the indicator, thereby forming a printed substrate. In some embodiments, the printed substrate is covered with an impermeable material. In some embodiments, the device comprises an opening covered reversibly with a cap, wherein the indicator and the food sample are printed on the cap.

In some embodiments, the composition comprising the at least one indicator is printed on the food product.

In some embodiments, the composition comprising at least one indicator is printed on a wall of the at least one chamber. In some embodiments, the composition comprising at least one indicator is printed on the external wall of said at least one chamber. In some embodiments, the composition comprising the at least one indicator is printed on the second wall of said at least one chamber.

In some embodiments, the composition comprising the at least one indicator is printed on the mutual wall, namely, the wall shared between the device and the at least one chamber.

In some embodiments, the indicator creates a visible mark when the indicator is visible. In some embodiments, the indicator is printed to form a visible mark when the indicator is visible. For example, the mark may be in the shape of a word, such as, 'spoiled' or 'S' or thump down or 'X' or red line(s), when the indication corresponds to a spoiled food product, otherwise, i.e. when the food product is fresh, the mark is invisible, and, optionally, a mark indicating freshness may become visible. Alternatively, the mark may be in the shape of the word 'Fresh' or has the shape of thump up or the shape of a 'v' mark or green line(s), when the indication corresponds to a fresh food product, otherwise, i.e. when the food product is spoiled, the mark may be invisible, and, optionally, a mark indicating spoilage may become visible.

In some embodiments, the indicator composition is not chemically incorporated within the material forming the device, or the material forming the at least one container. In some embodiments, the indicator composition is not part of the formulation forming the device, or the material forming the at least one container.

In some embodiments, the at least one indicator is selected from a group consisting of bacterial indicators, for example redox indicators and pH indicators. In some embodiments, the at least one indicator is selected from bacterial indicators and pH indicators. In some embodiments, the at least one indicator is a bacterial indicator. In some embodiments the at least one indicator is a pH indicator.

In some embodiments, the indicator changes color at a rate proportional to the concentration of microbes and/or to the change in pH.

The term "indicator" as used herein refers to any substance capable of changing color with a change in a property in its environment. Changing color also includes, without limitation, losing color, for example, when a colored indicator becomes white, colorless or substantially transparent; and gaining color, for example, when a white, colorless or substantially transparent indicator becomes colored. Environmental properties may include for example, pH and amount of bacterial population. Therefore, pH indicators and bacterial indicators are preferable examples of materials used as indicators in the devices of the current invention. As a change in the pH of food products may be caused when a threshold amount of bacteria, or bacterial by-products (e.g. nitrates, nitrites, sulfur and sulfates) are produced, there may be an overlap between bacterial indicators and pH indicators. Especially preferred indicators are colored conjugated organic molecules, which change their color in response to a change in pH, which leads to alternation in the pi conjugation of the indicator molecule; and colored conjugated organic molecules, which change their color in response to an enzymatic or bacterial reaction, which leads to alternation in the pi conjugation of the indicator molecule.

In some embodiments, the indicator changes color upon a change of pH smaller than 1 pH unit, smaller than 0.1 pH unit, or smaller than 0.05 pH unit.

In some embodiments, the indicator changes color upon a change of pH smaller than 0.1 pH units, within the pH region of 5 to 7. In some embodiments, the indicator changes color upon a change of pH smaller than 0.1 pH units, within the pH region of 6 to 7.

In some embodiments, the indicator changes color upon a change of pH smaller than 0.05 pH units, within the pH region of 5 to 7. In some embodiments, the indicator changes color upon a change of pH smaller than 0.05 pH units, within the pH region of 6 to 7.

It is noted that while the bacteria may or may not be harmful, the waste products of bacteria may be unpleasant to taste or may even be harmful.

In some embodiments, the pH indicator provides a detectable mark within any pH applicable to the indication of freshness or spoilage of food products. In some embodiments, the pH indicator provides a detectable mark within a pH range of 3.0 to 9.0. In some embodiments, the pH indicator provides a detectable mark within a pH range of 4.0 to 9.0. In some embodiments, the pH indicator provides a detectable mark within a pH range of 5.0 to 9.0. In some embodiments, the pH indicator provides a detectable mark within a pH range of 8.0 to 9.0. In some embodiments, the pH indicator provides a detectable mark within a pH range of 7.5 to 8.0. In some embodiments, the pH indicator provides a detectable mark within a pH range of 7.0 to 7.5. In some embodiments, the pH indicator provides a detectable mark within a pH range of 6.3 to 7.0. In some embodiments, the pH indicator provides a detectable mark within a pH range of 5.7 to 6.3. In some embodiments, the pH indicator provides a detectable mark within a pH range of 5.0 to 5.7.

In some embodiments, the bacterial indicator provides a detectable indication in the presence of an amount of bacteria above a certain threshold.

In some embodiments, the threshold as determined by the United States Food and Drug Administration (FDA) which promotes adherence to a food spoilage safety standard of approximately 10 million colony forming units per gram, or CFU/g. Accordingly, food products with measured bacterial levels above the FDA standard are considered unsafe for consumption and should therefore be immediately discarded.

In some embodiments, the bacterial indicator provides a detectable indication in the presence of compounds associated with the presence of an amount of bacteria above a certain threshold.

It is to be understood that bacterial indicators are not anti-bacterial materials.

In some embodiments, the compounds are the result of bacterial decomposition of the food product.

In some embodiments, the compounds are carboxylic acids. In some embodiments, the compounds comprise lactic acid and/or butyric acid. In some embodiments, the compounds are amines, nitrates, nitrites, sulfur and/or sulfates.

In some embodiments, the bacterial population comprises lactobacteria.

In some embodiments, the bacterial population comprises psychrotrophic bacteria.

Psychrotrophic bacteria usually account for more than 90% of the total microbial population in cooled raw milk. The optimal metabolic activity of psychrotrophic bacteria is expressed at temperatures between 20 to 30° C., yet, they can grow and multiply at low temperatures through an enrichment of polyunsaturated fatty acid in their membrane lipids.

Paenibacillus is a spore-forming bacterium that is found in spoiled milk. It is responsible for spoiling milk and causes curdling as well. Paenibacillus also contributes to off flavors in a variety of other foods. Paenibacillus may withstand the extreme conditions of pasteurization and subsequent cooling in its spore state, allowing it to survive in milk and other foods.

In some embodiments, the microbe population comprises fungi. In some embodiments, the fungi comprise Saccharomyces cerevisiae and/or Hansenula anomala. In some embodiments, the microbe population comprises yeast.

In some embodiments, the at least one bacterial indicator is selected from the group consisting of methyl red, methyl orange, bromophenol blue, indigo carmine, carmoisine red, tartrazine, bromocresol green and combinations thereof.

In some embodiments, the composition of the at least one indicator includes an active ingredient that is adapted to change color within a defined color range that is dependent upon the concentration of compounds associated with food spoilage.

In some embodiments, the at least one indicator is a colorimetric indicator.

The term "colorimetric indicator" as used herein refers to an indicator capable of changing color, including the change from colored to colorless (e.g. white), in response to sensing, e.g. interacting with, compounds characteristic of spoiled food.

In some embodiments, the colorimetric indicator may provide a color indication which includes any one or more of a first color indicating freshness (e.g. green), a second color indicating spoilage (e.g. red) and a third color indicating that the food product is about to be spoiled (e.g. yellow). The latter may provide a specific date, or time window, during which the food product is still fresh but by after the specified date, or by the end of the time window, the food product will be considered spoiled.

In some embodiments, the detectable indication may include any one or more of the following indications: an indication of freshness, an indication of spoilage and a warning indication. The latter may be an alert, some time prior to spoilage, e.g. a few days before the food product is spoiled, thereby providing the user an indication of the time remains until the food product losses its freshness and/or becomes spoiled.

In some embodiments, the detectable indication is a colored detectable indication. In some embodiments, the detectable indication comprises a change in color within the visual spectrum.

In some embodiments, the device further comprises a transparent window, thus enabling a vision of the detectable indication.

In some embodiments, the at least one indicator provides a detectable indication at temperatures below 30° C.

In some embodiments, the at least one indicator is provided in a concentration such that it changes its color in response to spoilage of the food sample. In some embodiments, the at least one indicator is provided in a concentration such that it enables bacterial reproduction. In some embodiments, the concentration of the at least one indicator is the ratio between the number of moles of the at least one indicator and the volume of the at least one chamber. In some embodiments, the concentration of the at least one indicator is the ratio between the number of moles of the at least one indicator and the volume of the food sample. It is to be understood that when the food sample is water-based, such as in the cases of milk and soft cheese products, an indicator may be mixed with a food sample, such that the total volume of the indicator-food sample solution remains substantially unchanged.

Thus, the devices and methods disclosed herein make use of pre-determined, specific, indicator(s) concentrations, thereby providing highly accurate color-based determination of food quality and thus, determination of the food spoilage time point.

In some embodiments, the at least one indicator is in a concentration within the range of $10^{-10}$ to $10^{-6}$ mol/ml. In some embodiments, the at least one indicator is provided in a concentration within the range of $2 \cdot 10^{-9}$ to $8 \cdot 10^{-7}$ mol/ml. In some embodiments, the at least one indicator is provided in a concentration within the range of $5 \cdot 10^{-9}$ to $1 \cdot 10^{-8}$ mol/ml. In some embodiments, the at least one indicator is provided in a concentration within the range of $2 \cdot 10^{-9}$ to $1 \cdot 10^{-8}$ mol/ml. In some embodiments, the at least one indicator is provided in a concentration within the range of $2 \cdot 10^{-8}$ to $1.5 \cdot 10^{-7}$ mol/ml. In some embodiments, the at least one indicator is provided in a concentration in the range of $1.2 \cdot 10^{-7}$ to $8 \cdot 10^{-7}$ mol/ml. In some embodiments, the at least one indicator is present at a concentration in the range of $2 \cdot 10^{-9}$ to $1.5 \cdot 10^{-8}$ mol/ml.

In some embodiments, the composition within the chamber comprises a plurality of indicators. In some embodiments, the composition comprises two indicators. In some embodiments, the composition comprises a plurality of pH indicators. In some embodiments, the composition comprises two pH indicators. In some embodiments, the composition comprises a plurality of bacterial indicators. In some embodiments, the composition comprises two bacterial indicators. In some embodiments, the composition comprises at least one pH indicator and at least one bacterial indicator. In some embodiments, the composition comprises one pH indicator and one bacterial indicator.

In some embodiments, the device comprises a plurality of chambers, each comprising a sample of said food product and a composition comprising at least one indicator.

In some embodiments, the at least one chamber further comprises at least one transition metal. In some embodiments, the at least one chamber comprises an indicator composition, a food sample and at least one transition metal. In some embodiments, the composition comprises at least one transition metal in addition to the at least one indicator. In some embodiments, the at least one transition metal is a non-toxic transition metal.

In some embodiments, the at least one transition metal is non-antibacterial transition metal, also referred hereinafter as a microbe-compatible transition metal.

The term "non-antibacterial" refers to materials which do not affect (e.g. are not significantly harmful) to microorganisms, such as, bacteria and fungi.

In some embodiments, the transition metal comprises one or more metals. In some embodiments, each of said one or more transition metals is selected from the group consisting of chromium, including Cr(III) and Cr(II), manganese, scandium, titanium, vanadium, iron, including Fe(II) and Fe(III), cobalt, nickel, copper, zinc and mixtures thereof. In some embodiments, the transition metal is selected from the group consisting of chromium, manganese, iron, copper and mixtures thereof. Each possibility is a separate embodiment of the invention.

In some embodiments, the transition metal has an oxidation state selected from II and III. In some embodiments, the transition metal comprises chromium. In some embodiments, the transition metal comprises Cr(III).

In some embodiments, the at least one indicator comprises an azo dye.

In some embodiments, the at least one indicator is selected from the group consisting of azo dyes, indole dyes, anthraquinone dyes, phenol dyes, cresol dyes, thymol dyes, xylenol dyes, phenazine dyes and any combinations thereof. In some embodiments, at least one indicator is selected from the group consisting of bromothymol blue, cresol red, phenol red, methyl red, indigo carmine, carmoisine red, tartrazine, bromocresol purple, alizarin, chlorophenol red, bromocresol green, bromophenol blue, bromoxylenol blue, neutral red and methyl orange. Each possibility is a separate embodiment of the invention.

Table 1 provides pH transition range in aqueous environment of several indicators.

TABLE 1

| Indicator | aqueous pH transition range | color change | CAS |
|---|---|---|---|
| Cresol Red | 7.2-8.8 | yellow to reddish purple | 1733-12-6 |
| Alizarin | 5.5-6.8 | yellow to violet | 72-48-0 |
| Bromocresol Purple | 5.2-6.8 | yellow to purple | 115-40-2 |
| Chlorophenol Red | 5.2-8.8 | yellow to red | 4430-20-0 |
| Nitrazine Yellow | 6.0-7.2 | yellow to bright blue | 5423-07-4 |
| Bromothymol Blue | 6.0-7.6 | yellow to blue | 34722-90-2 |
| Bromoxylenol Blue | 6.0-7.6 | yellow to blue | 40070-59-5 |
| Neutral Red | 6.8-8.0 | red to yellow | 553-24--9 |
| Phenol Red | 6.8-8.2 | yellow to red | 34487-61-1 |

In some embodiments, at least one indicator is selected from the group consisting of methyl red, methyl orange, bromophenol blue, indigo carmine, carmoisine red, tartrazine and bromocresol green. Each possibility is a separate embodiment of the invention.

In some embodiments, the at least one indicator is biocompatible. In some embodiments, the at least one indicator is non-antibacterial (microbe compatible). In some embodiments, the at least one indicator is devoid of quaternary amines and quaternary amine moieties. In some embodiments, the at least one indicator is devoid of quaternary ammonium salts and quaternary ammonium moieties.

Without wishing to be bound be any theory or mechanism, since the at least one indicator may be a bacterial indicator, namely, an indicator that is sensitive to the contents of bacteria, then the at least one indicator should be devoid of quaternary ammonium salts which are biocides. Accordingly, methylene blue may have an anti-bacterial activity and as such will not have the desired effect as an indicator for use in the device disclosed herein.

In some embodiments, the food sample is present in the chamber in an amount sufficient to cause a detectable indication by the at least one indicator. In some embodiments, the relative amounts of the food sample and the at least one indicator in the chamber are such that a detectable indication is caused by the at least one indicator.

In some embodiments, the chamber further comprises an aqueous solvent. In some embodiments, the aqueous solvent is an acidic aqueous solvent. In some embodiments, the aqueous solvent is a basic aqueous solvent. In some embodiments, the aqueous solvent and a portion of the food product form a food sample in the form of solution or a suspension. In some embodiments, the solution or suspension may have a pH within a range where the pH indicator is capable to provide a detectable indication corresponding to the freshness and/or spoilage of the food product. For example, when using a pH indicator which changes its color in response to a pH decrease below 7.5, an aqueous solvent having a pH of about 7.7-8 may be used in order to adjust the pH of food sample: aqueous solvent mixture to a pH higher than the indicator point of color change. As a result, an increase in acidity resulting from the spoilage of the food sample, will cause a pH drop below 7.5, and consequently, a color change.

In some embodiments, the composition comprising the at least one indicator comprises a solvent, such that the at least one indicator is dissolved therein. In some embodiments, the solvent is an aqueous solvent comprising water as the main component. In some embodiments, the solvent comprises water and ethanol. In some embodiments, the solvent comprises water and less than 0.5% ethanol. In some embodiments, the solvent comprises water and less than 0.05% ethanol. In some embodiments, the solvent comprises water and less than 0.01% ethanol.

In some embodiments, the food sample in the chamber is diluted to at least 0.1% relative to the food product.

In some embodiments, the sample is diluted such that the contents of insoluble substances within the food sample is at least 0.1% compared to the contents of insoluble substances within the food product. In some embodiments, the sample is diluted such that the contents of fatty acids and/or proteins in the food sample is at least 0.1% compared to the contents of fatty acids and/or proteins in the food product.

In some embodiments, the dilution does not affect the pH of the food sample, and it is identical to the pH of the food product prior to dilution.

In some embodiments, the pH of the food product is similar to the pH of the food sample.

In some embodiments, dilution may improve the visibility of the indication provided by the indicator. Thus, using an aqueous solvent, which has about the same pH of the food product, is not expected to influence the pH of the mixture of food sample within the chamber.

In some embodiments, the dilution does not affect the electrolyte contents of the food sample, and it is essentially similar to the electrolyte contents of the food product prior to dilution.

In some embodiments, dilution is performed at the time of adding a portion of the food product to the chamber, thereby creating a diluted food sample. Thus, a diluted food sample is obtained by adding a portion of the food product to the chamber, wherein the chamber includes a solvent in the appropriate amount which is required for forming the desired dilution.

In some embodiments, dilution is performed prior to adding the food sample to the chamber.

In some embodiments, there is provided a storage device comprising a food product, and a chamber, wherein the chamber comprises a sample of said food product, a composition comprising at least one indicator and at least two compartments, separated from one another by a membrane.

The term "membrane" as used herein, is interchangeable with the term "separator" and refers to a component that separates between compartments within the chamber(s) disclosed herein. The membrane may separate one or more components of the food sample (derived from the food product) from other components thereof. The membrane may act as a filter through which a portion of the food sample is transported from one compartment of the chamber to another, where the one compartment or the other includes the indicator composition.

In some embodiments, the membrane is a porous membrane.

In some embodiments, the membrane is impermeable to water insoluble colloidal materials. In some embodiments, the membrane is impermeable to water insoluble organic colloidal materials.

In some embodiments, the at least two compartments comprise a first compartment and a second compartment.

In some embodiments, the food sample may be initially added to the first compartment and allowed to diffuse through the membrane, such that, the second compartment receives a filtered portion of the food sample. Thus, in some embodiments, the first compartment comprises the food sample and the second compartment comprises a filtered portion of the food sample. In some embodiments, each compartment further comprises the composition comprising the at least one indicator. In some embodiments, the second compartment comprises the composition comprising the at least one indicator.

It is to be understood that the composition comprising the at least one indicator may be present in all compartments, and not necessarily only in the second compartment.

In some embodiments, the membrane is configured to separate the first compartment from the second compartment.

In some embodiments, the membrane is configured to filter the food sample, enabling transition, e.g. by active flow or spontaneous diffusion, of a portion of the food sample from the first compartment to the second compartment.

In some embodiments, the membrane is impermeable to at least some components of the food sample, thereby preventing, hindering or slowing down passage of said components from the first compartment to the second compartment. Generally, the membrane is intended to filter out (of the second compartment) at least a portion of the food sample, by preventing passage, through the membrane, from the first compartment to the second compartment. The portion of the food sample may include compounds that may mask, or otherwise interfere, viewing the color indication provided by the indicator. In some embodiments, the second compartment, which includes the at least one indicator, is visible to a user and the first compartment is invisible to the user (e.g. consumer). By filtering out compounds that cause turbidity and mask the vision of the indicator or the color change, the membrane allows a clearer detection of the freshness and/or spoilage of the food product. For example, compounds which may be filtered out from a sample of milk products include casein, a particulate compound usually comprising particles having an average particle size distribution within the range of about 100 nm.

The term "consumer" as used herein refers to any person, including, but not limited to, customers, manufacturers and distributers among others.

In some embodiments, the membrane is impermeable to water insoluble colloidal compounds. In some embodiments, the membrane is impermeable to fatty acids, and/or proteins. In some embodiments, the membrane is impermeable to molecules having a molecular weight of at least 500 gr/mol. In some embodiments, the membrane is impermeable to molecules having a molecular weight of at least 2,000 gr/mol.

In some embodiments, the membrane is porous with pores having an average size in a range of 0.01 microns to 1 micron. In some embodiments, the membrane is porous with pores having an average size in a range of 1 microns to 4 microns. In some embodiments, the membrane is porous with pores having an average size in a range of 4 microns to 10 microns. In some embodiments, the membrane is porous with pores having an average size in a range of 10 microns to 100 microns. In some embodiments, the membrane is porous with pores having an average size of at least 100 nanometers.

In some embodiments, the membrane is a porous membrane having a thickness from about 10 microns to about 600 microns. In some embodiments, the membrane is a porous membrane having a thickness from about 10 microns to about 200 microns. In some embodiments, the porous membrane has a thickness from about 25 microns to about 100 microns. In some embodiments, the porous membrane has a thickness of at most 100 microns. In some embodiments, the porous membrane has a thickness of at least 25 microns.

In some embodiments, the porous membrane has a porosity of from about 10 percent to about 80 percent. In some embodiments, the porous membrane has a porosity of from about 30 percent to about 60 percent. In some embodiments, the porous membrane has a porosity of from about 40 percent to about 50 percent.

As used herein, the term "about" refers to a range of values ±20%, or ±10% of a specified value. For example, the phrase "having a thickness from about 10 microns to about 600 microns" includes ±20% of both 10 microns and 600 microns.

In some embodiments, the membrane is made of a material selected from the group consisting of metals, polymers and ceramics. In some embodiments, the membrane is made of a polymer. In some embodiments, the polymer is selected from the group consisting of polyethylene, polypropylene, polytetrafluoroethylene, cellulose acetate, nitrocellulose, polysulfone, polyether sulfone, polyacrilonitrile, polyamide, polyimide, polyvinylidene fluoride, polyvinylchloride, and combinations thereof. Each possibility is a separate embodiment of the invention. In some embodiments, the polymer comprises polypropylene.

In some embodiments, the membrane is an ion exchange membrane. In some embodiments, the membrane is a proton exchange membrane or an alkaline anion exchange membrane.

In some embodiments, the device may include a plurality of chambers, each comprising a sample of said food product and a composition comprising at least one indicator. It is to be understood that each of the plurality of chambers may be similar to other chambers of the plurality of chambers, or it may be different. For example, the plurality of chambers may include chamber(s) comprising a diluted food sample, and/or chamber(s) comprising at least two compartments, separated from one another by a membrane, and/or chamber(s) comprising bacterial indicators, as disclosed herein.

In some embodiments there is provided a storage device comprising a food product, and a chamber, wherein said chamber comprising a sample of said food product and a composition comprising at least one bacterial indicator.

In some embodiments, the indicator provide an indication as a results of reduction of an internal double bond.

In some embodiments, at least one bacterial indicator is selected from the group consisting of azo dyes, indole dyes, cresol dyes and any combination thereof. Each possibility is a separate embodiment of the invention.

In some embodiments the at least one bacterial indicator is selected from the group consisting of methyl red, methyl orange, bromophenol blue, indigo carmine, carmoisine red, tartrazine, bromocresol green and combinations thereof.

In some embodiments, the at least one bacterial indicator provides an indication upon reduction of an internal double bond selected from an N=N bond and a C=C bond. In some embodiments, the reduction is an irreversible reduction.

It should be noted that the use of indigo carmine, carmoisine red and tartrazine as food quality indicators is presented herein for the first time.

Thus, in some embodiments, the at least one bacterial indicator is selected from the group consisting of indigo carmine, carmoisine red and tartrazine. Each possibility is a separate embodiment of the invention.

In some embodiments there is provided a food quality indicator selected from indigo carmine, tartrazine, carmoisine red and combinations thereof.

In some embodiments, there is provided a food quality indicator consisting of indigo carmine.

In some embodiments there is provided a food quality indicator comprising indigo carmine. In some embodiments, there is provided a food quality indicator consisting of indigo carmine. In some embodiments, there is provided use of indigo carmine for detecting microorganisms in a food product. In some embodiments, the microorganisms comprise bacteria. In some embodiments, the use of indigo carmine is for detecting the presence of bacteria, or compounds related to bacteria, in food products. In some embodiments, the use of indigo carmine is for detecting spoilage of food products.

In some embodiments, there is provided a food quality indicator consisting of methyl orange.

In some embodiments there is provided a food quality indicator comprising methyl orange. In some embodiments, there is provided a food quality indicator consisting of methyl orange. In some embodiments, there is provided use of methyl orange for detecting microorganisms in a food product. In some embodiments, the microorganisms comprise bacteria. In some embodiments, the use of methyl orange is for detecting the presence of bacteria, or compounds related to bacteria, in food products. In some embodiments, the use of methyl orange is for detecting spoilage of food products. Surprisingly, the indication provided by methyl orange in the devices and methods disclosed herein is not limited to it known range of 3.1 to 4.4 pH. Rather, the indication provided by methyl orange in the devices and methods disclosed herein is effective at higher pH values of about 6 to 7.

In some embodiments, there is provided a food quality indicator consisting of methyl red.

In some embodiments there is provided a food quality indicator comprising methyl red. In some embodiments, there is provided a food quality indicator consisting of methyl red. In some embodiments, there is provided use of methyl red for detecting microorganisms in a food product. In some embodiments, the microorganisms comprise bacteria. In some embodiments, the use of methyl red is for detecting the presence of bacteria, or compounds related to bacteria, in food products. In some embodiments, the use of methyl red is for detecting spoilage of food products. Surprisingly, the indication provided by methyl red in the devices and methods disclosed herein is not limited to it known range of 4.4 to 6.2 pH. Rather, the indication provided by methyl red in the devices and methods disclosed herein is effective at higher pH values of above 6.2.

In some embodiments, there is provided a food quality indicator consisting bromophenol blue.

In some embodiments there is provided a food quality indicator comprising bromophenol blue. In some embodiments, there is provided a food quality indicator consisting of bromophenol blue. In some embodiments, there is provided use of bromophenol blue for detecting microorganisms in a food product. In some embodiments, the microorganisms comprise bacteria. In some embodiments, the use of bromophenol blue is for detecting the presence of bacteria, or compounds related to bacteria, in food products. In some embodiments, the use of bromophenol blue is for detecting spoilage of food products. Surprisingly, the indication provided by bromophenol blue in the devices and methods disclosed herein is not limited to it known range of 3.0 to 4.6 pH. Rather, the indication provided by bromophenol blue in the devices and methods disclosed herein is effective at higher pH values of about 6 to 7.

In some embodiments there is provided a food quality indicator comprising tartrazine. In some embodiments, there is provided a food quality indicator consisting of tartrazine. In some embodiments, there is provided use of tartrazine for detecting microorganisms in a food product. In some embodiments, the microorganisms comprise bacteria. In some embodiments, the use of tartrazine is for detecting the presence of bacteria, or compounds related to bacteria, in food products. In some embodiments, the use of tartrazine is for detecting spoilage of food products.

In some embodiments, there is provided a food quality indicator comprising carmoisine red. In some embodiments, there is provided a food quality indicator consisting of carmoisine red. In some embodiments, there is provide use of carmoisine red for detecting microorganisms in a food product. In some embodiments, the microorganisms comprise bacteria. In some embodiments, the use of carmoisine red is for detecting the presence of bacteria, or compounds related to bacteria, in food products. In some embodiments, the use of carmoisine red is for detecting spoilage of food products.

Generally, carmoisine red (also known as azorubine, carmoisine, Food Red 3, Azorubin S, Brillant carmoisin O, Acid Red 14, or C.I. 14720) is a synthetic red food dye from the azo dye group. It is known for use in externally applied drugs and cosmetics. Thus, carmoisine red is disclosed herein for the first time, as a food quality indicator.

In some embodiments, there is provided a food quality indicator comprising bromocresol green. In some embodiments, there is provided a food quality indicator consisting of bromocresol green. In some embodiments, there is provide use of bromocresol green for detecting microorganisms in a food product. In some embodiments, the microorganisms comprise bacteria. In some embodiments, the use of bromocresol green is for detecting the presence of bacteria, or compounds related to bacteria, in food products. In some embodiments, the use of bromocresol green is for detecting spoilage of food products. Surprisingly, the indication provided by bromocresol green in the devices and methods disclosed herein is not limited to it known range of 3.8 to 5.4 pH. Rather, the indication provided by bromocresol green in the devices and methods disclosed herein is effective at higher pH values of about 6 to 7.

Without wishing to be bound by any theory or mechanism, carmoisine red loses its red color in response to a reduction of its N=N azo bond, which leads to a break in the conjugated chain, as a result of a bacterial activity. Alternatively, the loss in color may be attributed to an intramolecular proton shift between the sulfate and hydroxyl groups of the carmoisine red molecule.

The at least one bacterial indicator provides an indication as a results of irreversible reduction of an internal double bond selected from an N=N bond and a C=C bond.

In some embodiments, the bacterial indicator comprises an azo dye.

In some embodiments, the at least one bacterial indicator comprises a plurality of indicators. In some embodiments, the composition comprising at least one bacterial indicator further comprises a composition comprising a transition metal. In some embodiments, the transition metal may be a salt of the transition metal comprising the transition metal and a counter ion. In some embodiments, the combination of bacterial indicator and the composition comprising a transition metal is not anti-bacterial.

In some embodiments, the transition metal is selected from the group consisting of chromium, manganese, scandium, titanium, vanadium, iron, cobalt, nickel, copper, zinc and mixtures thereof. In some embodiments, the transition metal is selected from the group consisting of chromium, manganese, iron, copper and mixtures thereof. In some embodiments the transition metal comprises chromium. In some embodiments, the transition metal comprises Cr(III).

In some embodiments, a spoilage of the food product results in an increase in acidity and in bacterial population.

In some embodiments, the food product comprises a dairy product. In some embodiments, the dairy product is selected from the group consisting of milk, cheese, flavored milk, sour cream, yogurt, cream, smoothies, kefir, milkshake, ice cream, butter and combinations thereof. In some embodiments, the food product comprises milk. In some embodiments, the dairy product comprises cheese. In some embodiments, the dairy product comprises cottage cheese. In some embodiments, the dairy product comprises yogurt.

In some embodiments, the food product comprises a meat product. In some embodiments, the meat product comprises poultry meat.

In some embodiments, the detection occurs after a frozen food products has been defrosted and remains when said food product is frozen, again. Thus, the devices and methods disclosed herein are useful for detecting food spoilage even in frozen food products.

The following examples are presented in order to more fully illustrate some embodiments of the invention. They should, in no way be construed, however, as limiting the broad scope of the invention.

EXAMPLES

Example 1

Correlation Between Milk Storage Temperature and pH

The pH values of milk samples were monitored for up to 345 hours, for a milk sample stored at 4° C. and for a milk sample stored at 18° C. FIG. 1 shows the pH over time of the milk sample stored 4° C. (triangles) and the milk sample stored 18° C. (squares). As freshness decreases over time, the pH values respectively decrease. It can be seen that the pH measurements of the milk sample stored at 18° C. sharply decreased after 95 h, indicating a rapid spoilage, while the milk sample stored at 4° C. remained fresh for a longer period, and the spoilage was slower.

Example 2A

Correlation Between the Rate of Spoilage of Small and Large Milk Samples

Figure 2A:
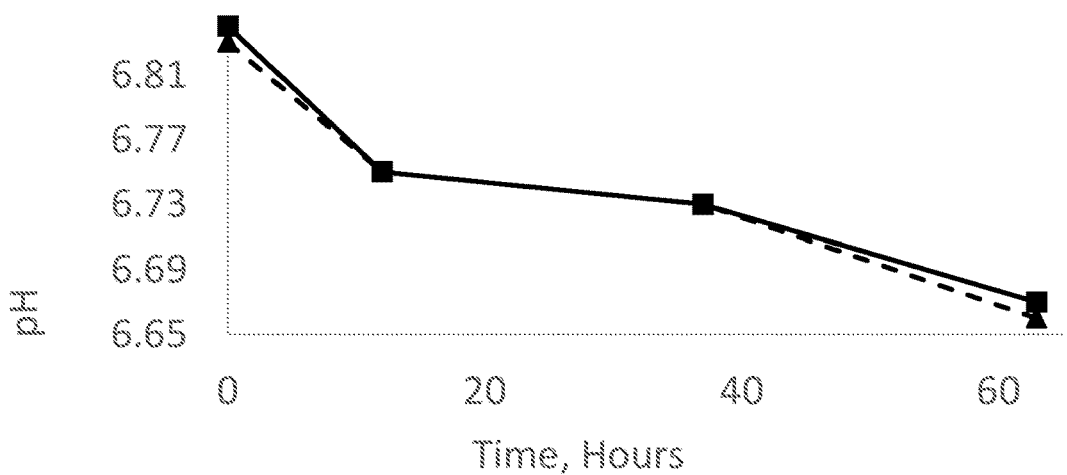
FIG. 2A is a graph showing the pH of milk samples vs. time for small milk samples (2-5 ml; triangles) and large milk samples (50-100 ml; squares) stored at room temperature.

The pH values of small (2-5 ml) and large (50-100 ml) milk samples were monitored for up to 60 hours, while being stored at room temperature, in order to compare their rates of spoilage. FIG. 2A shows the pH over time of the small milk samples (triangles) and the large milk samples (squares). As freshness decreased over time, the trend of decreasing pH values was witnessed in both large and small milk samples. More importantly, it was witnessed that both large and small milk samples are losing freshness and becoming spoiled at substantially the same rate. The results thus indicate that the rate of spoilage of a small food sample (such as the food sample in the at least one chamber) and a large food sample (e.g. the food product in the device from which the food sample has been derived) are similar.

Example 2B

Figure 2B:
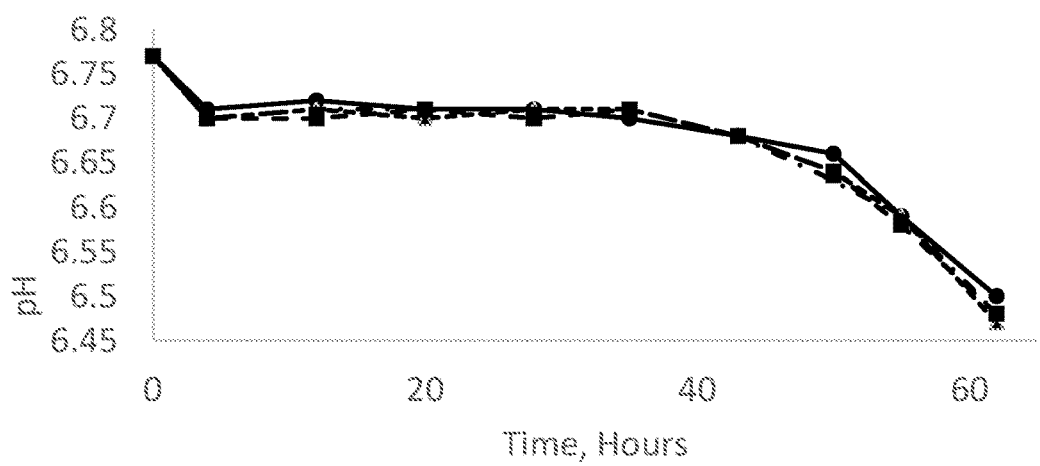
FIG. 2B is a graph showing the pH of milk samples vs. time for 0.5 ml milk samples (dashed line, squares), 1.5 ml milk samples set A (dashed line, triangles), 1.5 ml milk samples set B (dashed line, no marker) and 50 ml milk samples (solid line, circles) stored at 18-20° C.

Correlation Between the Rate of Spoilage of Small and Large Samples Containing Milk and Indigo Carmine In order to determine whether an external indicator indigo carmine has an influence over the measured pH the pH values of small (0.5 ml), medium (1.5 ml) and large (50 ml) milk samples were monitored. The samples were prepared by combining 500 ml row milk and 6 gr of 0.02% indigo carmine aqueous solution at 4° C. After 1 h in 4° C. the mixture was divided into four 50 ml samples, two sets of three 1.5 ml samples and fifteen 0.5 ml samples. All the samples were measured to have pH=6.77. The pH values of the samples were monitored for up to 60 hours, while being stored at 18-20° C., in order to compare their rates of spoilage. FIG. 2B shows the pH over time of the 0.5 ml milk samples (dashed line, squares), 1.5 ml milk samples set A (dashed line, triangles), 1.5 ml milk samples set B (dashed line, no marker) and 50 ml milk samples (solid line, circles). As freshness decreased over time, the trend of decreasing pH values was witnessed in both large, medium and small milk samples. More importantly, it was witnessed that both large and small milk samples are losing freshness and becoming spoiled at substantially the same rate. Specifically, the correlation coefficients (calculated using Microsoft Excel) between the graph lines were 0.993 or higher. The results thus indicate that the rate of spoilage of a small food sample (such as the food sample in the at least one chamber) and a large food sample (e.g. the food product in the device from which the food sample has been derived) are similar.

Example 3

Quality Indication of Whole Milk Using Bromothymol Blue

Samples of non-diluted fresh (pH=6.84) and spoiled (pH=6.52) milk were separately inserted into two Eppendorf tubes. To each sample bromothymol blue pH indicator was added and the resulting colors were visually evaluated. Generally, bromothymol blue is a pH sensitive indicator, which changes its color from blue above pH 7.6 to yellow below pH 6.0.

Figure 3B:
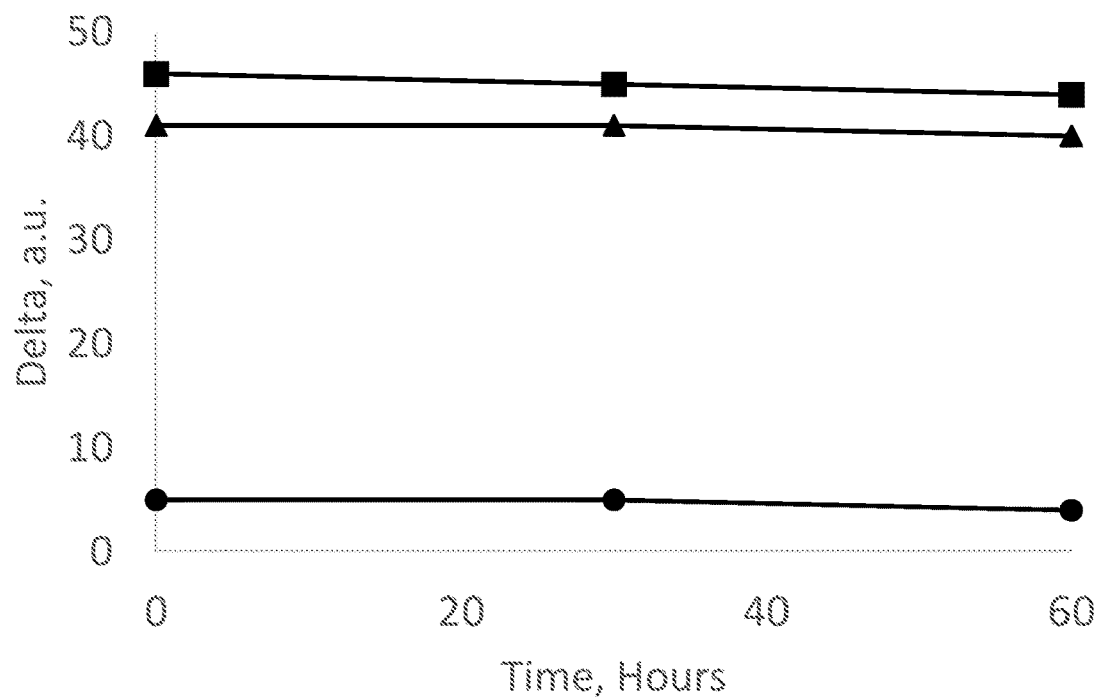
FIG. 3B is a graph showing an image analysis in the RGB base in Red-Blue (squares) Red-Green (circles) and Green-Blue (triangles) vs. time of a whole milk sample stored in an Eppendorf tube with bromothymol blue for 60 h 18° C.
Figure 3A:
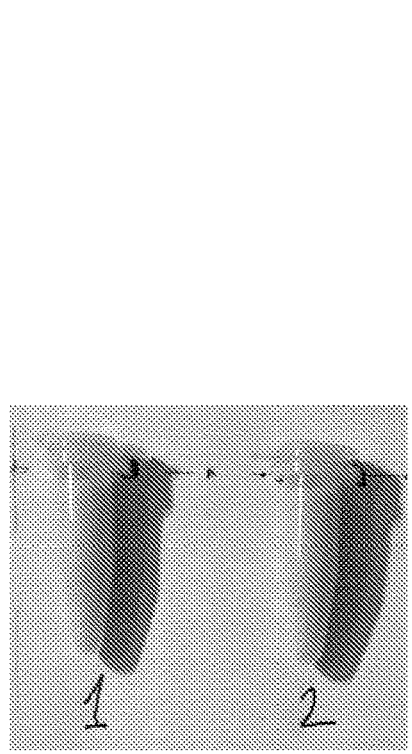
FIG. 3A is a photograph of a milk sample stored in an Eppendorf tube with bromothymol blue, when fresh (left) and after becoming spoiled (right).

FIG. 3A is showing a photograph of the fresh milk sample with bromothymol blue (left) and a photograph of the spoiled milk sample with bromothymol blue (right). There is no visually discernible change in color between the two samples, as it seems that the natural turbidity of the milk samples masks the color change provided by the indicator upon change of the milk quality from fresh to spoiled.

Color changes (RGB scale, based on reflection, the detection is based on light detected from the chamber) of a sample of fresh milk with bromothymol blue were monitored for 60 h in order to learn whether a visible change is observed during the spoilage process. The result are given in FIG. 3B, which show that in Red-Blue (squares) Red-Green (circles) and Green-Blue (triangles) color ranges there is no significant occurrence of color change upon the spoilage of the milk samples. This indicates again that bromothymol blue pH indicator is not suitable for spoilage detection in whole (unfiltered and undiluted) milk samples.

Example 4

Quality Indication of Whole Milk Using Bromothymol Blue in a Two-Compartment Tube As bromothymol blue failed to distinguish fresh milk samples from spoiled ones, due to the turbidity of the milk, a similar experiment was carried out using Eppendorf tubes in which membranes were assembled, dividing each tube into two compartments: bottom and top. A polypropylene film of 25-100 μm thickness was used as the separating membrane. The pore size of the separating membrane ranges from hundreds nanometers to several microns. The tube was constructed such that the milk samples are separated from the indicator solution by the separating membrane. Thus, the masking factors in the milk samples, e.g. concentrated colloid of proteins, fats and hydrocarbons, were substantially separated from the indicator solution, which remained substantially clear at the bottom compartment.

Figure 4:
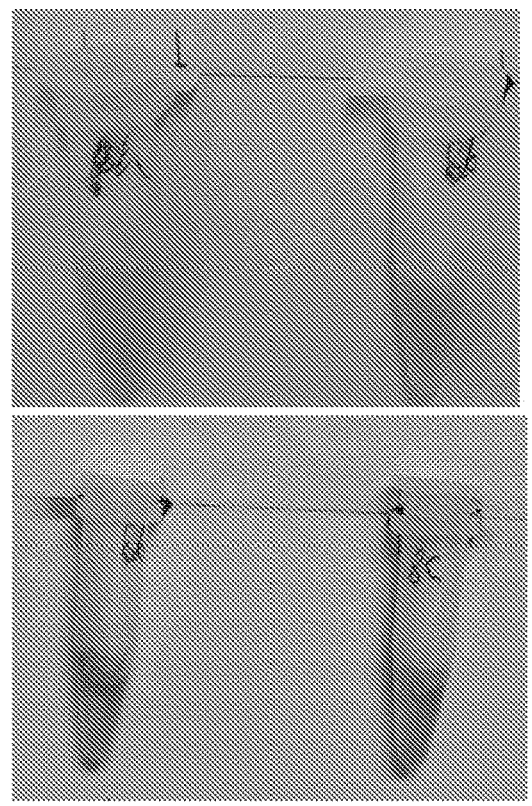
FIG. 4 is showing a milk sample stored in two Eppendorf tubes, each having two compartments, separated from one another by a membrane, and further containing a composition comprising bromothymol blue, when fresh (top photograph) and after becoming spoiled (bottom photograph).

FIG. 4 presents photographs of milk samples placed in Eppendorf tubes, each having two compartments, top and bottom, separated from one another by a separating membrane. The photographs show fresh samples (top left and top right photographs) and spoiled samples (bottom left and bottom right photographs).

There is a visually distinct change in color from yellow in the Eppendorf tubes having fresh milk samples to green in the Eppendorf tubes having spoiled milk samples. The color change is visible at the bottom compartment, which includes filtered milk. The results demonstrate the feasibility of the method in distinguishing fresh from spoiled food products, through eliminating the food masking factors by employing separating membrane.

Figure 5:
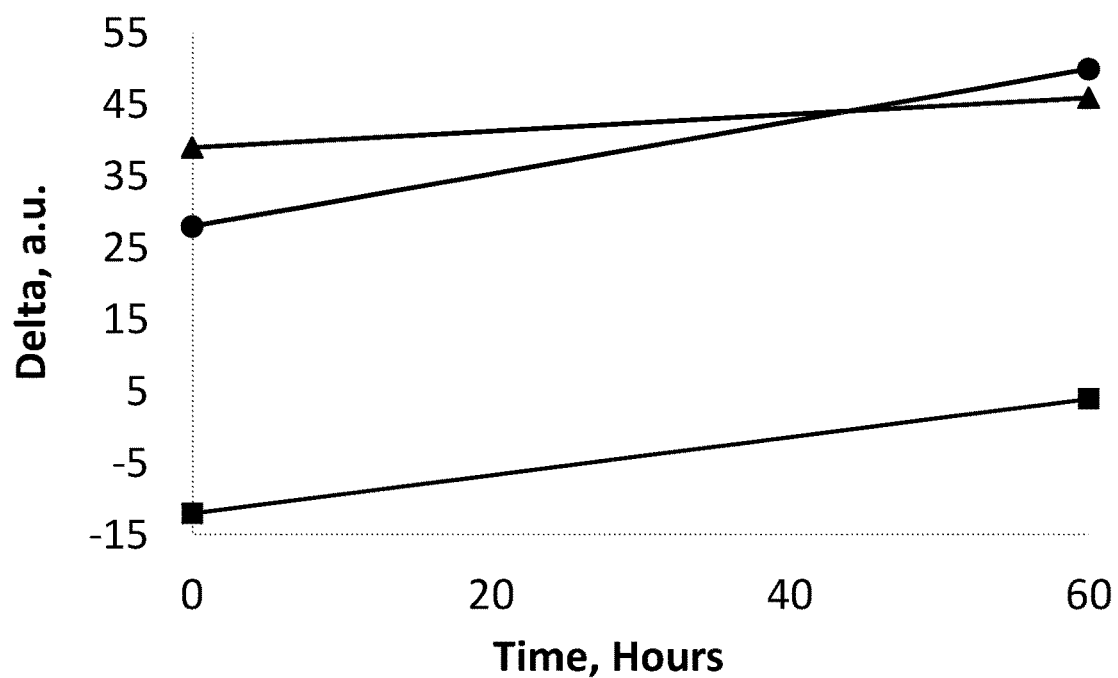
FIG. 5 is an image analysis in the RGB base in Red-Blue (circles) Red-Green (squares) and Green-Blue (triangles) corresponding to FIG. 4.

In addition, color changes (RGB scale) of the above samples of whole fresh milk in a membrane-separated two-compartment Eppendorf with bromothymol blue indicator, were monitored for 60 h in order to quantitate the color change observed during the spoilage process. The result are given in FIG. 5, which shows that in both Red-Blue (circles), Green-Blue (triangles) and Red-Green (squares) color ranges there was a significant color change upon spoilage of the milk samples. This change indicates again that a two-compartment system with an indicator is suitable for detection or monitoring spoilage of food products.

Example 5

Quality Indication of Whole Milk Using Cresol Red in a Two-Compartment Tube

A similar experiment was carried out using $5 \cdot 10^{-9}$-$1 \cdot 10^{-8}$ mol/ml cresol red as an indicator for milk spoilage in Eppendorf tubes in which separating membranes were assembled. Generally, cresol red is a pH sensitive indicator, which changes its color from red above pH 8.8 to yellow below pH 7.2. The tubes were divided into two compartments by polypropylene thin separating membrane (25-100 μm thickness). The pore size of such membranes ranges from hundreds nanometers to several microns. The tube was constructed such that a portion of the milk samples are diffuse through the membrane, to the bottom compartment. That portion, which was separated from the masking factors in the milk samples, e.g. concentrated colloid of proteins, fats and hydrocarbons, remained substantially clear.

Figure 6:
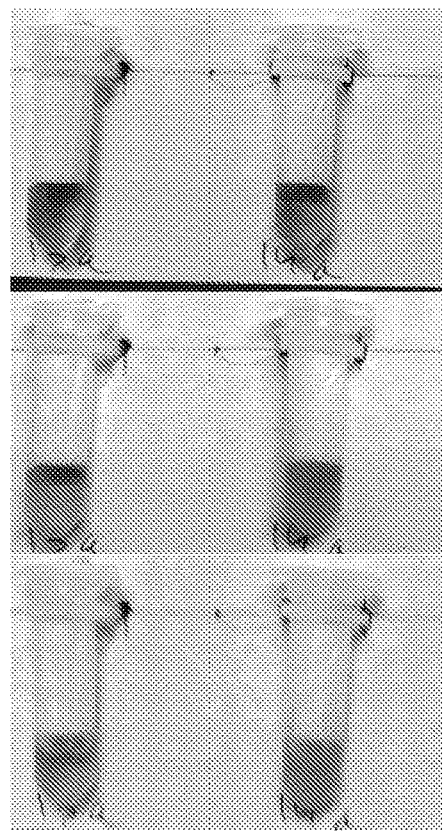
FIG. 6 is showing a milk sample stored in two Eppendorf tubes, each having two compartments, separated from one another by a membrane, and further containing a solution comprising cresol red, when fresh (top photograph), when not fresh but not yet spoiled (i.e. edible, in a transition state; middle photograph) and when becoming spoiled (bottom photograph).

FIG. 6 is showing photographs of Eppendorfs divided into two compartments, by a separating membrane, containing cresol red solution and fresh milk (top left and top right), or milk in a transition phase (i.e. after some storage time) (middle left and middle right) or spoiled milk (bottom left and bottom right).

Here too, there was a visually distinct change in color from red, in the fresh milk samples, to yellow in the spoiled or completely spoiled milk samples, showing the feasibility of the method to distinguish fresh from spoiled food products, through eliminating the food masking factors from the reaction with the indicator.

The indication of a sample that is not spoiled, but is not considered fresh (as it has been under storage for a certain amount of time) may be referred to as a transition state during which the milk is edible and there are no indications of spoilage, namely, no bad smell or phase separation (even when the milk sample is mixed with hot water). Typically, the transition stage is characterized by a small decrease in pH, e.g. the pH may change from 6.84 to 6.86, or from 6.72 to 6.76. In the current example, the pH change from fresh to transition, was within the following ranges of from 6.82 to 6.84 or from 6.69 to 6.70 for most samples at room temperature, but it is still absolutely acceptable.

Figure 7:
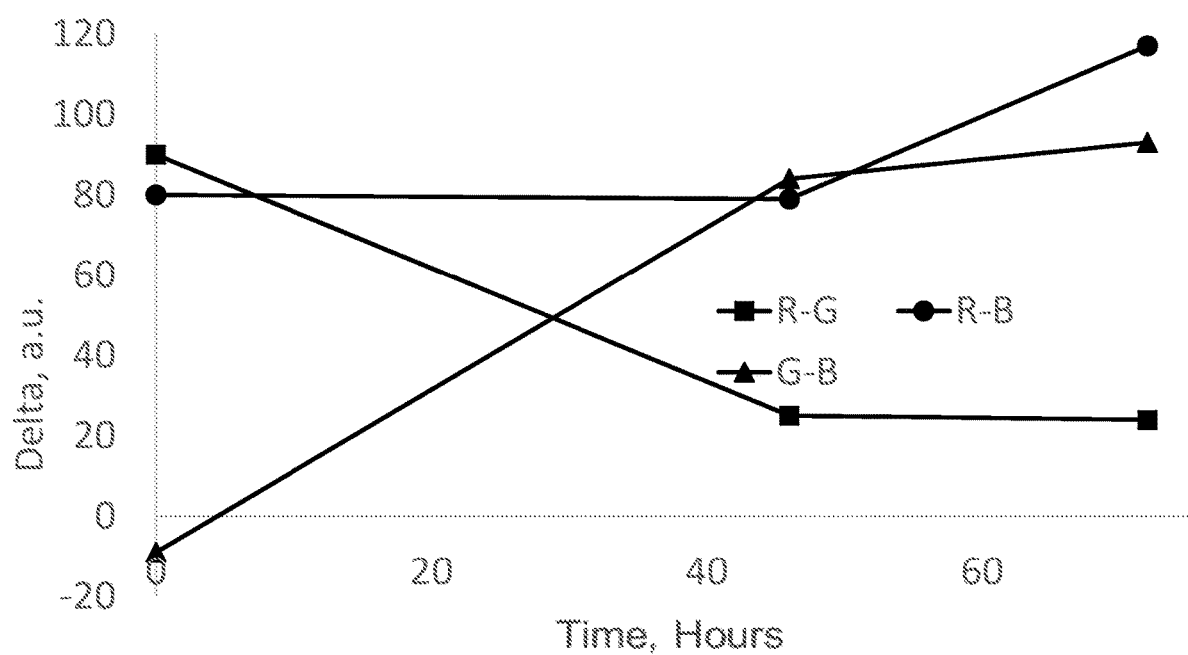
FIG. 7 is an image analysis in the RGB base in Red-Blue (circles) Red-Green (squares) and Green-Blue (triangles) corresponding to FIG. 6.

In addition, color changes (RGB scale) of the above samples of whole fresh milk in a membrane-separated two-compartment Eppendorf with cresol red indicator, were monitored for 70 h in order to quantitate the color change observed during the spoilage process. The result are given in FIG. 7, which shows that in both Red-Blue (circles), Green-Blue (triangles) and Red-Green (squares) color ranges there was a significant color change upon spoilage of the milk samples. This change indicates again that a two-compartment system with an indicator is suitable for detection or monitoring spoilage of food products.

Example 6

Correlation Between Milk Dilution and Transparency

Figure 8A:
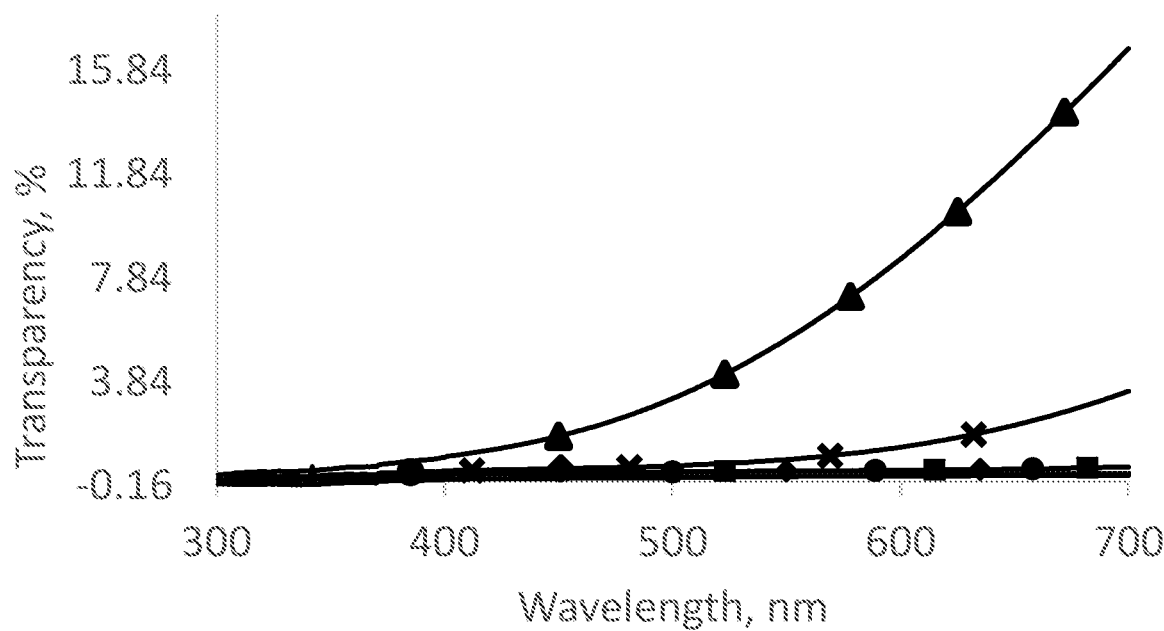
FIG. 8A is a graph showing the transparency percentage of milk samples in wavelengths ranging from 300 to 700 nm for whole milk (squares), 2-fold diluted milk (diamonds), 5-fold diluted milk (circles), 10-fold diluted milk (X) and 20-fold diluted milk (triangles) samples.
Figure 8B:
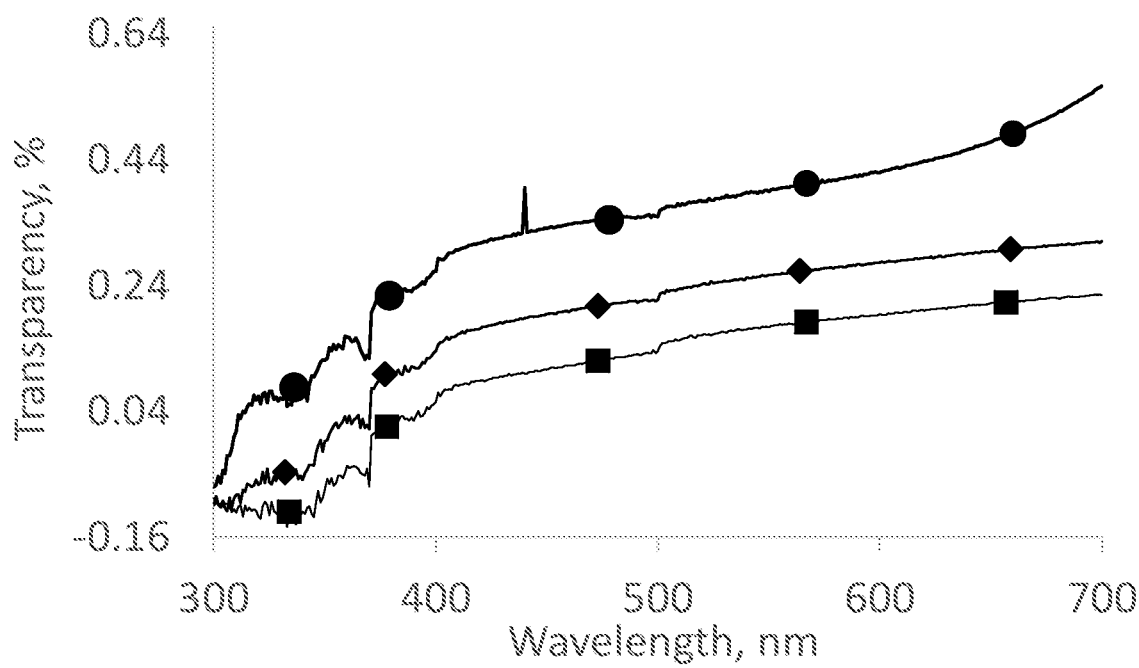
FIG. 8B is a portion of FIG. 8A, corresponding to wavelengths ranging from 300 to 700 nm for whole milk (squares), 2-fold diluted milk (diamonds) and 5-fold diluted milk (circles).

Another approach for eliminating the masking property of certain components in milk from the visual detection of color changes as provided by pH indicators was to use samples of diluted milk. In order to evaluate the feasibility of the dilution approach, the transparencies of milk samples in the region of 300 to 700 nm were measured for a sample of whole milk and for samples of milk mixed with water resulting with 2- to 20-fold dilutions. FIG. 8A shows the transparency (in percentage) of milk samples in wavelengths ranging from 300 to 700 nm for whole milk (squares), 2-fold diluted milk (diamonds), 5-fold diluted milk (circles), 10-fold diluted milk (X) and 20-fold diluted milk (triangles). FIG. 8B is an enlargement of FIG. 8A in the range of −0.15% and 0.6% transparency, in which the trend lines of whole milk (squares), 2-fold diluted milk (diamonds) and 5-fold diluted milk (circles) are sufficiently separate from one another. The result indicate that, while samples of milk diluted up to 5-fold with water, showed no substantial increase in transparency and remained turbid, samples of milk diluted by 10 to 20 fold, showed significant increase in transparency, most prominent in wavelengths of 600 to 700 nm.

Example 7

Correlation Between pH of Diluted Milk and Whole Milk During Spoilage

Figure 9:
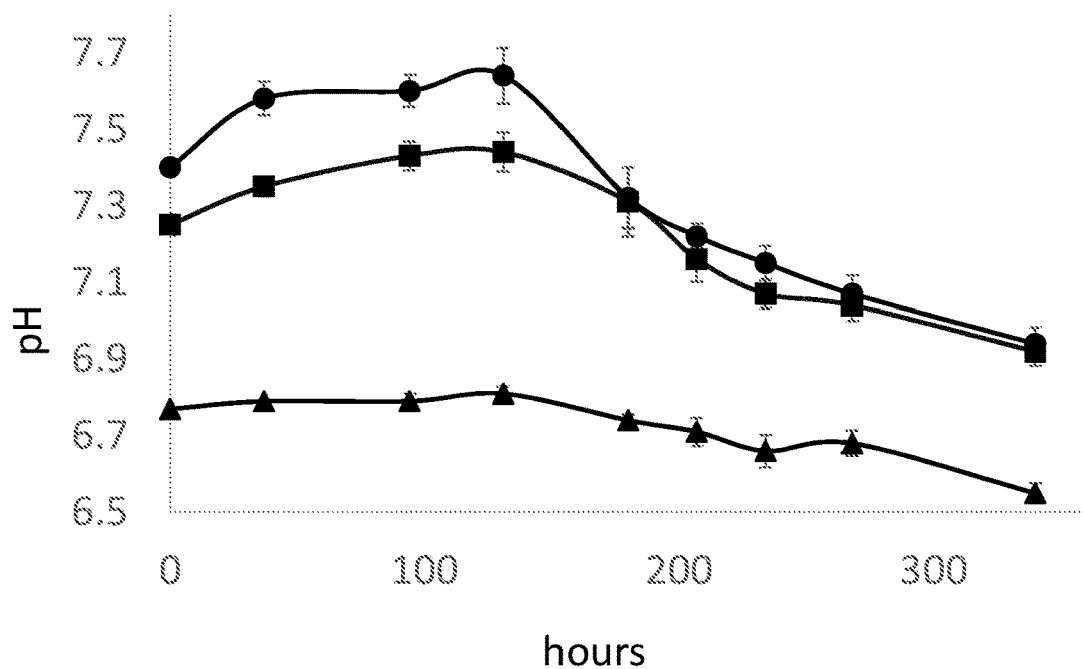
FIG. 9 is a graph depicting pH vs. storage time of milk samples stored 4° C.: whole milk sample (triangles), 10-fold diluted milk sample (squares) 20-fold diluted milk sample (circles).

The effect of dilution on detection of spoilage was evaluated. The pH values of milk were monitored for 345 hours in whole milk samples and in diluted milk samples (10-fold and 20-fold) stored at 4° C. Dilution was obtained with a slightly basic aqueous solution having pH=7.8. FIG. 9 shows changes in pH over time of milk samples stored 4° C.: whole milk sample (triangles), 10-fold diluted milk sample (squares) and 20-fold diluted milk sample (circles). As freshness decreases over time, the pH values respectively decrease for both whole and diluted milk samples. Moreover, a good correlation between the pH drop in the whole milk sample and the diluted milk samples was observed, with calculated correlation values of 0.947 and 0.943 between the pH profile of whole milk and the pH profiles of 10-fold and 20-fold diluted milk, respectively. The results demonstrate the feasibility of the dilution approach in distinguishing fresh from spoiled food products, through eliminating the food masking factors.

Example 8

Quality Indication of Diluted Milk Using Methyl Red

Figure 10A:
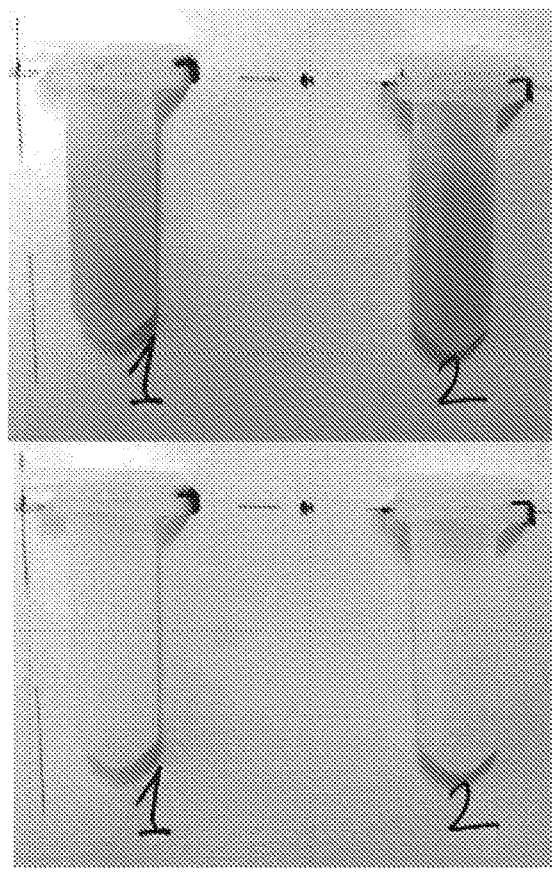
FIG. 10A is showing a 1:10 diluted milk samples stored in an Eppendorf tube comprising methyl red indicator solution when fresh (top photograph) and after becoming spoiled (bottom photograph).

As most pH indicators fail to distinguish fresh milk samples from spoiled ones, due to the milk turbidity, 1:10 dilutions of milk samples were tested, with are $2 \cdot 10^{-9}$-$10^{-8}$ mol/ml methyl red as a pH indicator. Typically, methyl red changes from red below pH 4.4 to yellow above pH 6.2. The experimental set up included the use of an aqueous solution for dilution, adjusting the initial pH to 7.16. Since the masking factors in the milk samples, e.g. concentrated colloid of proteins, fatty acids and hydrocarbons, were diluted, the color indication provided by indicator was visible and clear. FIG. 10A is showing photographs of diluted (1:10) samples of fresh (top left and top right) and spoiled milk (bottom left and bottom right) mixed with methyl red indicator solution.

There was a visually distinct change in color from yellow in fresh milk samples to white in spoiled milk samples, indicating the feasibility of the dilution method in distinguishing fresh from spoiled food products. It is noted that in the case of methyl red indicator, the color change may result from reduction of the N=N bond, rather than from a protonation/deprotonation process. The reduction of the N=N bond is known to be caused by bacterial action, therefore the disappearance of the yellow color from the methyl red solution indicated spoilage of the milk due to the bacterial presence and activity, rather than through a pH change.

Figure 10B:
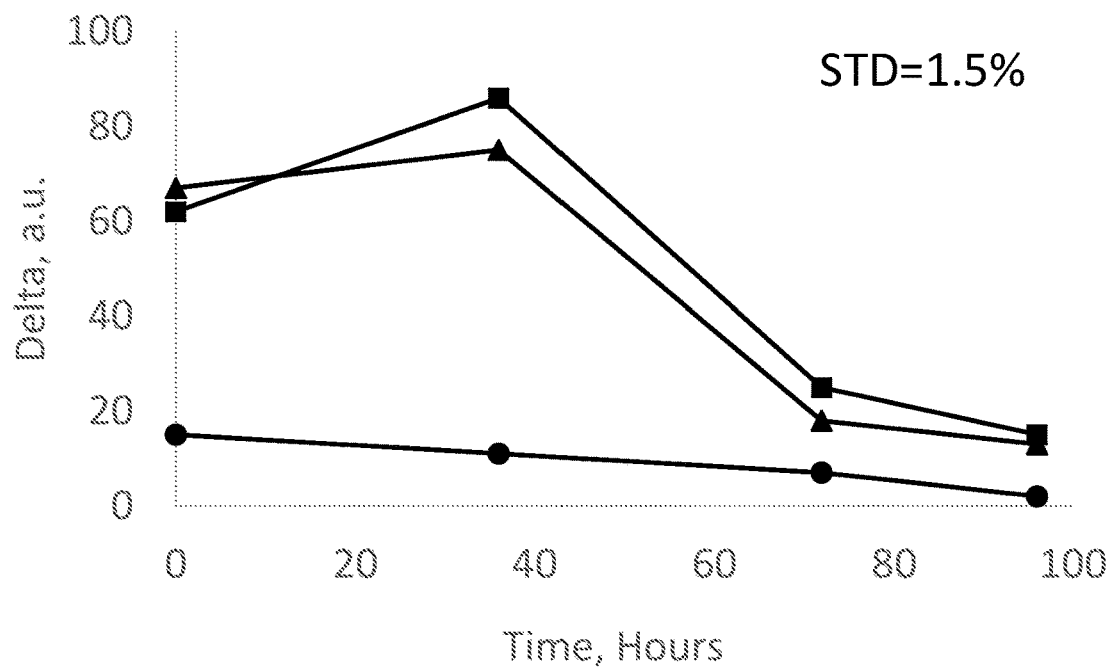
FIG. 10B is a graph showing an image analysis in the RGB base in Red-Blue (squares) Red-Green (circles) and Green-Blue (triangles), vs. time of a 1:10 diluted milk sample stored in an Eppendorf tube with methyl red for 95 h.

In addition, color changes (RGB scale) of the above samples of diluted (1:10) fresh milk with methyl red were monitored for 95 h in order to quantitate the color change observed during the spoilage process. The result are given in FIG. 10B, which show that in both Red-Blue (squares), Green-Blue (triangles) and Red-Green (circles) color ranges there was a significant color change upon spoilage of the milk samples. This change indicates again that methyl red pH indicator is suitable for detection or monitoring spoilage of diluted food products.

Example 9A

Quality Indication of Whole Milk Using Bacterial Indicators

As seen in Example 3 most pH indicators fail to distinguish fresh milk samples from spoiled ones, unless diluted or filtered through a membrane, due to the turbidity of the milk. On the other hand, Example 8 indicated that other than pH sensing by pH indicators, a direct monitoring of milk spoilage can be achieved through sensing the growth of bacterial population. It was further shown that methyl red, which loses its yellow color in the presence of bacteria, may be used as an appropriate quality and freshness indicator in diluted food products although it does not function as a pH indicator in a pH relevant to milk spoilage suggesting using indications based on the changes in bacterial presence or in the amount of compounds related to the presence of bacteria. As a result, experiments were carried out with whole milk using indicators which are sensitive to the presence of bacteria, which in its turn indicate the spoilage of milk.

Figure 11A:
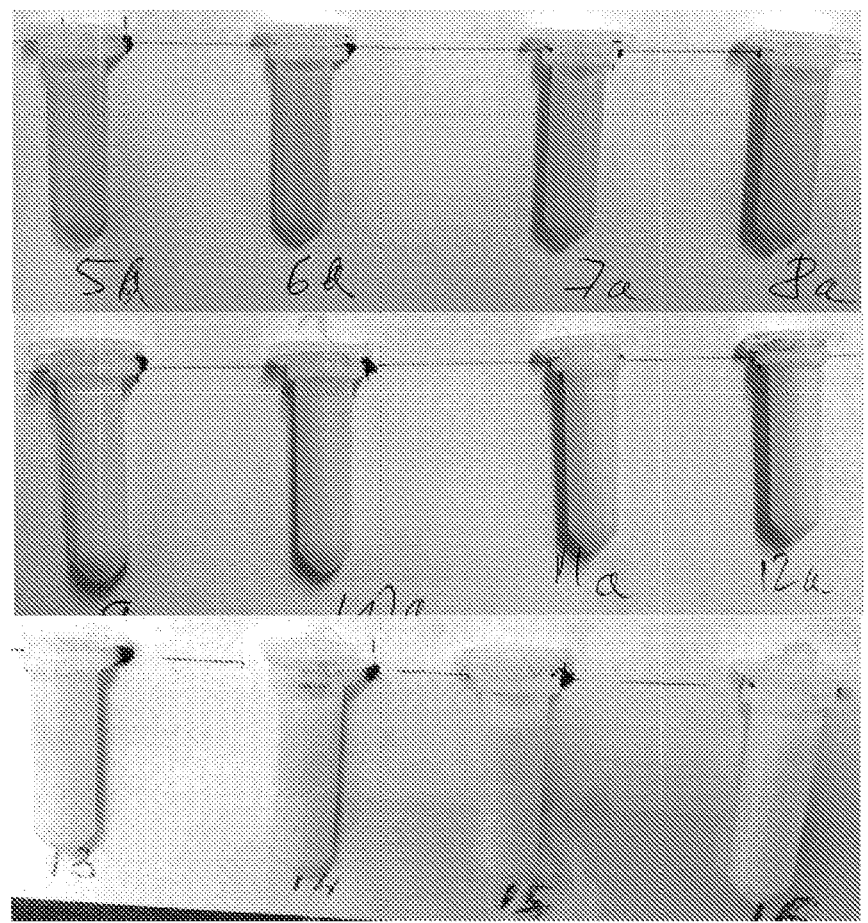
FIG. 11A is showing a whole milk sample stored in four Eppendorf tubes each comprising a methyl red solution, when fresh (top photograph), during a transition phase (middle photograph) and after becoming spoiled (bottom photograph).

An experiment similar to the experiments presented in Examples 3 and 8 was carried out using whole milk samples in an Eppendorf tube and $2 \cdot 10^{-8}$-$1.5 \cdot 10^{-7}$ mol/ml methyl red as a quality (freshness/spoilage) indicator. Fresh sample mixed with indicator was yellow (FIG. 11A, top). During the transition phase (middle photographs) and when spoiled (bottom photographs) milk samples were colorless (white).

Thus, there was a visually distinct change in color from yellow of fresh milk to white of spoiled milk, establishing the feasibility of methyl red as an indicator for food spoilage with no need to use dilution or filtration through a membrane.

Figure 11B:
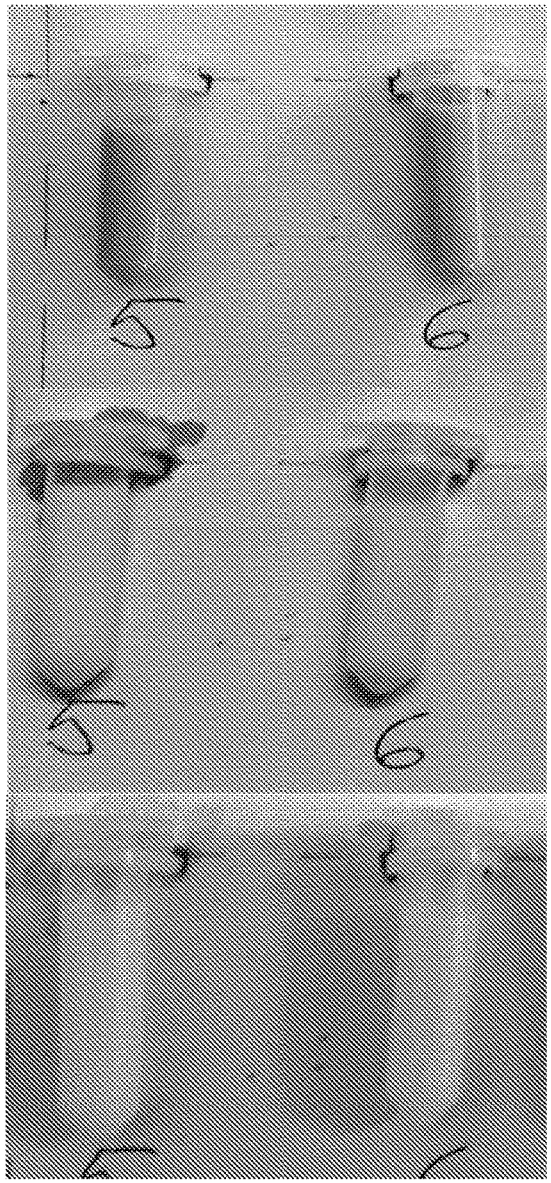
FIG. 11B is showing a whole milk sample stored in two Eppendorf tubes, each comprising an indigo carmine solution, when fresh (top photograph), during a transition phase (middle photograph) and when spoiled (bottom photographs).

A similar experiment with whole milk was carried out using indigo carmine as an indicator. Generally, indigo carmine is a pH sensitive indicator, which changes its color from yellow above pH 13.0 to blue below pH 11.4. The sample-indicator mixture was blue at the preparation, when the milk was fresh (FIG. 11B, top). During spoilage the samples were colorless (white; FIG. 11B, middle and bottom, respectively).

The visually distinct change in color from blue in fresh milk to white in spoiled milk shows the feasibility of indigo carmine as an indicator for food quality with no need to use dilution or separation of the food sample from the indicator.

Without wishing to be bound by any theory or mechanism, it is noted that in the case of indigo carmine indicator, the color change may result from reduction of the C=C bond, rather than from a protonation/deprotonation process. The reduction of this bond is known to be caused by bacterial action, therefore the disappearance for the blue color from the indigo carmine solution indicated the spoilage of the milk directly through indicating bacterial action, rather than a pH change, which typically follows a growth in bacterial population.

Figure 11C:
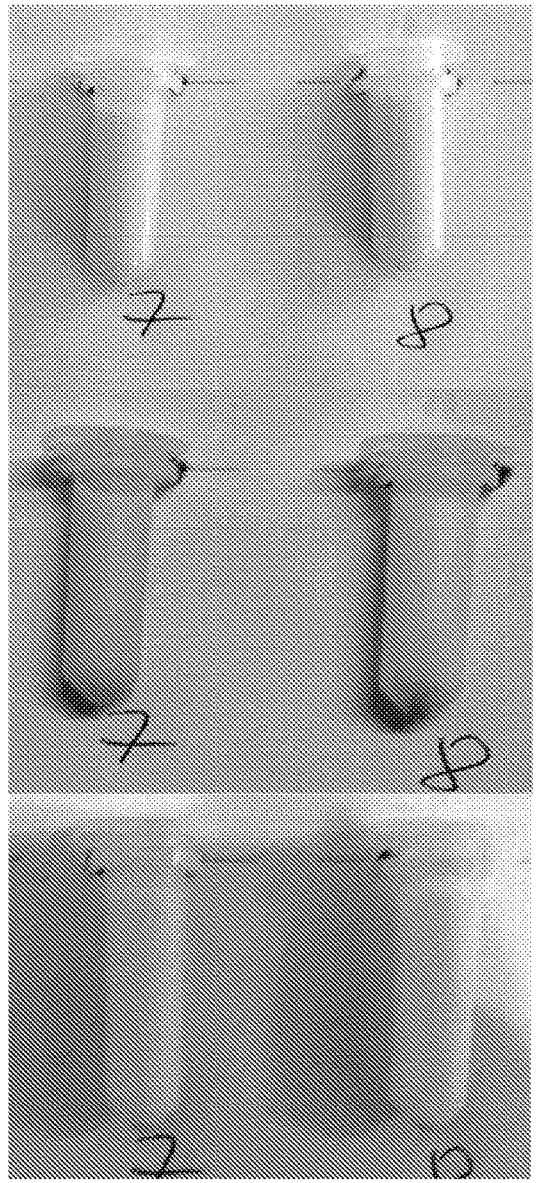
FIG. 11C is showing a whole milk sample stored in two Eppendorf tubes, each comprising a carmoisine red solution, when fresh (top photograph), during a transition phase (middle photograph), and when spoiled (bottom photograph).

A similar experiment with whole milk was conducted using carmoisine red as a quality indicator. Typically, carmoisine red serve as a dye, and specifically as a red food colorant. The sample-indicator mixture was pink at the preparation, when the milk was fresh (FIG. 11C, top). During spoilage (middle photographs) and when spoiled (bottom photographs), the milk samples were colorless.

Thus, the visually distinct change in color from pink in fresh milk to white in spoiled milk suggests the feasibility of carmoisine red as an indicator for food quality with no need to perform dilutions or filter out interfering components.

Without wishing to be bound by any theory or mechanism, it is suggested that the color change in the presence of carmoisine red may result from reduction of the N=N bond, rather than from a protonation/deprotonation process. The reduction of this bond is known to be caused by bacterial action, therefore the disappearance of the pink color from the carmoisine red solution was due to the presence of bacteria, or bacterial action (rather than a pH change that typically follows growth in bacterial population).

Figure 11D:
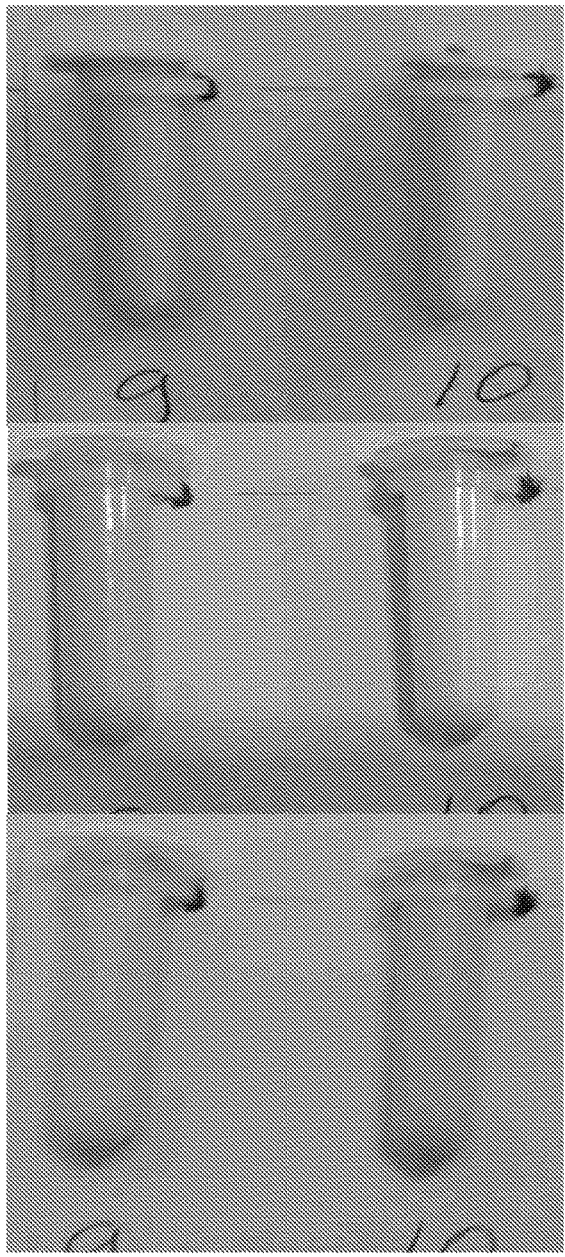
FIG. 11D is showing a whole milk sample stored in two Eppendorf tubes, each comprising a tartrazine solution, when fresh (top photograph), during a transition phase (middle photograph), and when spoiled (bottom photograph).

A similar experiment with whole milk was carried out using tartrazine as the quality indicator. Generally, tartrazine serves as a dye, and specifically as a red food colorant, hence, its use as an indicator for food quality is shown here for the first time. The sample-indicator mixture was yellow at the preparation, when the milk was fresh (FIG. 11D, top) and colorless during spoilage (FIG. 11D, middle photographs) and when spoiled (FIG. 11D, bottom photographs).

The visual change in color from distinct yellow in fresh milk to white-yellowish in spoiled milk, showed the feasibility of tartrazine as an indicator for food spoilage with no need to perform dilutions or to filter out interfering components.

Without wishing to be bound by any theory or mechanism it is suggested that the color change of tartrazine may result from reduction of the N=N bond, rather than from a protonation/deprotonation process. The reduction of this bond is known to be caused by bacterial action, therefore the disappearance of the yellow color from the tartrazine solution corresponds to bacterial action (rather than to a pH change, which typically follows a growth in bacterial population).

Figure 11E:
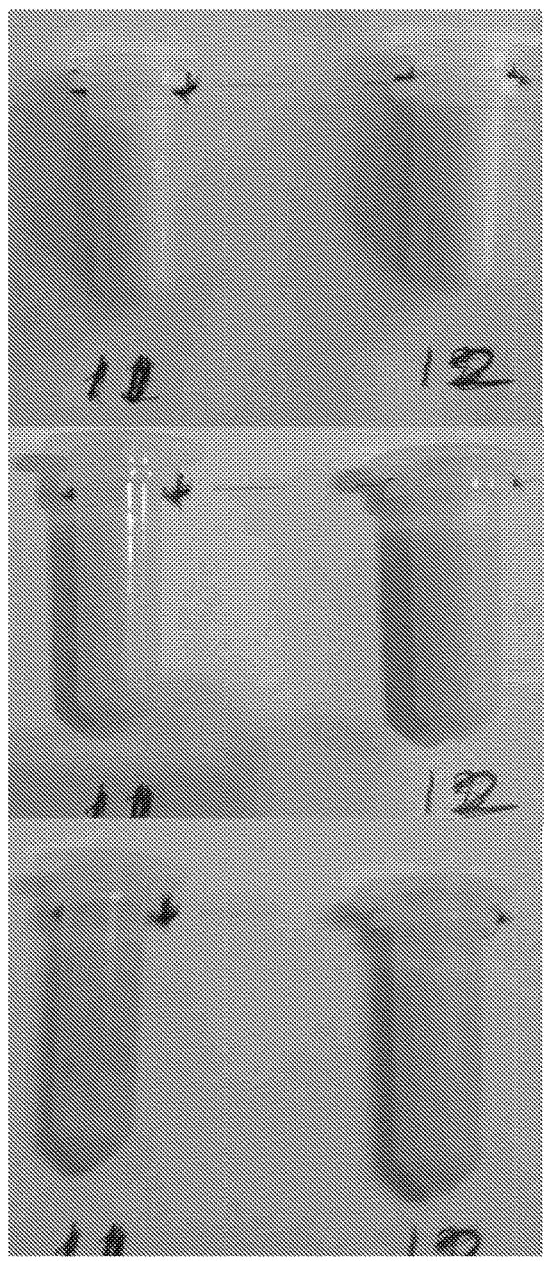
FIG. 11E is showing a whole milk sample stored in two Eppendorf tubes, each comprising a bromocresol green solution, when fresh (top photograph), during a transition phase (middle photograph), and when spoiled (bottom photograph).

A similar experiment with whole milk was carried out using bromocresol green as a quality indicator. It is also known as 3',3'',5',5''-tetrabromo-m-cresol-sulfonephthalein, type: $HIn+H_2O$ $In^-+H_3O^+$, pK: 4.90. Typically, bromocresol green is a pH sensitive indicator, changing color from blue above pH 5.4 to yellow below pH 3.8. The sample-indicator mixture was pink at the preparation, when the milk was fresh (FIG. 11E, top) and colorless during spoilage (FIG. 11E, middle photographs) and when spoiled (FIG. 11E, bottom photographs).

The visual change in color from pink in fresh milk to white (colorless) in spoiled milk is showing the feasibility of bromocresol green to serve as an indicator for food quality without the need to perform dilutions or to filter out interfering substances.

Figure 11F:
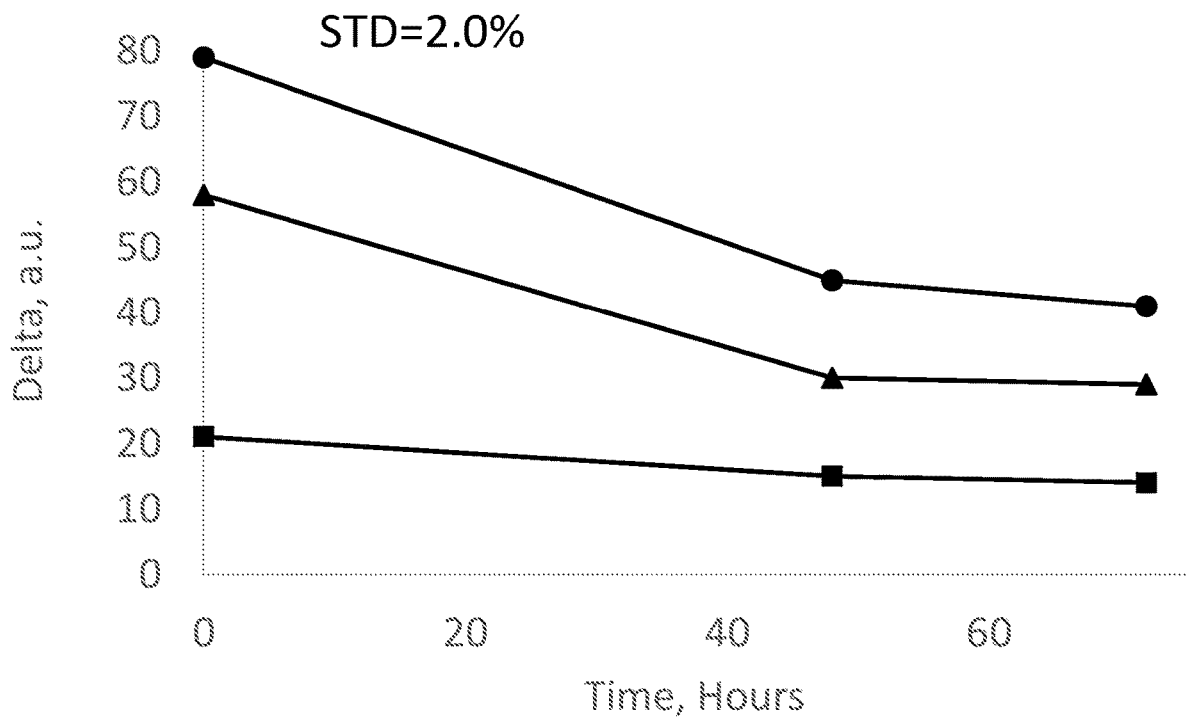
FIG. 11F is an image analysis in the RGB base in Red-Blue (squares) Red-Green (circles) and Green-Blue (triangles) corresponding to FIG. 11A.
Figure 11G:
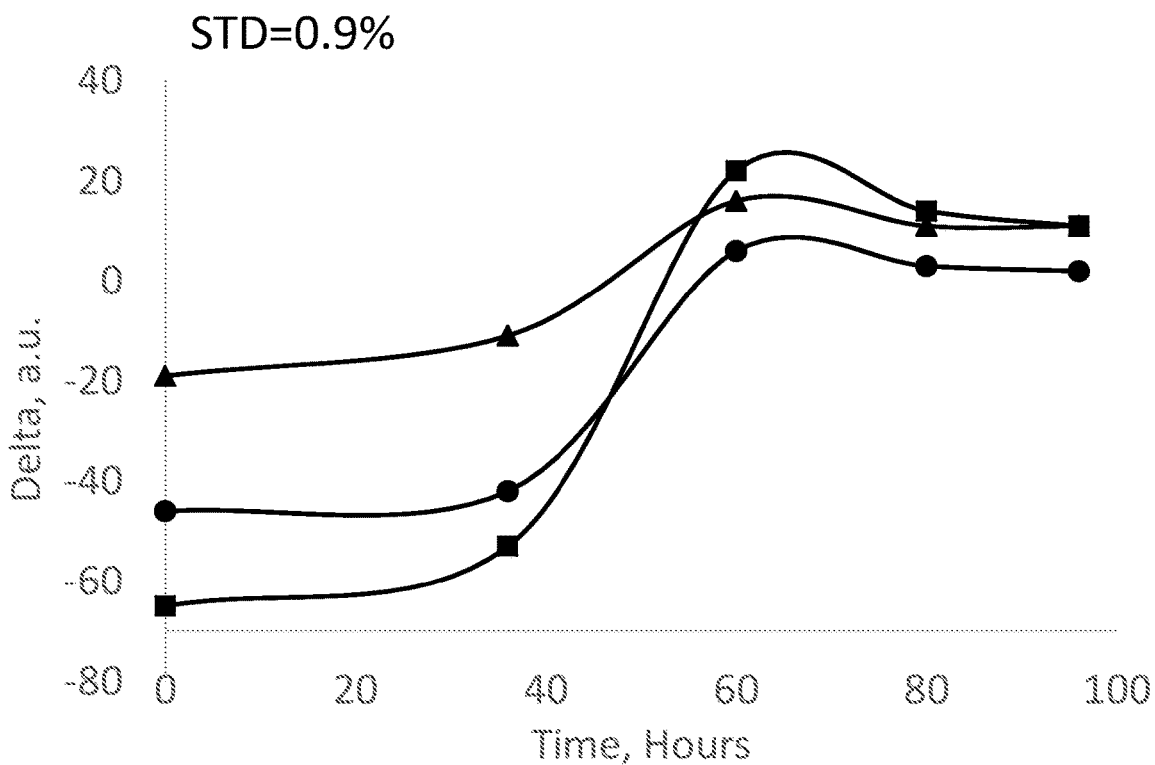
FIG. 11G is an image analysis in the RGB base in Red-Blue (squares) Red-Green (circles) and Green-Blue (triangles corresponding to FIG. 11B.
Figure 11H:
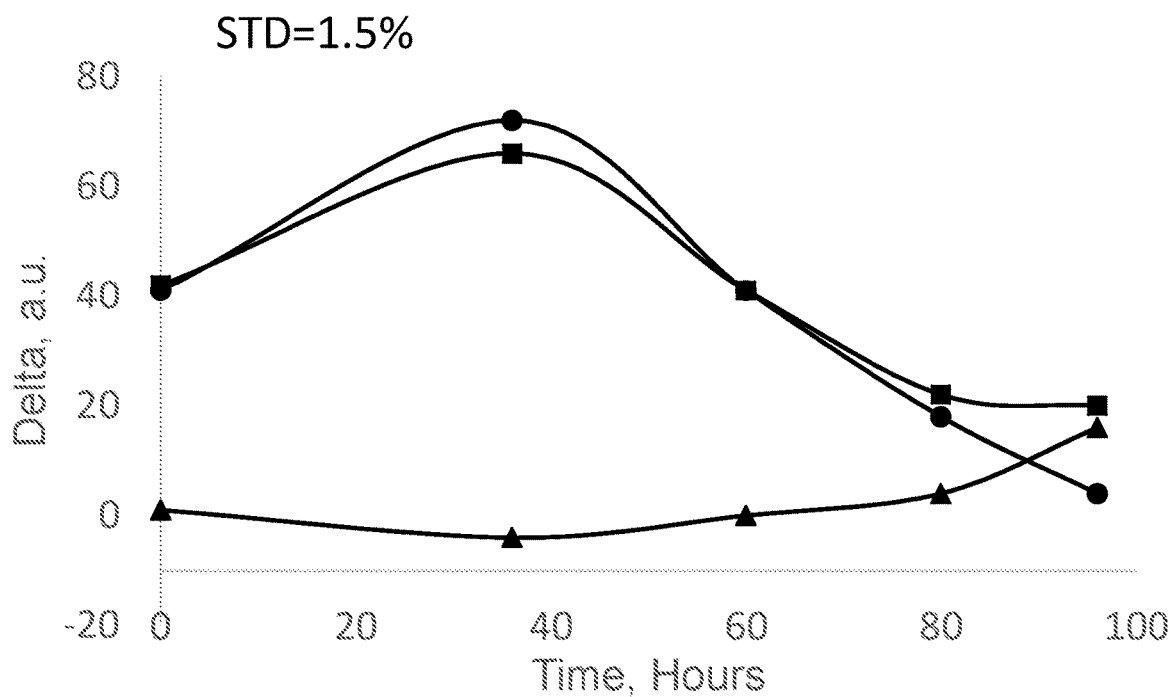
FIG. 11H is an image analysis in the RGB base in Red-Blue (squares) Red-Green (circles) and Green-Blue (triangles) corresponding to FIG. 11C.
Figure 11I:
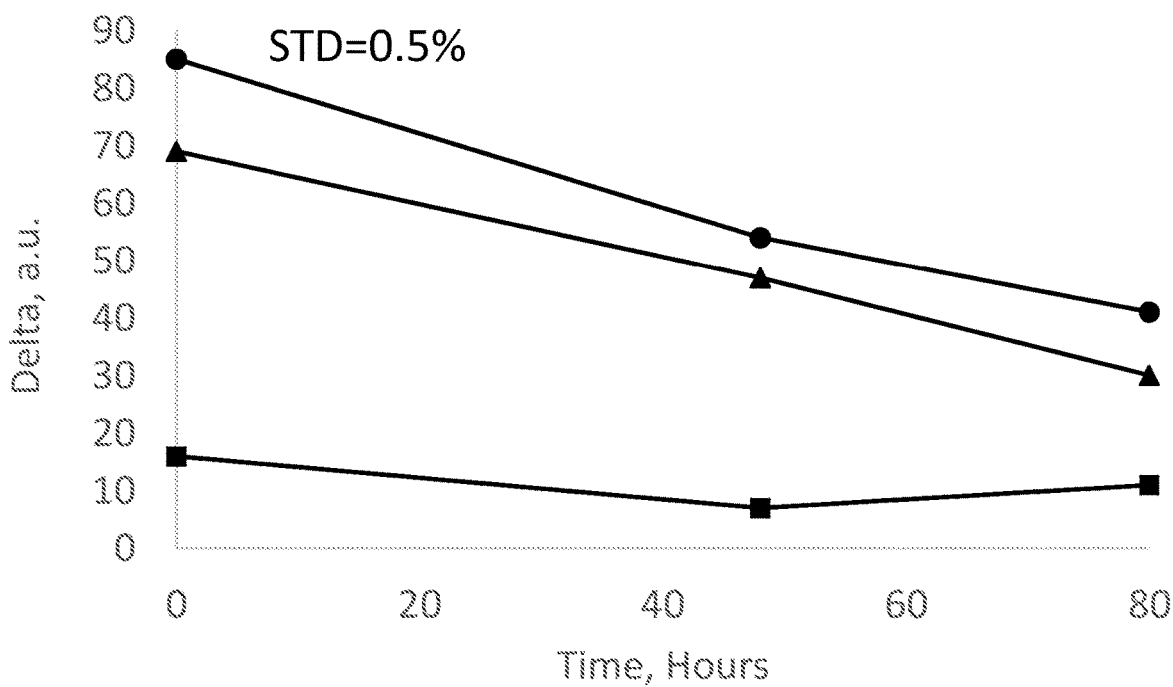
FIG. 11I is an image analysis in the RGB base in Red-Blue (squares) Red-Green (circles) and Green-Blue (triangles) corresponding to FIG. 11D.
Figure 11J:
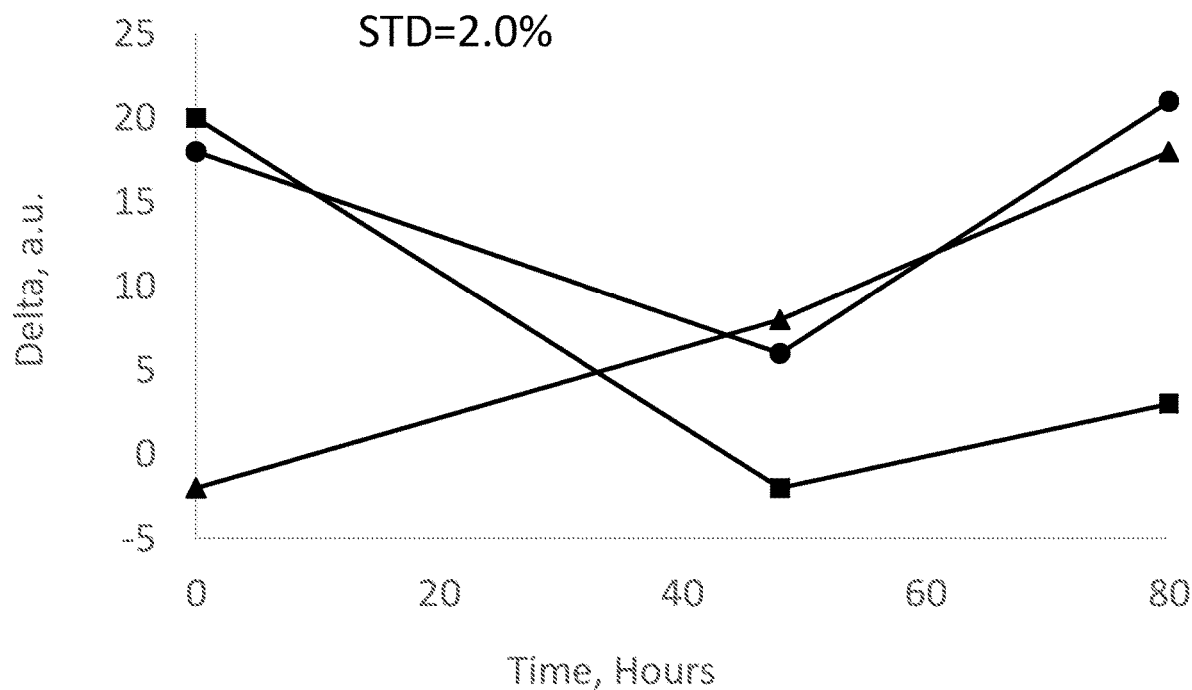
FIG. 11J is an image analysis in the RGB base in Red-Blue (squares) Red-Green (circles) and Green-Blue (triangles) corresponding to FIG. 11E.

In addition, color changes (RGB scale) of the whole milk samples in the presence of methyl red (FIG. 11A), indigo carmine (FIG. 11B), carmoisine red (FIG. 11C), tartrazine (FIG. 11D) and bromocresol green (FIG. 11E) were monitored for up to 95 h in order to quantitate the color change observed during the spoilage process. The results corresponding to methyl red as an indicator are presented in FIG. 11F, which show that in Red-Blue (circles), Green-Blue (triangles) and Red-Green (squares) color ranges there is a significant change upon the spoilage of the milk samples. The results bolster the findings that methyl red indicator is suitable for spoilage detection or for monitoring quality of whole milk samples. The results corresponding to indigo carmine as an indicator are presented in FIG. 11G, which show that in Red-Blue (squares), Green-Blue (triangles) and Red-Green (circles) color ranges there is a significant change upon the spoilage of the milk samples. The results bolster the findings that indigo carmine indicator is suitable for spoilage detection or for monitoring quality of whole milk samples. The results corresponding to carmoisine red as an indicator are presented in FIG. 11H, which shows that in Red-Blue (squares), Green-Blue (triangles) and Red-Green (circles) color ranges there is a significant change upon the spoilage of the milk. The results thus bolster the findings that carmoisine red is suitable indicator for monitoring the quality of whole milk. The results corresponding to tartrazine as an indicator are presented in FIG. 11I, which shows that in Red-Blue (circles), Green-Blue (triangles) and Red-Green (squares) color ranges there is a significant change upon the spoilage of the milk. The results thus bolster the findings that tartrazine is suitable indicator for monitoring the quality of whole milk. The results corresponding to bromocresol green as an indicator are presented in FIG. 11J, which shows that in Red-Blue (circles), Green-Blue (triangles) and Red-Green (squares) color ranges there is a significant change upon the spoilage of the milk. The results thus bolster the findings that bromocresol green is suitable indicator for monitoring the quality of whole milk.

Example 9B

Quality Indication of Whole Milk Using a Bacterial Indicator

Small (0.5 ml), medium (1.5 ml) and large (50 ml) milk samples were prepared as described in Example 2B by combining 500 ml row milk and 6 gr of 0.02% indigo carmine aqueous solution at 4° C. The concentrations of indicator within the samples were in the range of $2 \cdot 10^{-8}$ to $1.5 \cdot 10^{-7}$ mol/ml.

After 1 h in 4° C. the mixture was divided into four 50 ml samples, two sets of three 1.5 ml samples and fifteen 0.5 ml samples. All the samples were measured to have pH=6.77. The pH values of the samples were monitored for up to 60 hours, while being stored at 18-20° C. as described in Example 2B. Color changes (RGB scale) of the above samples of milk with indigo carmine were monitored during that period in order to learn whether a visible change is observed during the spoilage process.

Figure 11K:
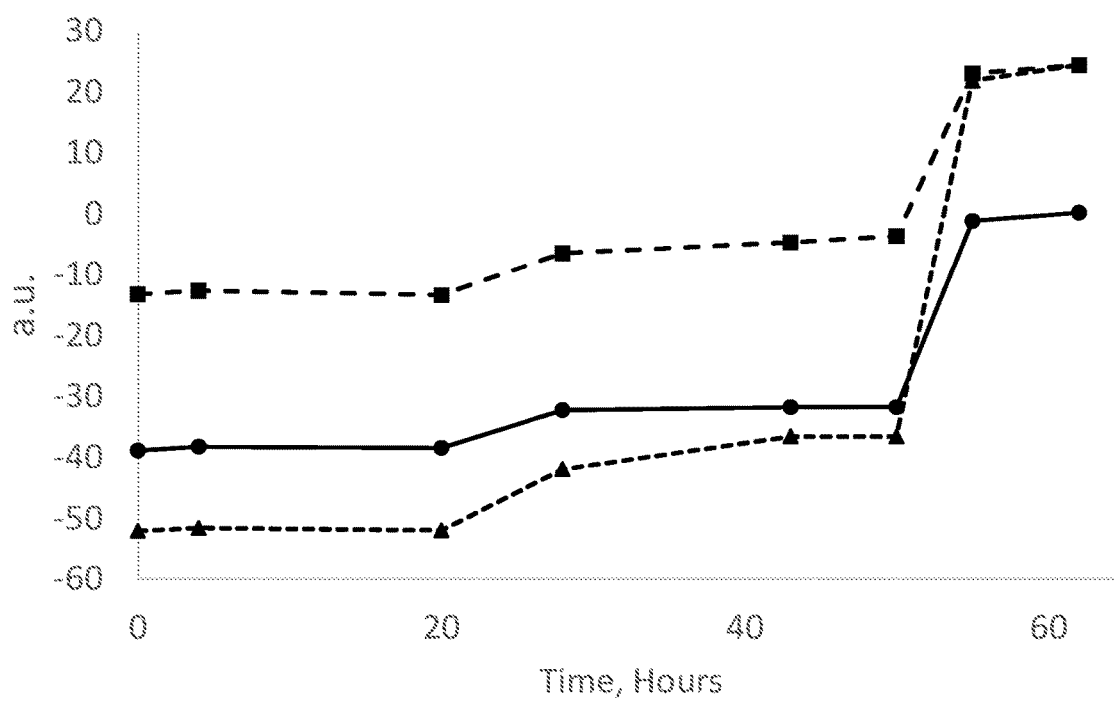
FIG. 11K is an image analysis in the RGB base in Red-Blue (dashed line, triangles), Green-Blue (dashed line, squares) and Red-Green (solid line, circles) of 1.5 ml milk samples stored at 18-20° C. with indigo carmine.
Figure 11L:
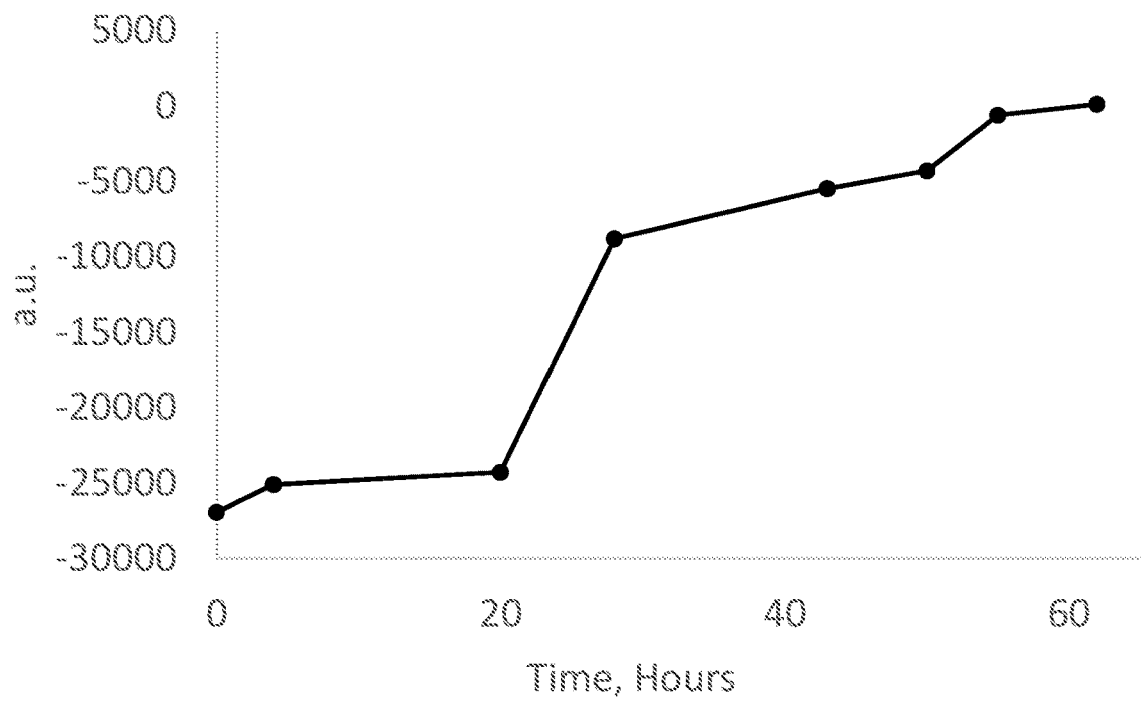
FIG. 11L shows the product of Red-Blue×Green-Blue×Red-Green corresponding to FIG. 11K.
Figure 11M:
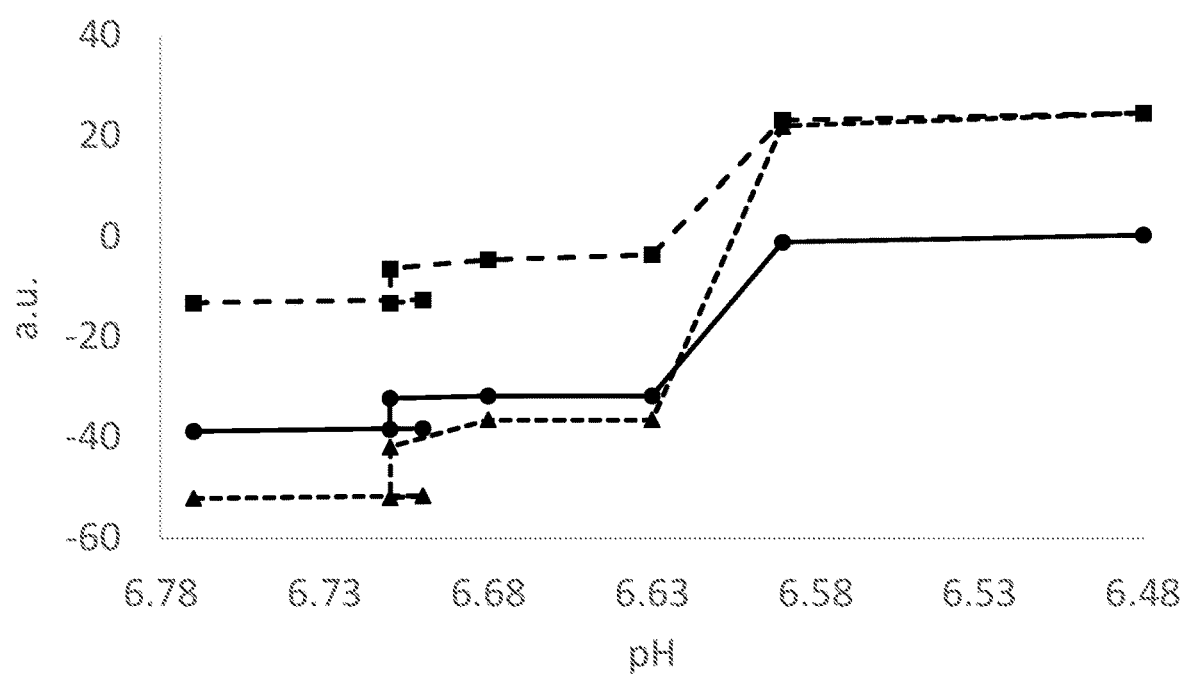
FIG. 11M depicts the measured pH during spoilage corresponding to FIG. 2B vs. RGB reflection in Red-Blue (dashed line, triangles), Green-Blue (dashed line, squares) and Red-Green (solid line, circles) upon the spoilage of the milk samples corresponding to FIG. 11K.

The results corresponding to indigo carmine as an indicator are presented in FIG. 11K, which shows that in Red-Blue (dashed line, triangles), Green-Blue (dashed line, squares) and Red-Green (solid line, circles) color ranges there is a significant change upon the spoilage of the milk samples. In addition, FIG. 11L, shows that the product of Red-Blue×Green-Blue×Red-Green also shows a significant change upon the spoilage of the milk samples. The results bolster the findings that bacterial indicators, such as indigo carmine, are suitable for spoilage detection or for monitoring quality of whole milk samples. The correlation between spoilage measured by pH change and the spoilage as measured by indigo carmine color changes is seen in FIG. 11M, which depicts the measured pH during spoilage vs. RGB reflection in Red-Blue (dashed line, triangles), Green-Blue (dashed line, squares) and Red-Green (solid line, circles) upon the spoilage of the milk samples.

Figure 11N:
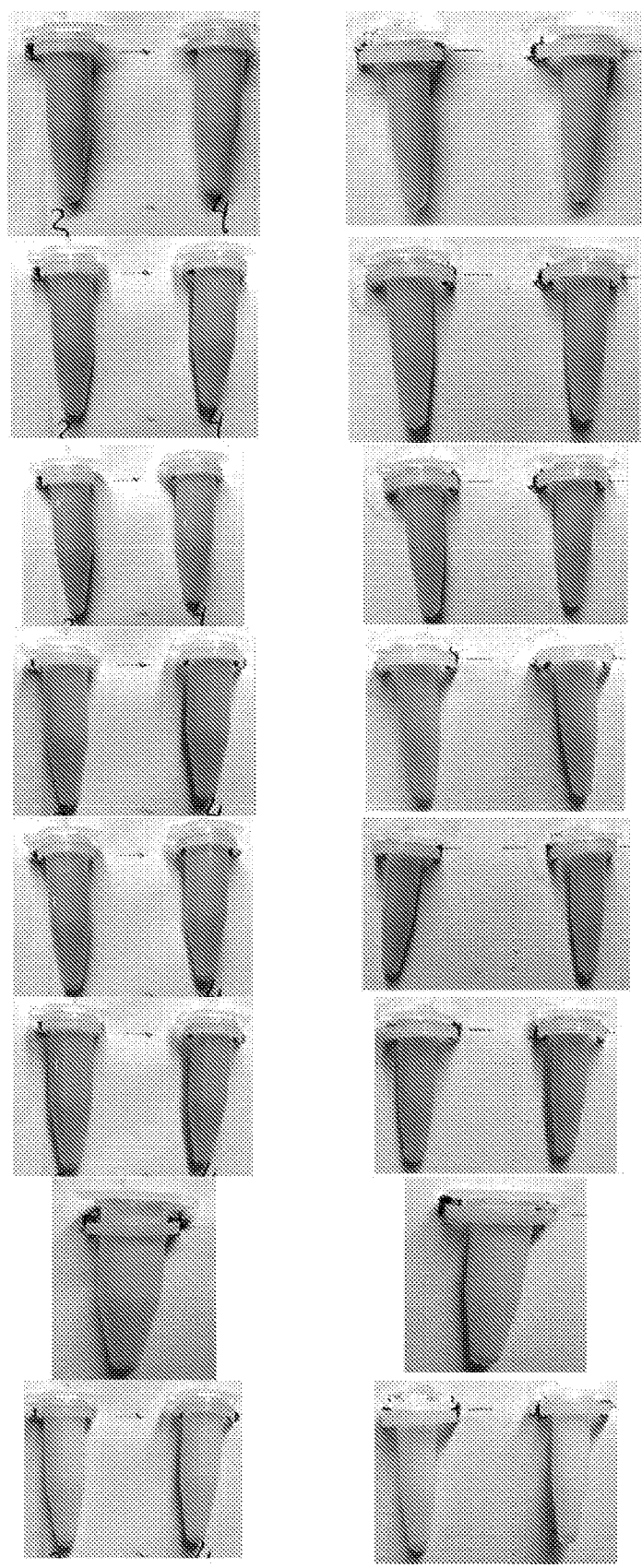
FIG. 11N is showing photographs of milk samples corresponding to FIG. 11K—0.5 ml sample (right column) and 1.5 ml sample (left column)—in two Eppendorf tubes; when fresh (top line), after 4 h at 18-20° C. (second line from the top), after 20 h at 18-20° C. (third line from the top), after 28 h at 18-20° C. (third line from the top), after 43 h at 18-20° C. (fourth line from the top), after 50 h at 18-20° C. (fifth line from the top), after 55 h at 18-20° C. (sixth line from the top) and after 62 h at 18-20° C. (bottom line).

The small (0.5 ml) and medium (1.5 ml) sample were also examined visually. The sample-indicator mixtures were blue at the preparation, when the milk was fresh whereas during spoilage the samples were colorless. FIG. 11N is showing photographs of one of the 0.5 milk samples (right column) and one of the 1.5 ml samples (left column) in two Eppendorf tubes; when fresh (top line; pH=6.77), after 4 h at 18-20° C. (second line from the top; pH=6.7), after 20 h at 18-20° C. (third line from the top; pH=6.71), after 28 h at 18-20° C. (third line from the top; pH=6.71), after 43 h at 18-20° C. (fourth line from the top; pH=6.68), after 50 h at 18-20° C. (fifth line from the top; pH=6.63), after 55 h at 18-20° C. (sixth line from the top; pH=6.59) and after 62 h at 18-20° C. (bottom line; pH=6.48).

The visually distinct change in color from blue in fresh milk to white in spoiled milk shows the feasibility of bacterial indicators, e.g. indigo carmine, as food quality indicators with no need to use dilution or separation of the food sample from the indicator.

Example 10

Quality Indication of Yogurt Using Methyl Red

As seen in Example 3, pH indicators fail to distinguish fresh milk samples from spoiled ones, due to the turbidity of the milk. On the other hand, in Example 9 it was shown that turbidity can be overcome by monitoring growth of bacterial population rather than pH, preferably with indicator that are non-antibacterial, and moreover that perform a color change by reduction of an internal bond.

In order to expand the scope of the disclosure, experiments were carried out with sheep's milk yogurt, which is more acidic and more turbid than milk, and also takes longer to spoil compared to milk.

Sheep's milk yogurt samples were mixed with methyl red as a quality indicator, in order to demonstrate that bacterial indicators are effective in a wide pH range (in continuance to Example 9). The concentrations of indicator within the samples were in the range of $1.2 \cdot 10^{-7}$-$8 \cdot 10^{-7}$ mol/ml. Since it takes yogurt more time to spoil, the experiment was conducted for 150 h and at 25° C. Photographs and pH measurements were taken at 0 h, 45 h, 66 h, 90 h and 150 h. pH values were as follows: 4.27, 4.10, 4.04, 4.06 and 3.99 after 0 h, 45 h, 66 h, 90 h and 150 h at 25° C., respectively.

Figure 12:
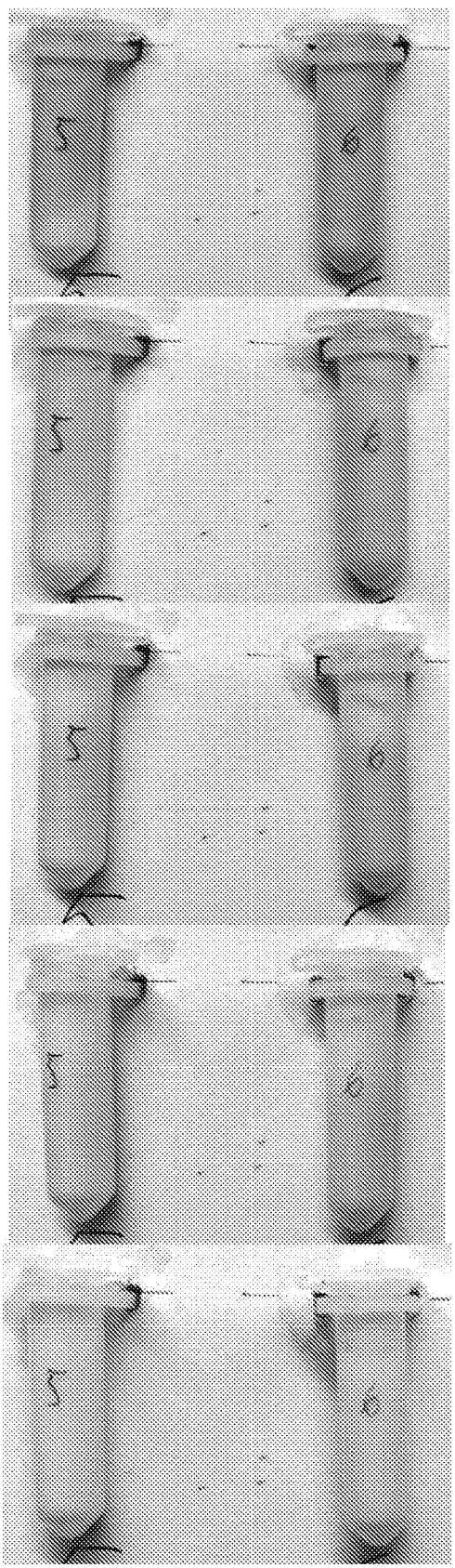
FIG. 12 is showing a yogurt sample stored in two Eppendorf tubes, each having a methyl red solution, when fresh (top photograph), after 45 h at 25° C. (second photograph from top), after 66 h at 25° C. (third photograph from top), after 90 h at 25° C. (second photograph from bottom) and after 150 h at 25° C. (last photograph from top).

The sample-indicator mixture was orange at the preparation, when the yogurt was fresh (FIG. 12, top). Over time the orange color gradually faded until it disappeared (faded completely) at 150 h (FIG. 12, photographs second from top). The visually distinct gradual change in color from orange in fresh yogurt to white in spoiled yogurt, shows the feasibility of methyl red as an indicator for food quality, with no need to use dilution or separation of the food sample from the indicator, without the need to perform dilutions or to filter out interfering substances.

Figure 13:
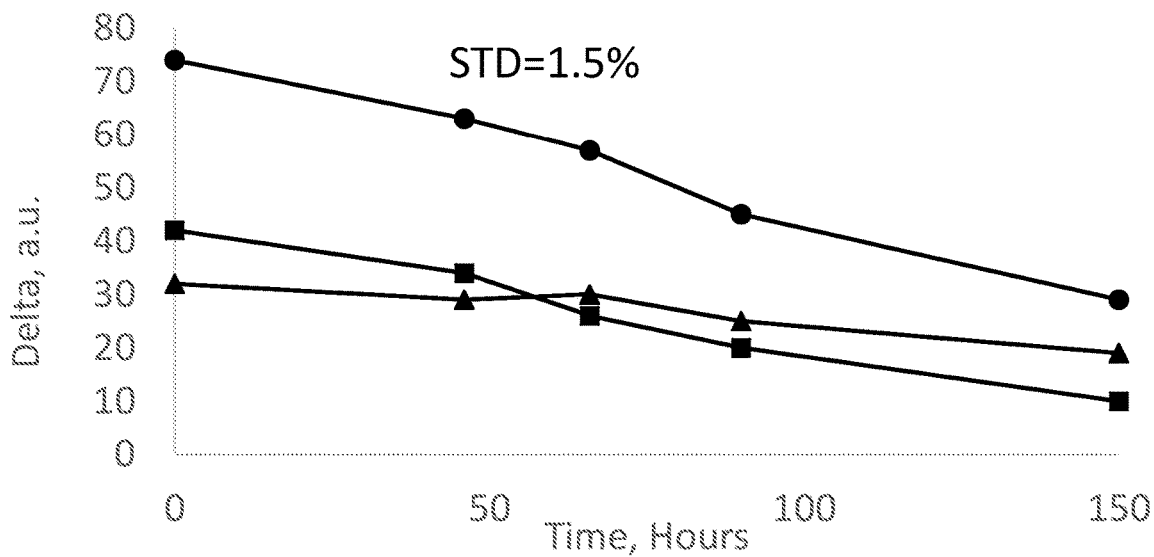
FIG. 13 is an image analysis in the RGB base in Red-Blue (squares) Red-Green (circles) and Green-Blue (triangles) corresponding to FIG. 12.

In addition, color changes (RGB scale) of the above samples of yogurt with methyl red indicator, were monitored for 150 h in order to quantitate the color change observed during the spoilage process. The result are given in FIG. 13, which shows that in both Red-Blue (circles), Green-Blue (triangles) and Red-Green (squares) color ranges there was a significant color change upon spoilage of the milk samples. This change indicates methyl red indicator is suitable for detection or monitoring spoilage of yogurt.

Example 11

Quality Indication of Chicken Breast Using Bacterial Indicators

In order to further expand the scope of the disclosure, experiments were carried out with chicken breast as a representative to non-dairy food products such as meat.

Figure 14:
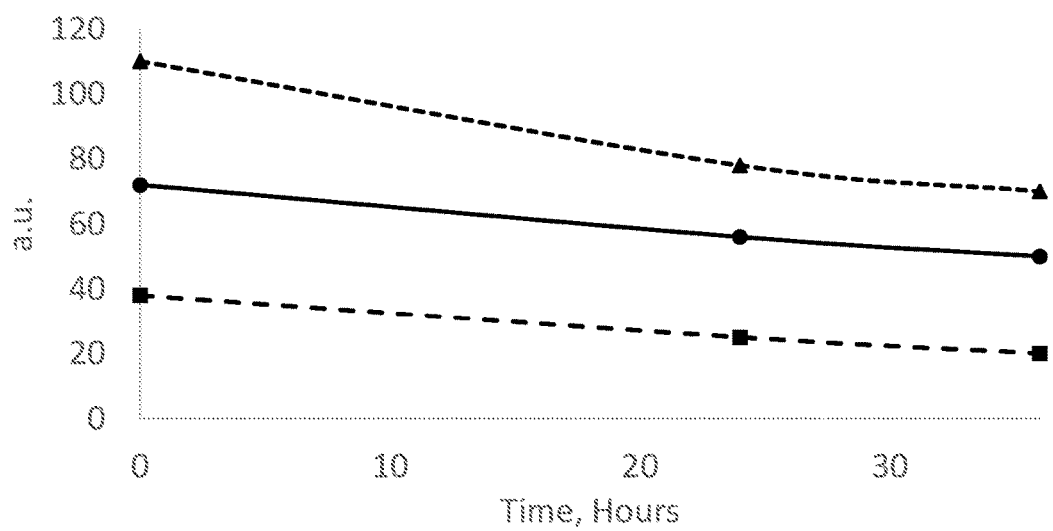
FIG. 14 is an image analysis in the RGB base in Red-Blue (dashed line, triangles), Green-Blue (dashed line, squares) and Red-Green (solid line, circles) of chicken breast samples stored at 24° C. for 36 h with a methyl red solution.

Chicken breast samples were mixed with methyl red as a quality indicator, in order to demonstrate that bacterial indicators are effective in a wide pH range. The experiment was conducted for 36 h at 24° C. Photographs and RGB measurements were taken at 0 h, 24 h and 36 h. The result are given in FIG. 14, which shows that in Red-Blue (dashed line, triangles), Green-Blue (dashed line, squares) and Red-Green (solid line, circles) color ranges there is a change upon the spoilage of the chicken breast samples. This change indicates methyl red indicator is suitable for detection or monitoring spoilage of chicken breast.

Figure 15:
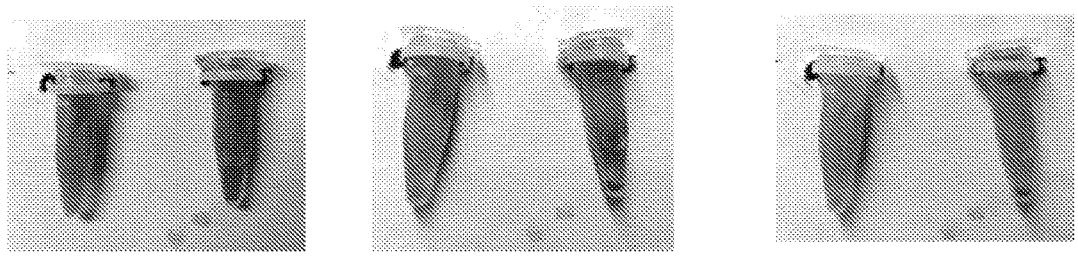
FIG. 15 is showing a chicken breast sample stored in two Eppendorf tubes, each having a methyl red solution, when fresh (left photograph), after 24 h at 24° C. (middle photograph) and after 36 h at 24° C. (right photograph), corresponding to FIG. 14.

The sample—indicator mixture was orange at the preparation, when the chicken breast was fresh (FIG. 15, left photograph). Over time the orange color gradually faded as seen after 24 h at 24° C. (FIG. 15, middle photograph) and after 36 h at 24° C. (FIG. 15, right photograph).

Figure 16:
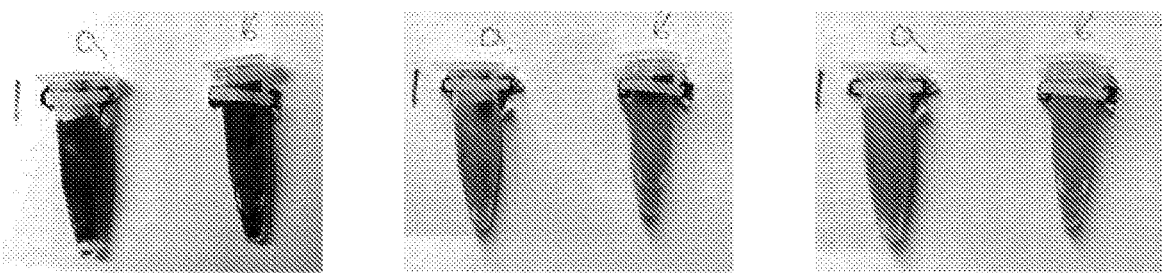
FIG. 16 is showing a chicken breast sample stored in two Eppendorf tubes, each having an indigo carmine solution, when fresh (left photograph), after 24 h at 24° C. (middle photograph) and after 36 h at 24° C. (right photograph).

A similar experiment with chicken breast was carried out using indigo carmine as an indicator. The sample-indicator mixture was blue at the preparation, when the meat was fresh (FIG. 16, left). During spoilage the samples were discolored (after 24 h and 36 h; FIG. 16, middle and right, respectively).

The visually distinct change in color from blue in fresh chicken breast to discoloration in spoiled chicken breast shows the feasibility of indigo carmine as an indicator for food quality with no need to use dilution or separation of the food sample from the indicator.

Figure 17:
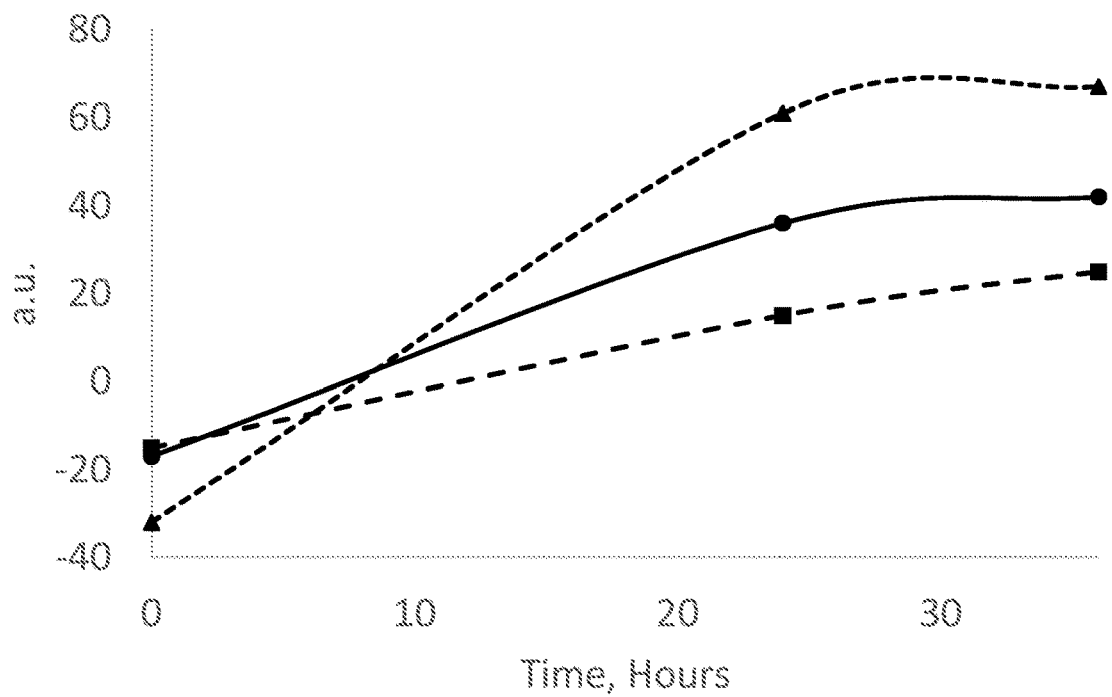
FIG. 17 is an image analysis in the RGB base in Red-Blue (dashed line, triangles), Green-Blue (dashed line, squares) and Red-Green (solid line, circles) corresponding to FIG. 16.

In addition, color changes (RGB scale) of the chicken breast samples in the presence of indigo carmine were monitored for during the 36 h of experiment in order to quantitate the color change observed during the spoilage process. The results corresponding to indigo carmine as an indicator are presented in FIG. 17, which shows that in Red-Blue (dashed line, triangles), Green-Blue (dashed line, squares) and Red-Green (solid line, circles) there is a significant change upon the spoilage of the chicken breast samples. The results bolster the findings that indicators such as indigo carmine indicator are suitable for spoilage detection or for monitoring quality of non-dairy products, such as chicken meat.

Figure 18:
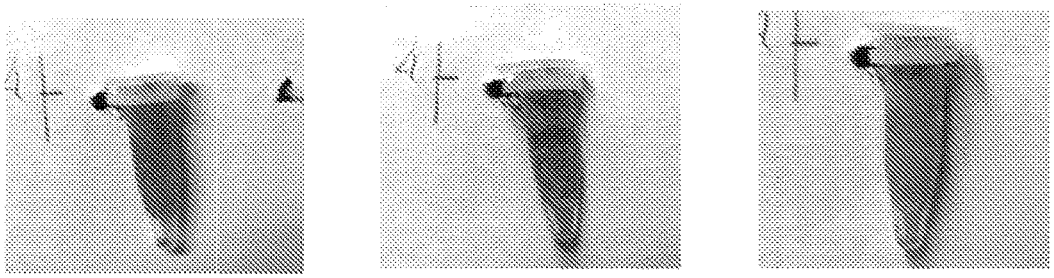
FIG. 18 is showing a chicken breast sample stored an Eppendorf tube having a methyl orange solution, when fresh (left photograph), after 24 h at 24° C. (middle photograph) and after 36 h at 24° C. (right photograph).

A similar experiment with chicken breast was carried out using methyl orange as an indicator. The sample-indicator mixture was orange at the preparation, when the chicken meat was fresh (FIG. 18, left). During spoilage the samples were discolored (after 24 h and 36 h; FIG. 18, middle and right, respectively).

The visually distinct change in color from blue in fresh chicken breast to discoloration in spoiled chicken breast shows the feasibility of methyl orange as an indicator for food quality with no need to use dilution or separation of the food sample from the indicator.

Figure 19:
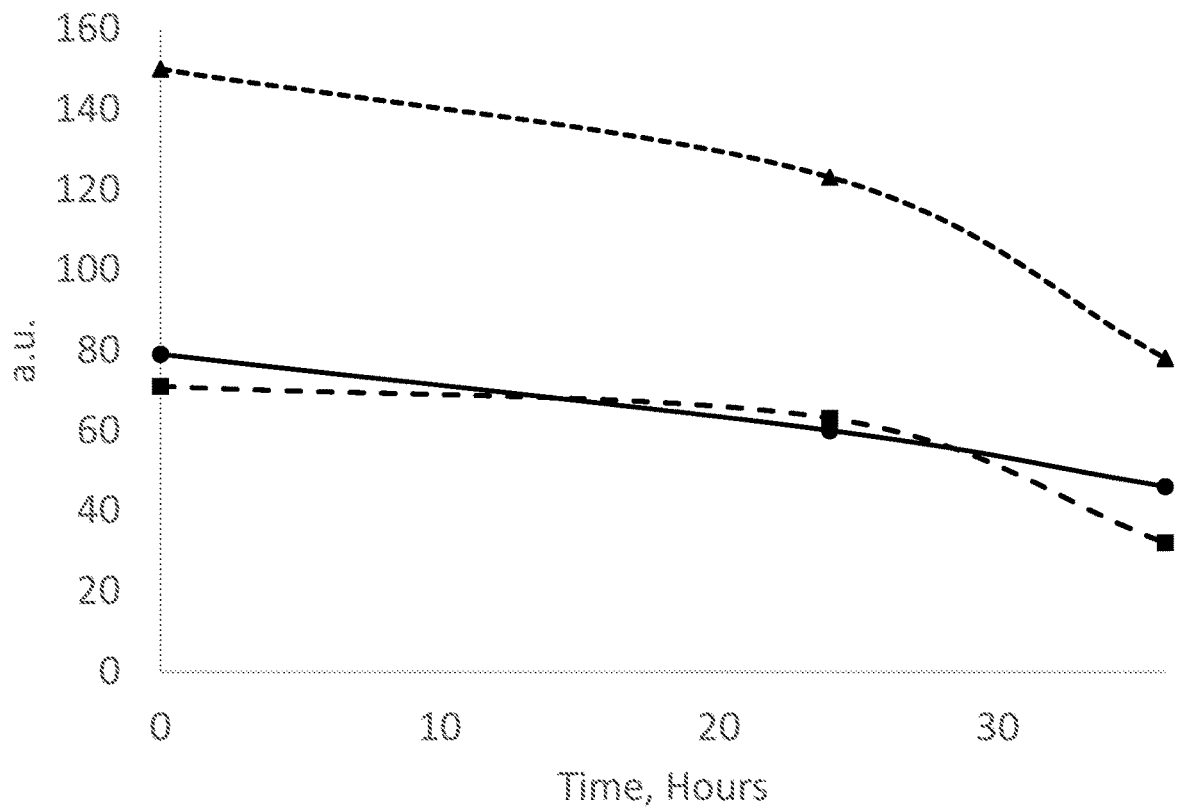
FIG. 19 is an image analysis in the RGB base in Red-Blue (dashed line, triangles), Green-Blue (dashed line, squares) and Red-Green (solid line, circles) corresponding to FIG. 18.

In addition, color changes (RGB scale) of the chicken breast samples in the presence of methyl orange were monitored for during the 36 h of experiment in order to quantitate the color change observed during the spoilage process. The results are presented in FIG. 19, which shows that in Red-Blue (dashed line, triangles), Green-Blue (dashed line, squares) and Red-Green (solid line, circles) there is a significant change upon the spoilage of the chicken breast samples. The results bolster the findings that methyl orange indicator is suitable for spoilage detection or for monitoring quality of chicken products.

Example 12

Quality Indication of Cottage Cheese Using Bacterial Indicators

In order to further expand the scope of the disclosure to products having varied textures, experiments were carried out with cottage cheese.

Figure 20:
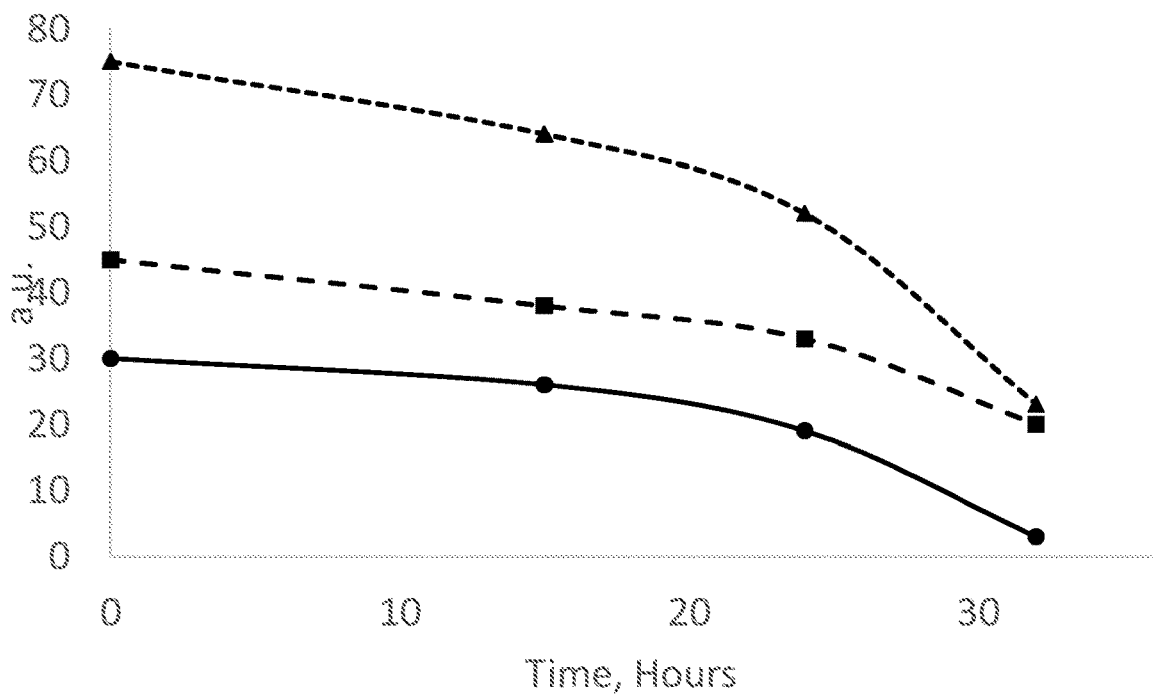
FIG. 20 is an image analysis in the RGB base in Red-Blue (dashed line, triangles), Green-Blue (dashed line, squares) and Red-Green (solid line, circles) of chicken breast samples stored at 24° C. for 36 h with a methyl red solution.
Figure 21:
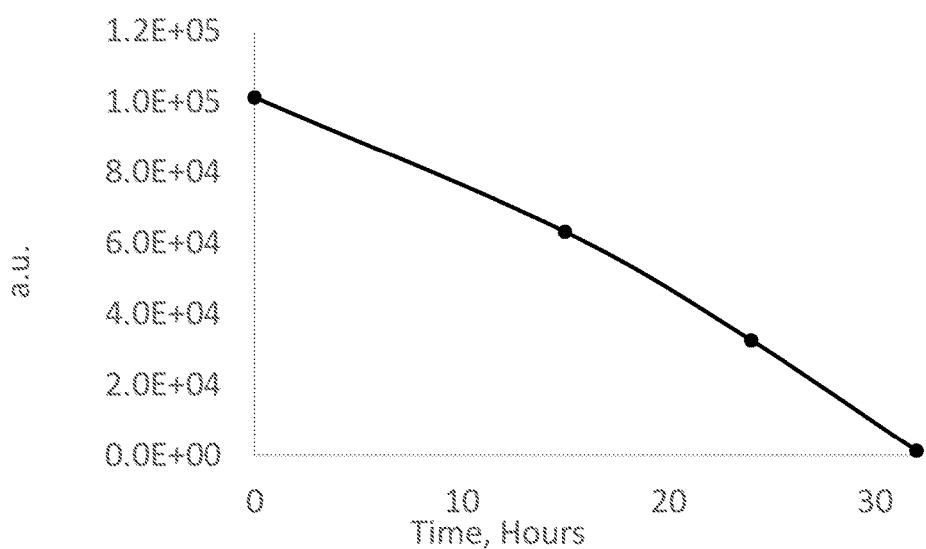
FIG. 21 shows the product of Red-Blue×Green-Blue× Red-Green corresponding to FIG. 20.

Cottage cheese samples were mixed with methyl red as a quality indicator, in order to demonstrate that bacterial indicators are effective in a wide pH range. The concentrations of methyl red within the samples were in the range of $1.2 \cdot 10^{-7}$ to $8 \cdot 10^{-7}$ mol/ml. The experiment was conducted for 32 h at 24° C. Photographs and RGB measurements were taken at 0 h, 15 h, 24 h and 36 h. The result are given in FIG. 20, which shows that in Red-Blue (dashed line, triangles), Green-Blue (dashed line, squares) and Red-Green (solid line, circles) color ranges there is a change upon the spoilage of the cottage cheese samples. In addition, FIG. 21 shows that the product of Red-Blue×Green-Blue×Red-Green also shows a significant change upon the spoilage of the cottage cheese samples. These changes indicate that indicators, such as methyl red, are suitable for detection or monitoring spoilage of products having varied textures.

Figure 22:
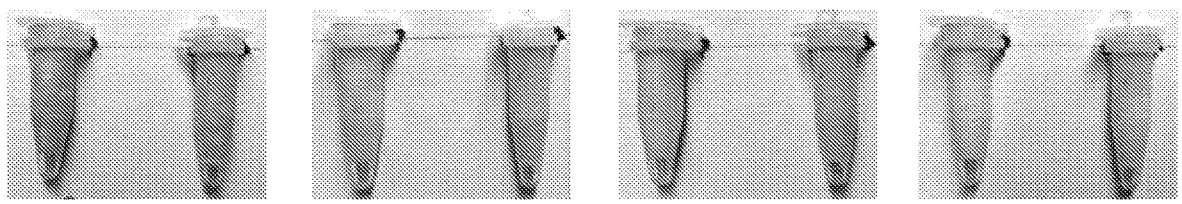
FIG. 22 is showing two cottage cheese samples stored in two Eppendorf tubes, each having a methyl red solution, when fresh (left photograph), after 15 h at 24° C. (second photograph from left), after 24 h at 24° C. (second photograph from right) and after 32 h at 24° C. (right photograph), corresponding to FIG. 20.

The sample-indicator mixture was orange at the preparation, when the cottage cheese was fresh (FIG. 22, left photograph). Over time the orange color gradually faded as seen after 15 h at 24° C. (second photograph from left), after 24 h at 24° C. (second photograph from right) and after 32 h at 24° C. (right photograph).

Figure 23:
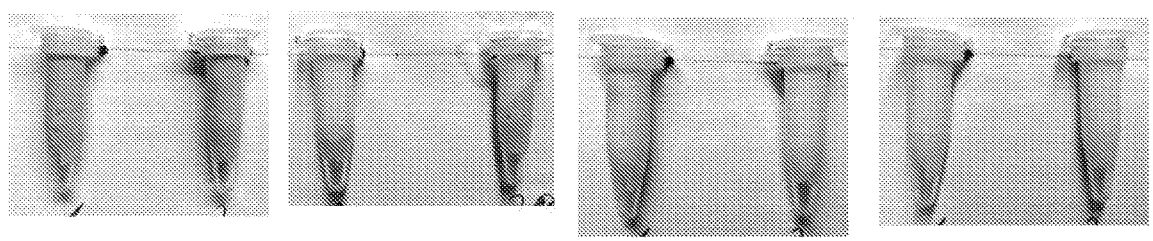
FIG. 23 is showing a cottage cheese sample stored in two Eppendorf tubes, each having an indigo carmine solution, when fresh (left photograph), after 15 h at 24° C. (second photograph from left), after 24 h at 24° C. (second photograph from right) and after 32 h at 24° C. (right photograph).

A similar experiment with cottage cheese was carried out using indigo carmine as an indicator. The sample-indicator mixture was blue at the preparation, when the cottage cheese was fresh (FIG. 23, left). During spoilage the samples were discolored (after 15 h, 24 h and 32 h; FIG. 23, second photograph from left, second photograph from right and right photograph, respectively).

The visually distinct change in color from blue in fresh cottage cheese to discoloration in spoiled cottage cheese shows the feasibility of indicators, such as indigo carmine to indicate food quality with no need to use dilution or separation of the food sample from the indicator.

Figure 24:
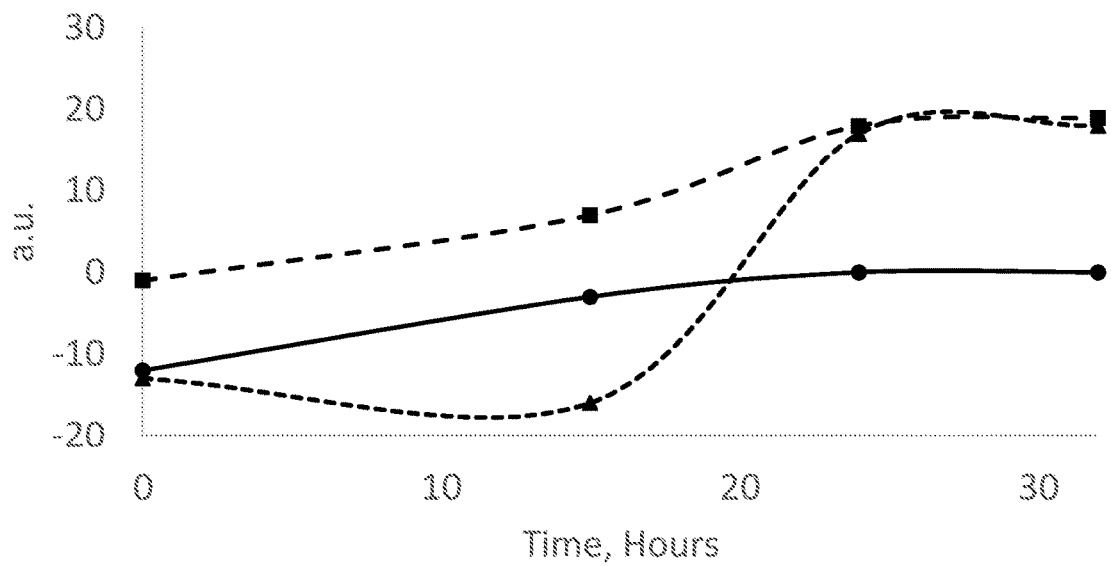
FIG. 24 is an image analysis in the RGB base in Red-Blue (dashed line, triangles), Green-Blue (dashed line, squares) and Red-Green (solid line, circles) corresponding to FIG. 23.
Figure 25:
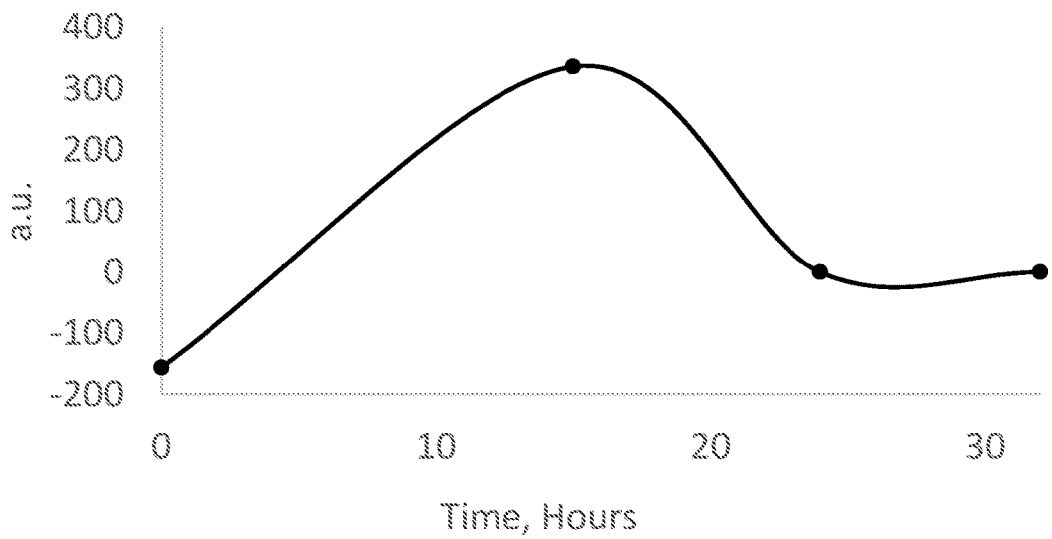
FIG. 25 shows the product of Red-Blue×Green-Blue× Red-Green corresponding to FIG. 24.

In addition, color changes (RGB scale) of the cottage cheese samples in the presence of indigo carmine were monitored for during the 32 h of experiment in order to quantitate the color change observed during the spoilage process. The results corresponding to indigo carmine as an indicator are presented in FIG. 24, which shows that in Red-Blue (dashed line, triangles), Green-Blue (dashed line, squares) and Red-Green (solid line, circles) there is a significant change upon the spoilage of the cottage cheese samples. In addition, FIG. 25 shows that the product of Red-Blue×Green-Blue×Red-Green also shows a significant change upon the spoilage of the cottage cheese samples. The results bolster the findings that indicators, such indigo carmine, are suitable for spoilage detection or for monitoring quality of non-dairy products, such as chicken meat.

Figure 26:
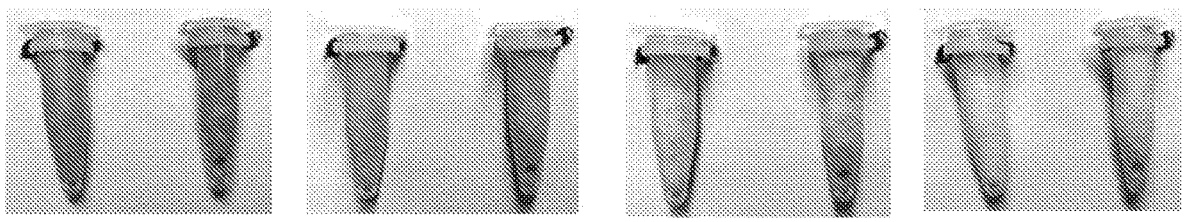
FIG. 26 is showing cottage cheese samples stored in two Eppendorf tubes, each having a methyl orange solution, when fresh (left photograph), after 15 h at 24° C. (second photograph from left), after 24 h at 24° C. (second photograph from right) and after 32 h at 24° C. (right photograph).

A similar experiment with cottage cheese was carried out using methyl orange as an indicator. The sample-indicator mixture was orange at the preparation, when the cheese was fresh (FIG. 26, left). During spoilage the samples were discolored (after 15 h, 24 h and 32 h; FIG. 26, second photograph from left, second photograph from right and right photograph, respectively). The visually distinct change in color from orange in fresh cottage cheese to discoloration in cheese shows the feasibility of methyl orange as an indicator for food quality with no need to use dilution or separation of the food sample from the indicator.

Figure 27:
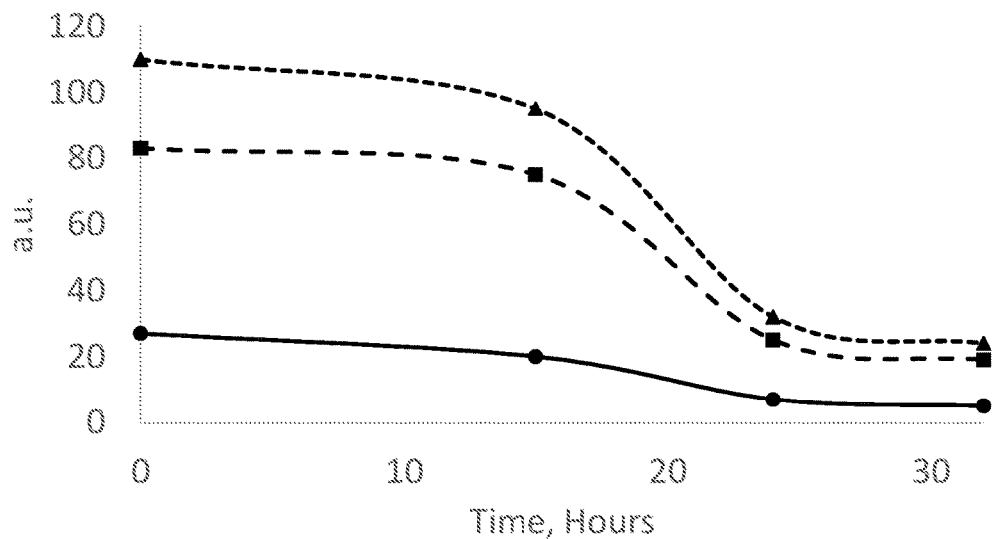
FIG. 27 is an image analysis in the RGB base in Red-Blue (dashed line, triangles), Green-Blue (dashed line, squares) and Red-Green (solid line, circles) corresponding to FIG. 26.
Figure 28:
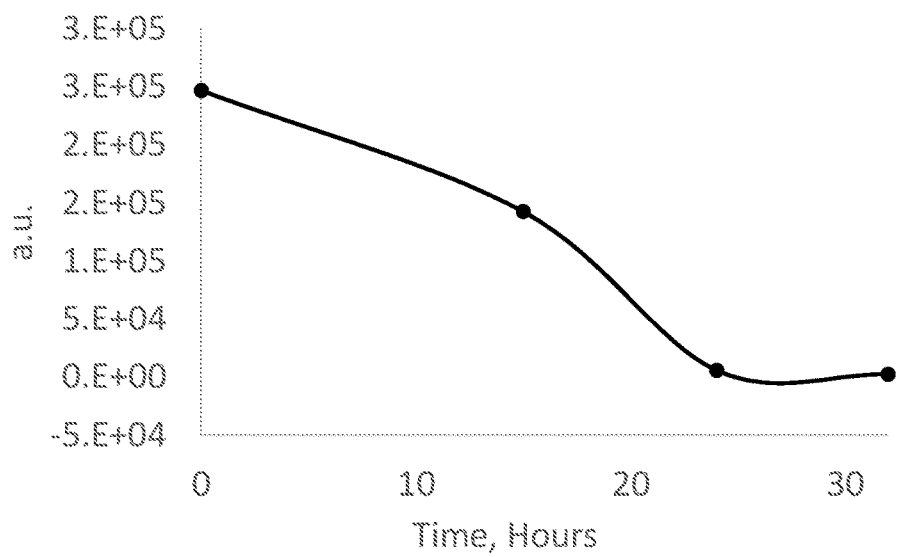
FIG. 28 shows the product of Red-Blue×Green-Blue× Red-Green corresponding to FIG. 27.

In addition, color changes (RGB scale) of the cottage cheese samples in the presence of methyl orange were monitored for during the 32 h of experiment in order to quantitate the color change observed during the spoilage process. The results are presented in FIG. 27, which shows that in Red-Blue (dashed line, triangles), Green-Blue (dashed line, squares) and Red-Green (solid line, circles)

there is a significant change upon the spoilage of the chicken breast samples. In addition, FIG. 28 shows that the product of Red-Blue×Green-Blue×Red-Green also shows a significant change upon the spoilage of the cottage cheese samples. The results bolster the findings that methyl orange indicator is suitable for spoilage detection or for monitoring quality of cheese products.

Figure 29:
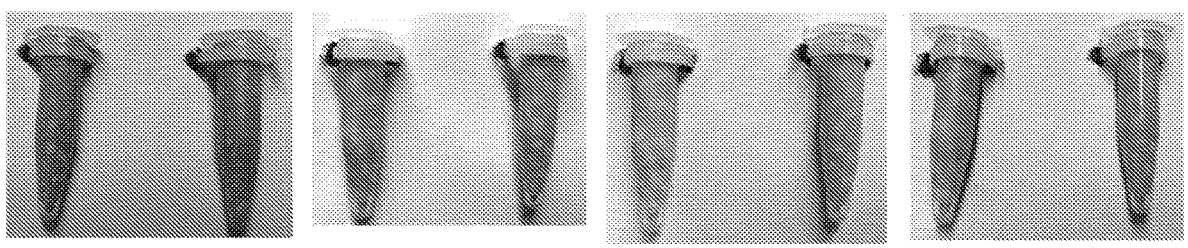
FIG. 29 is showing cottage cheese samples stored in two Eppendorf tubes, each having a bromophenol blue solution, when fresh (left photograph), after 15 h at 24° C. (second photograph from left), after 24 h at 24° C. (second photograph from right) and after 32 h at 24° C. (right photograph).

A similar experiment with cottage cheese was carried out using bromophenol blue as an indicator. The sample-indicator mixture was blue at the preparation, when the cottage cheese was fresh (FIG. 29, left). During spoilage the samples were discolored to light blue (after 15 h, 24 h and 32 h; FIG. 29, second photograph from left, second photograph from right and right photograph, respectively).

The visually distinct change in color from blue in fresh cottage cheese to discoloration in spoiled cottage cheese shows the feasibility of bromophenol blue as an indicator for food quality with no need to use dilution or separation of the food sample from the indicator.

Figure 30:
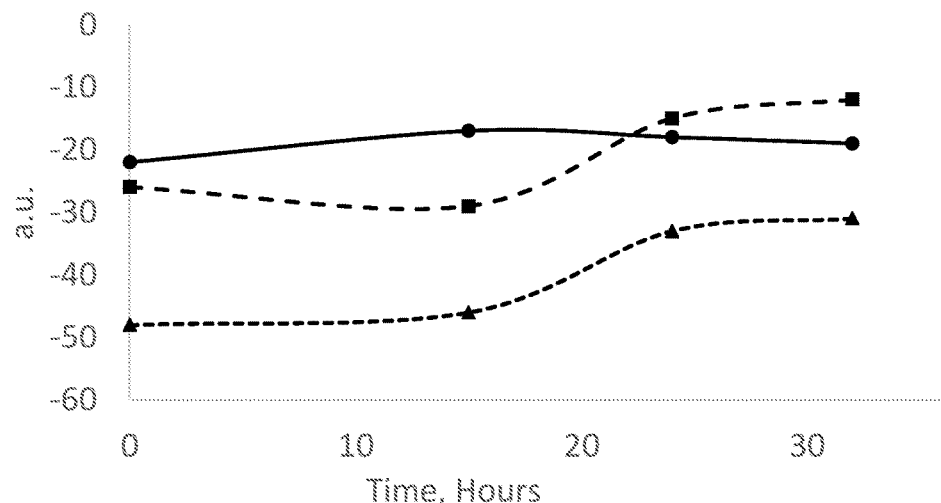
FIG. 30 is an image analysis in the RGB base in Red-Blue (dashed line, triangles), Green-Blue (dashed line, squares) and Red-Green (solid line, circles) corresponding to FIG. 29.
Figure 31:
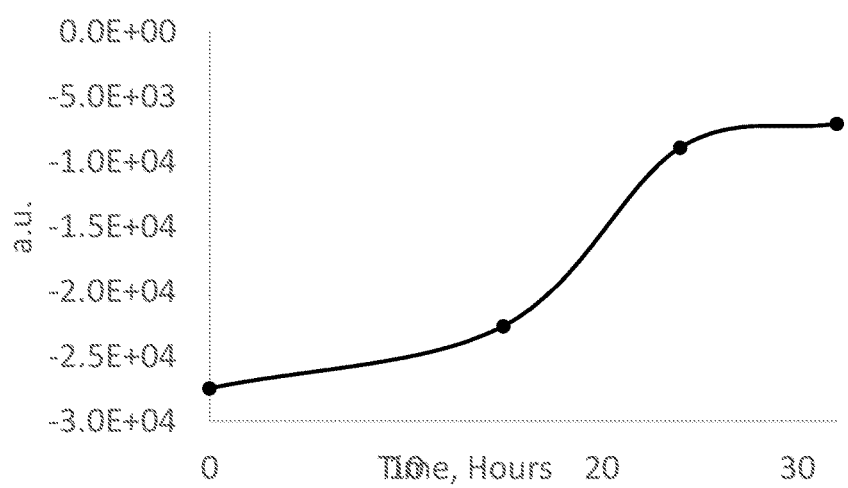
FIG. 31 shows the product of Red-Blue×Green-Blue× Red-Green corresponding to FIG. 30.

In addition, color changes (RGB scale) of the cottage cheese samples in the presence of indigo carmine were monitored for during the 32 h of experiment in order to quantitate the color change observed during the spoilage process. The results corresponding to bromophenol blue as an indicator are presented in FIG. 30, which shows that in Red-Blue (dashed line, triangles), Green-Blue (dashed line, squares) and Red-Green (solid line, circles) there is a significant change upon the spoilage of the cottage cheese samples. In addition, FIG. 31 shows that the product of Red-Blue×Green-Blue×Red-Green also shows a significant change upon the spoilage of the cottage cheese samples. The results bolster the findings that bromophenol blue indicator is suitable for spoilage detection or for monitoring quality of cheese products.

Figure 32:
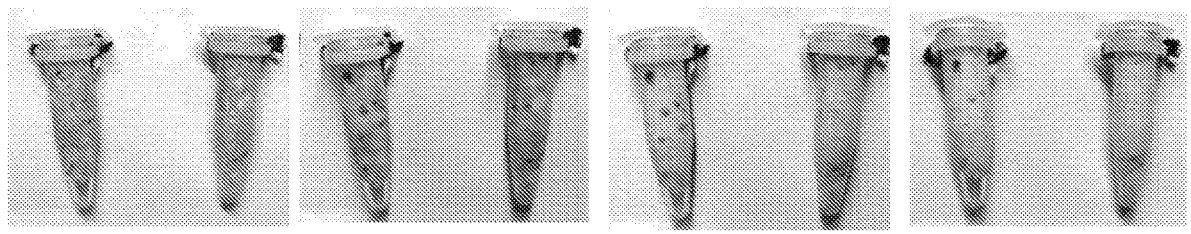
FIG. 32 is showing cottage cheese samples stored in two Eppendorf tubes, each having a carmoisine red solution, when fresh (left photograph), after 15 h at 24° C. (second photograph from left), after 24 h at 24° C. (second photograph from right) and after 32 h at 24° C. (right photograph).

A similar experiment with cottage cheese was carried out using carmoisine red as an indicator. The sample-indicator mixture was pink at the preparation, when the cottage cheese was fresh (FIG. 32, left). During spoilage the samples were discolored to light blue (after 15 h, 24 h and 32 h; FIG. 32, second photograph from left, second photograph from right and right photograph, respectively).

The visually distinct change in color from pink in fresh cottage cheese to discoloration in spoiled cottage cheese shows the feasibility of carmoisine red as an indicator for food quality with no need to use dilution or separation of the food sample from the indicator.

Figure 33:
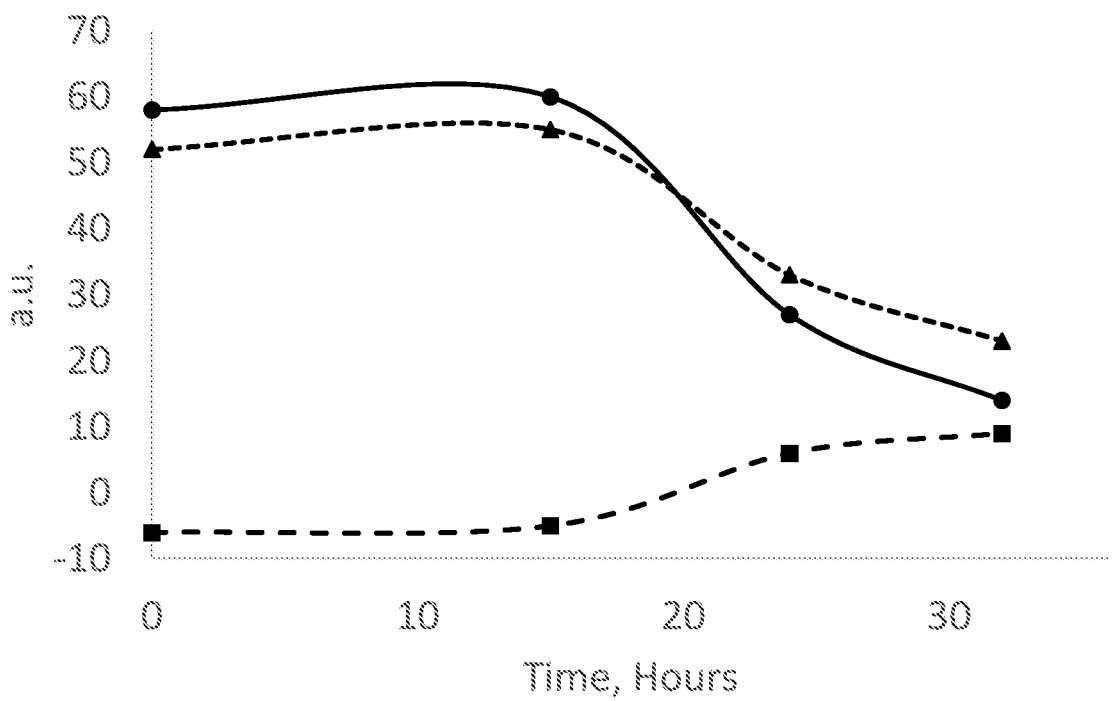
FIG. 33 is an image analysis in the RGB base in Red-Blue (dashed line, triangles), Green-Blue (dashed line, squares) and Red-Green (solid line, circles) corresponding to FIG. 32.
Figure 34:
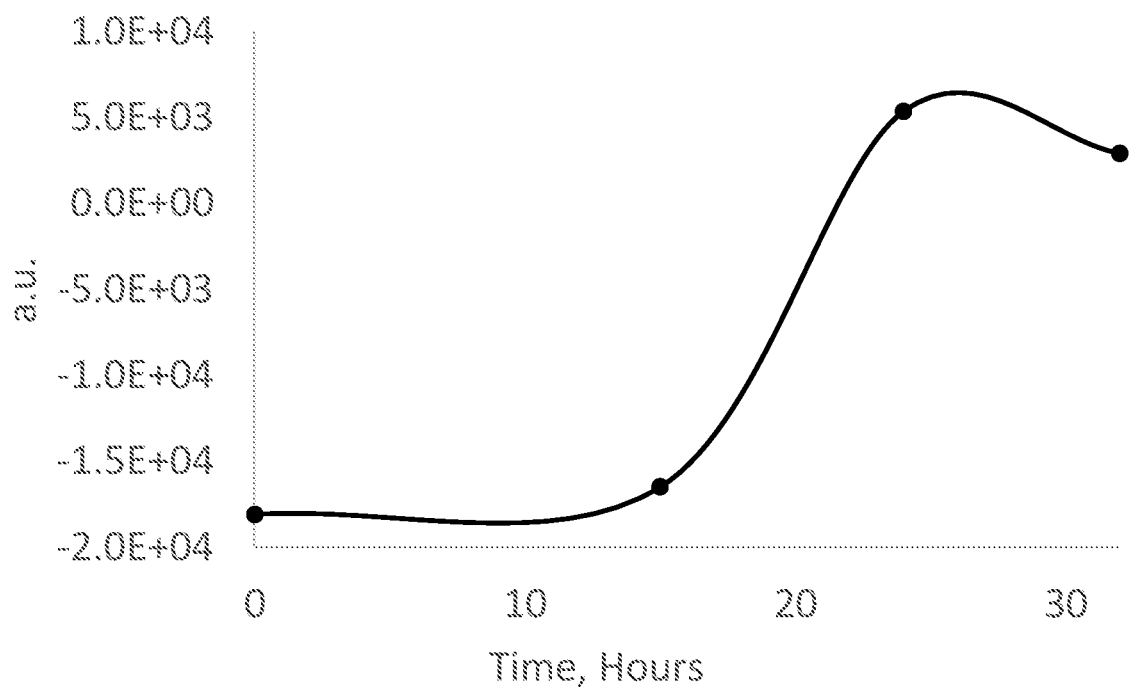
FIG. 34 shows the product of Red-Blue×Green-Blue× Red-Green corresponding to FIG. 33.

In addition, color changes (RGB scale) of the cottage cheese samples in the presence of carmoisine res were monitored for during the 32 h of experiment in order to quantitate the color change observed during the spoilage process. The results corresponding to carmosisine red as an indicator are presented in FIG. 33, which shows that in Red-Blue (dashed line, triangles), Green-Blue (dashed line, squares) and Red-Green (solid line, circles) there is a significant change upon the spoilage of the cottage cheese samples. In addition, FIG. 34 shows that the product of Red-Blue×Green-Blue×Red-Green also shows a significant change upon the spoilage of the cottage cheese samples. The results bolster the findings that carmoisine red indicator is suitable for spoilage detection or for monitoring quality of cheese products.

Example 13

Quality Indication of Whole Milk Using Combinations of Bacterial Indicators

As seen in Example 9, indicators, which change their color in response to an increase in bacterial population allow distinction of fresh milk samples from spoiled ones despite the masking effect of the turbidity of the milk. It was of interest to determine whether combinations of more than a single indicator can serve for monitoring the quality of food products.

Figure 35A:
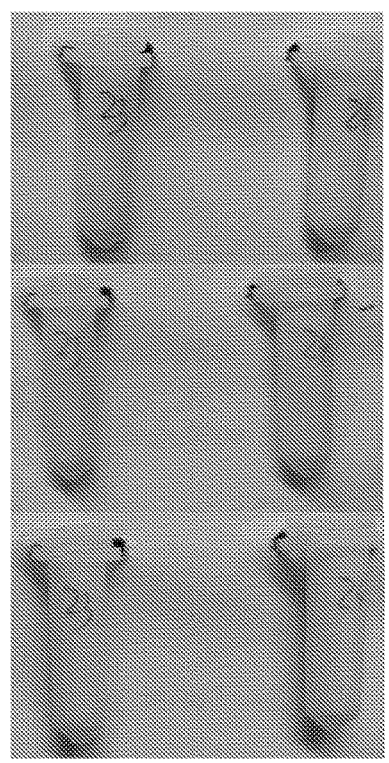
FIG. 35A is showing a whole milk sample stored in two Eppendorf tubes, each containing a solution comprising a combination of methyl red and carmoisine red, when fresh (top photograph), during a transition phase (middle photograph), and when spoiled (bottom photograph).

An experiment was carried out using whole milk samples and a combination of methyl red and carmoisine red. The sample-indicator mixture was orange at the preparation, when the milk was fresh (FIG. 35A, top) and the color changed to pink during spoilage after 36 h (middle photographs) and when spoiled after 80 h (bottom photographs).

Figure 35B:
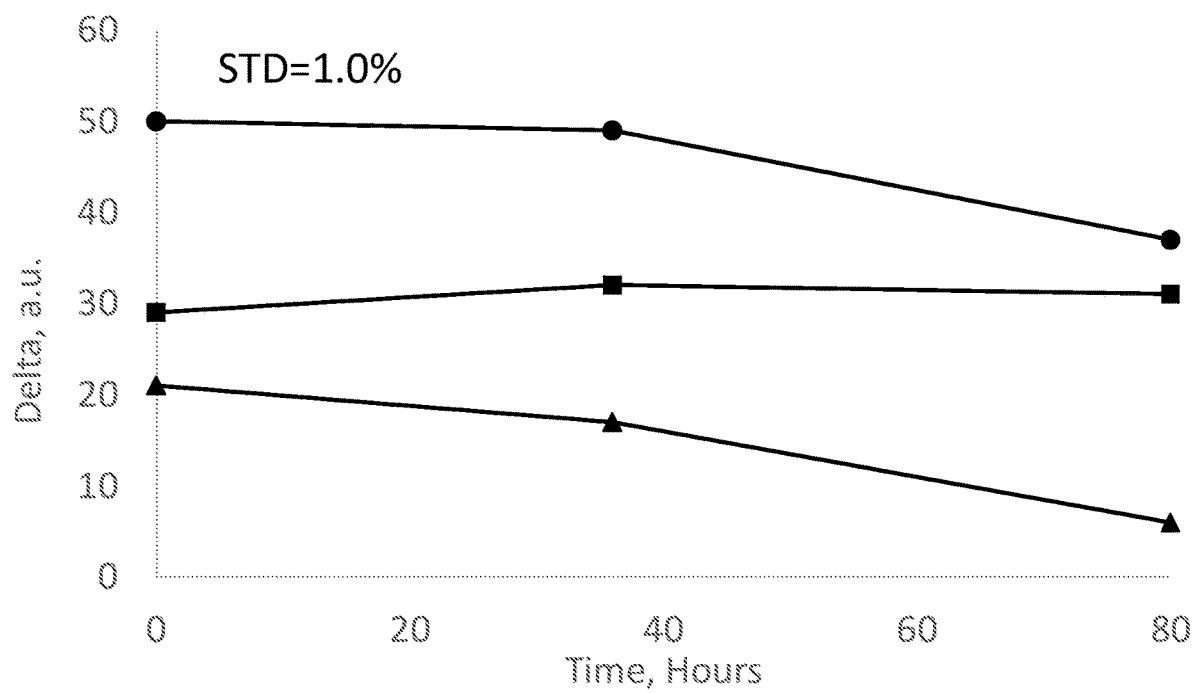
FIG. 35B is an image analysis in the RGB base in Red-Blue (squares) Red-Green (circles) and Green-Blue (triangles) corresponding to FIG. 35B.

In addition, color changes (RGB scale) of the above samples of milk with methyl red-carmoisine red indicator combination, were monitored for 80 h in order to quantitate the color change observed during the spoilage process. The result are given in FIG. 35B, which shows that in both Red-Blue (circles), Green-Blue (triangles) and Red-Green (squares) color ranges there was a significant color change upon spoilage of the milk samples. This change indicates methyl red-carmoisine red indicator combination is suitable for detection or monitoring spoilage of food products.

Example 14

Figure 36A:
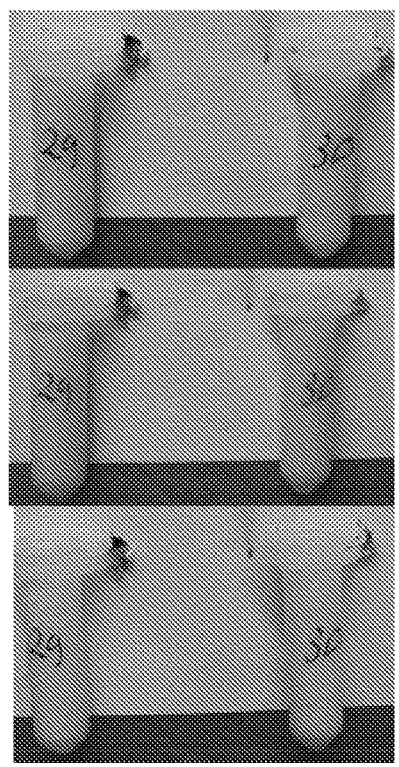
FIG. 36A is showing a whole milk sample stored in two Eppendorf tubes, each containing a solution comprising a combination of methyl red and Cr(III) indicator, when fresh (top photograph), during a transition phase (after 36 h; middle photograph) and when spoiled (after 80 h; (bottom photograph).

Quality Indication of Whole Milk Using Combinations of Bacterial Indicators and Transition Metals An experiment was carried out using whole milk samples and a combination of methyl red and Cr(III). The sample-indicator mixture was yellow at the preparation, when the milk was fresh (FIG. 36A, top) and the color changed to light yellow during spoilage after 36 h (middle photographs) and when spoiled after 80 h (bottom photographs) to white.

Figure 36B:
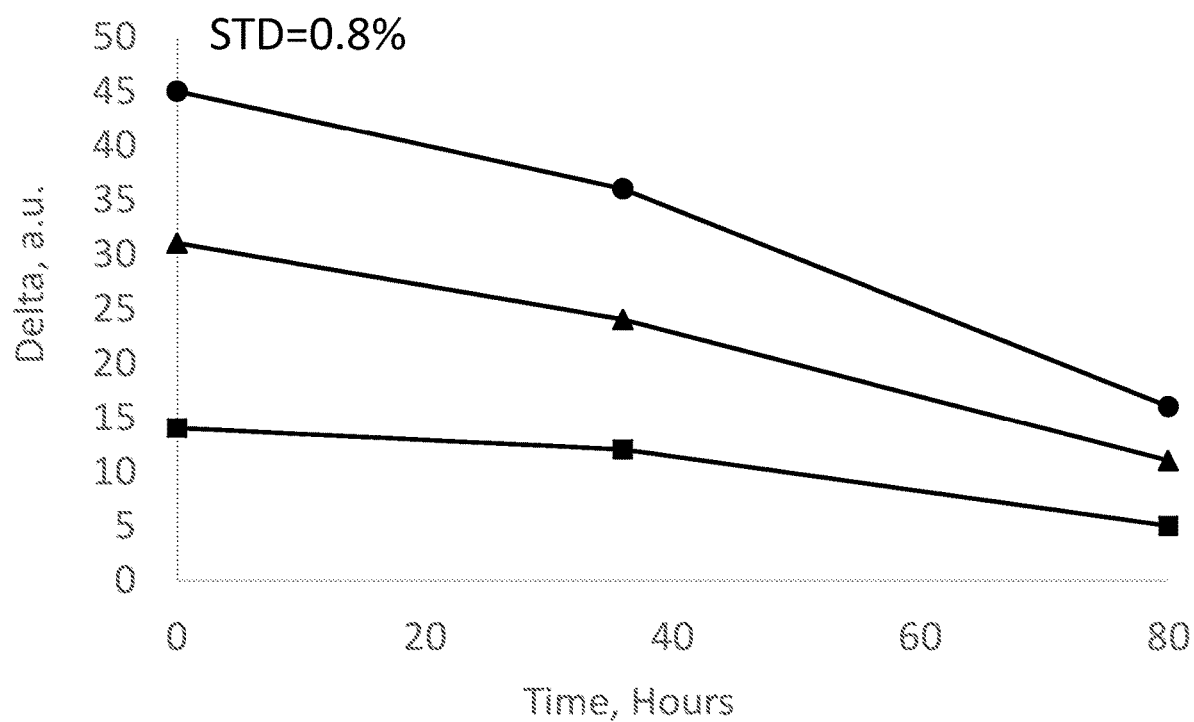
FIG. 36B is an image analysis in the RGB base in Red-Blue (squares) Red-Green (circles) and Green-Blue (triangles) corresponding to FIG. 36A.

In addition, color changes (RGB scale) of the above samples of milk with methyl red-Cr(III) indicator combination, were monitored for 80 h in order to quantitate the color change observed during the spoilage process. The result are given in FIG. 36B, which shows that in both Red-Blue (circles), Green-Blue (triangles) and Red-Green (squares) color ranges there was a significant color change upon spoilage of the milk samples. This change indicates methyl red-Cr(III) indicator combination is suitable for detection or monitoring spoilage of food products. An experiment was conducted with whole milk samples and a combination of methyl red and Cr(III).

Example 15

Controlling the Point of Color Change During Spoilage

Samples of whole milk and ×10 diluted milk were prepared from the same batch of raw milk in 50 ml tubes. Each sample was added one indicator as follows: Sample 1 of whole milk with indigo carmine indicator having an indicator concentration of $2.78 \cdot 10^{-8}$ mol/ml (WM1-IC); Sample 2 of whole milk with indigo carmine indicator having an indicator concentration of $7.13 \cdot 10^{-8}$ mol/ml (WM3-IC); Sample 3 of whole milk with methyl red indicator having an indicator concentration of $1.46 \cdot 10^{-8}$ mol/ml (WM5-MR); Sample 4 of ×10 diluted milk with indigo carmine indicator having an indicator concentration of $1.5 \cdot 10^{-8}$ mol/ml (M10-2-IC); Sample 5 of ×10 diluted milk with indigo carmine indicator having an indicator concentration of $8 \cdot 10^{-9}$ mol/ml (M10-1-IC); and Sample 6 of ×10 diluted milk with Bromocresol Green having an indicator concentration of $2 \cdot 10^{-9}$ mol/ml (M10-5-BC). The concentrations of indicators within samples 4-6 were in the range of $2·10^{-9}$-$1.5·10^{-8}$ mol/ml. All samples were kept at 20° C. and monitored for pH, bacterial count and color change. The results are given in FIG. 37A, which shows total bacteria counting (solid line) and pH (dashed line) in the milk samples during spoilage as a function of monitoring time. Double sided arrows indicate the time points, in which color changes occurred in the indicator solutions according to the notations of Samples 1 through 6 above. The diagonal arrow indicated the point of time, in which phase separation occurred during the milk spoilage process. A significant correlation was witnessed between the initial indicator concentration and the total bacterial counting in the same samples ($R^2$~0.982).

Figure 37A:
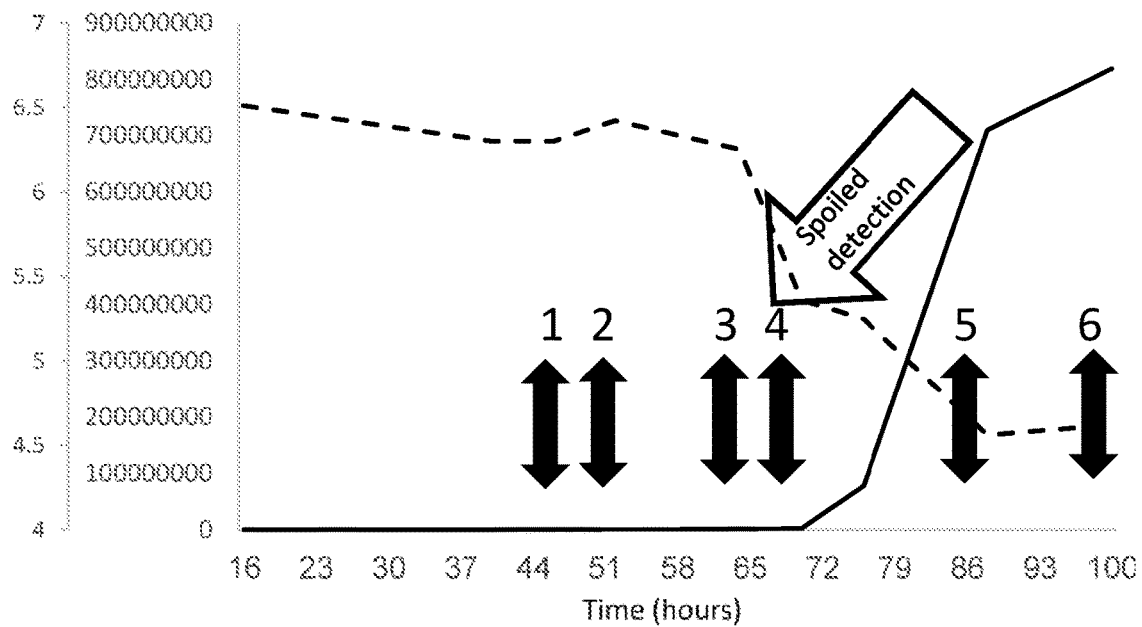
FIG. 37A is a graph showing total bacteria counting (solid line) and pH (dashed line) in milk samples during spoilage as a function of time. Double sided arrows indicate the time points, in which color changes occurred in the indicator solutions of Samples 1 (whole milk, indigo carmine); Sample 2 (whole milk, indigo carmine); Sample 3 (whole milk, methyl red); Sample 4 (×10 diluted milk, indigo carmine); Sample 5 (×10 diluted milk, indigo carmine); and Sample 6 (×10 diluted milk, bromocresol green). The diagonal arrow indicated the point of time, in which phase separation occurred during the milk spoilage process.
Figure 37B:
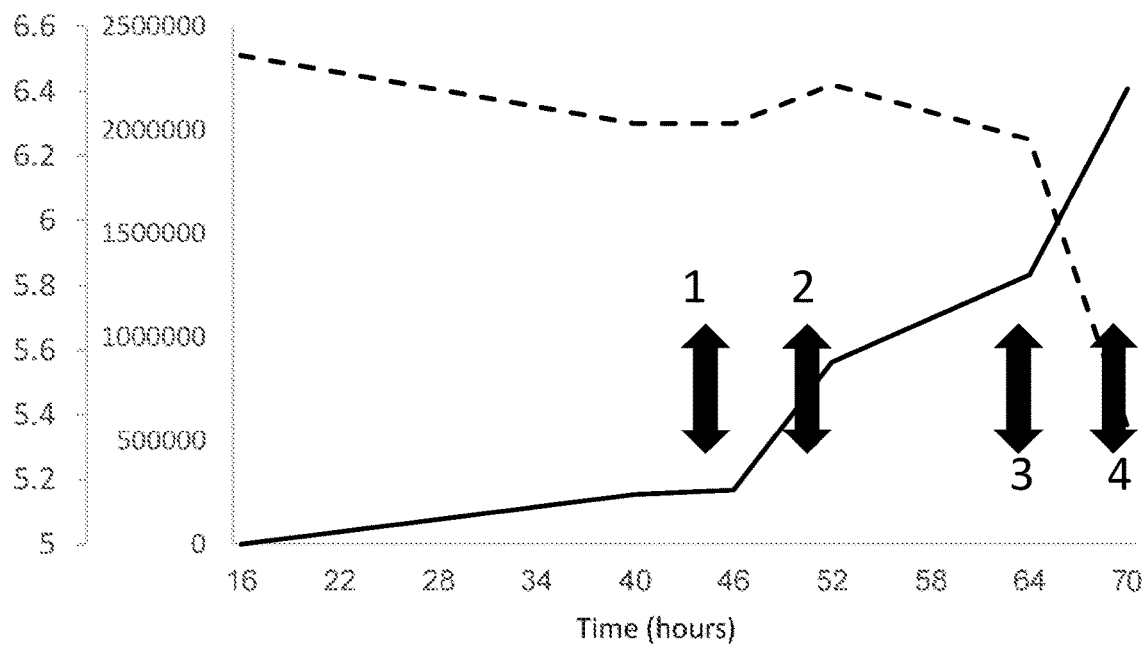
FIG. 37B is the section of the graph of FIG. 37A, which focuses on hours 16-70.

FIG. 37B is the section of the graph of FIG. 37A, which focuses on spoilage period (hours 16-70).

It can be inferred from the above results that using bacterial indicators, it is possible control the time point of color change during spoilage by changing the indicating system setup, e.g. by changing indicators or indicator concentrations and controlling the dilution. Furthermore, the above results show that the color of the indicator solution is in correlation with both total bacteria count and pH.

Example 16

Correlation of pH and Total Bacteria Count Between Indicator and Whole Milk

Whole milk samples (a) with no indicator, (b) with indigo carmine set I; (c) with indigo carmine set II, and (d) with methyl red were prepared in 50 ml containers. Diluted milk samples (×10) (a) with indigo carmine set III, (b) with indigo carmine set IV, and (c) with bromocresol Green were similarly prepared in 50 ml containers.

Figure 38:
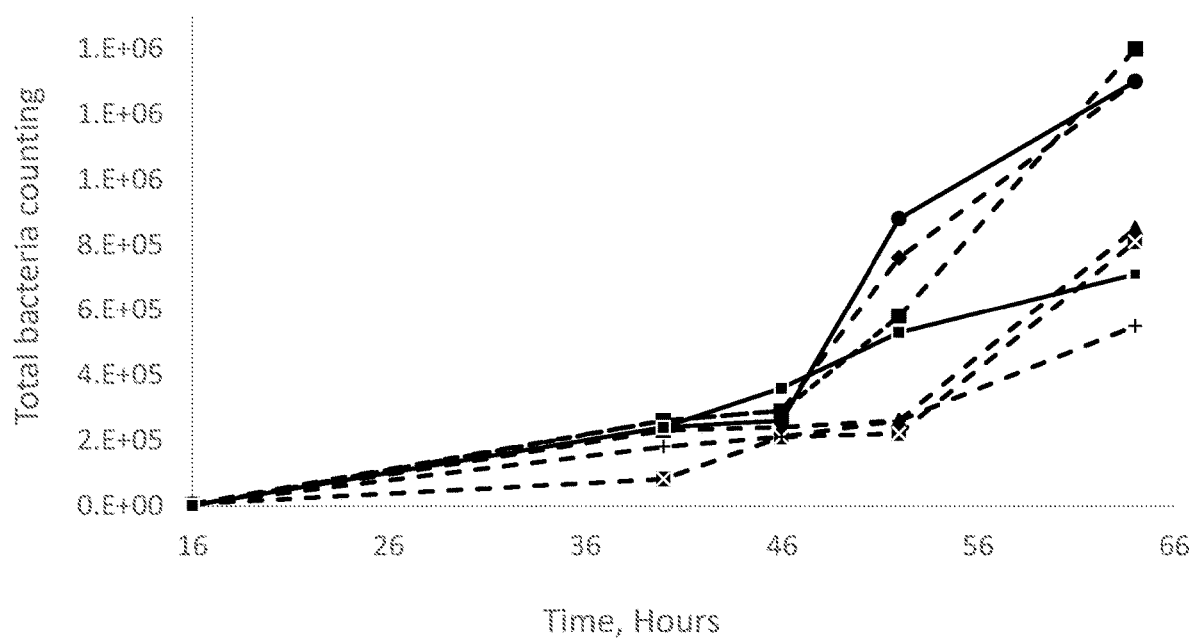
FIG. 38 is a graph showing the bacterial count of milk samples vs. time for whole milk samples with no indicator (solid line, circles), with indigo carmine set I (dashed line, diamonds), with indigo carmine set II (dashed line, squares) and with methyl red (dashed line, triangles); and of ×10 diluted milk samples with indigo carmine set III (dashed line, squares with X marks), with indigo carmine set IV (dashed line, "+" marks) and bromocresol green (solid line, squares).

The samples were kept at 20° C. and the bacterial count of the samples was monitored for 66 hours according to the standard protocols for dairy samples of a licensed microbiological lab. The result are given in FIG. 38, which shows the bacterial count of whole milk samples with no indicator (solid line, circles), with indigo carmine set I (dashed line, diamonds), with indigo carmine set II (dashed line, squares) and with methyl red (dashed line, triangles); and of ×10 diluted milk samples with indigo carmine set III (dashed line, squares with X marks), with indigo carmine set IV (dashed line, "+" marks) and bromocresol Green (solid line, squares). $R^2$ correlations of bacteria count in milk/indicator samples vs. bacteria count in. whole milk were calculated using Microsoft Excel. The result are: $R^2$=0.9886 for a whole milk sample with indigo carmine set I; $R^2$=0.9184 for a whole milk sample with indigo carmine set II; $R^2$=0.9033 for a whole milk sample with methyl red; $R^2$=0.7896 for a diluted milk sample with indigo carmine set III; $R^2$=0.7996 for a diluted milk sample with bromocresol green; and $R^2$=0.8691 for a diluted milk sample with indigo carmine set III. The results indicate that the presence of indicators does not substantially influence the reproduction of bacteria. Thus, these indicators may be used as a part of the two part apparatus disclosed herein, in which, according to some embodiments, the diluted food product becomes spoiled at about the same rate of the food sample to be monitored.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A system for monitoring food freshness, the system comprising:
   (a) at least one food packaging containing a food product; and
   (b) at least one chamber comprising a sample of said food product and a composition comprising at least one indicator, wherein the food sample within the chamber is diluted compared to the food product,
   wherein the at least one chamber is attached to the at least one food packaging or to a storage device with the at least one food packaging, and
   wherein said at least one chamber is an impervious three-dimensional structure.

2. The system of claim 1, wherein the at least one chamber comprises a transparent window, such that at least a portion of said chamber is being externally viewable through the transparent window.

3. The system of claim 1, wherein at least one indicator is selected from bacterial indicators, redox indicators and pH indicators.

4. The system of claim 3, wherein at least one indicator is a pH indicator.

5. The system of claim 1, wherein the at least one indicator is selected from bromothymol blue, cresol red, phenol red, methyl red, bromocresol blue, indigo carmine, carmoisine red, tartrazine, bromocresol green and methyl orange.

6. The system of claim 1, wherein the composition further comprises at least one transition metal moiety.

7. The system of claim 6, wherein the transition metal moiety comprises Cr(III).

8. The system of claim 1, wherein the food product comprises a dairy product.

9. A system for monitoring food freshness, the system comprising:
   at least one food packaging containing a food product, and
   at least one chamber comprising
      a sample of said food product;
      a composition comprising at least one indicator; and
      a plurality of compartments, separated from one another by a membrane,
   wherein the at least one chamber is attached to the at least one food packaging or to a storage device with the at least one food packaging, and
   wherein said at least one chamber is an impervious three-dimensional structure.

10. The system of claim 9, wherein said membrane is impermeable to particles having an average size distribution above 10 nm.

11. The system of claim 9, wherein the membrane comprises pores having an average size within the range of 0.01 microns to 1 micron.

12. The system of claim 9, wherein the sample of said food product within the at least one chamber is diluted compared to the food product within the storage device.

13. A system for monitoring food freshness, the system comprising:

at least one food packaging containing a food product, and at least one chamber, wherein said at least one chamber comprising a sample of said food product and a composition comprising at least one bacterial indicator, wherein the at least one chamber is attached to the at least one food packaging or to a storage device with the at least one food packaging, and wherein said at least one chamber is an impervious three-dimensional structure.

14. The system of claim 13, wherein at least one bacterial indicator provides an indication upon reduction of an internal double bond selected from an N=N bond and a C=C bond.

15. The system of claim 13, wherein the at least one bacterial indicator is devoid of quaternary ammonium salts and quaternary amine moieties.

16. The system of claim 13, wherein at least one bacterial indicator is selected from the group consisting of methyl red, indigo carmine, carmoisine red, tartrazine, bromocresol green and combinations thereof.

17. The system of claim 13, wherein at least one bacterial indicator comprises an azo dye.

18. The system of claim 1, wherein the at least one chamber is a substrate comprising a print of the food sample and a print of the composition comprising the at least one indicator, thereby forming a printed substrate.

19. The system of claim 1, wherein the storage device comprises a plurality of food packaging, and wherein the at least one chamber is attached to the storage device.

20. The system of claim 1, wherein said at least one chamber is an impervious three-dimensional structure made of materials selected from glass, rubber, polymers, gas impermeable polymers, liquid impermeable polymer, gas and liquid impermeable polymers, metals, paperboard coated with a waterproof polymer and combinations thereof.

* * * * *